United States Patent
Olek

(10) Patent No.: US 10,781,492 B2
(45) Date of Patent: Sep. 22, 2020

(54) EPIGENETIC METHOD FOR THE IDENTIFICATION OF SUBPOPULATIONS OF CD8+ T LYMPHOCYTES, IN PARTICULAR CD8 ALPHA AND BETA T LYMPHOCYTES

(71) Applicant: EPIONTIS GMBH, Berlin (DE)

(72) Inventor: Sven Olek, Berlin (DE)

(73) Assignee: EPIONTIS GMBH, Berlin (DE)

( * ) Notice: Subject to any disclaimer, the term of this patent is extended or adjusted under 35 U.S.C. 154(b) by 0 days.

(21) Appl. No.: 16/299,676

(22) Filed: Mar. 12, 2019

(65) Prior Publication Data

US 2019/0211403 A1    Jul. 11, 2019

Related U.S. Application Data

(63) Continuation of application No. 14/443,223, filed as application No. PCT/EP2013/074642 on Nov. 25, 2013, now Pat. No. 10,273,545.

(30) Foreign Application Priority Data

Nov. 23, 2012 (GB) .................................. 1221133.0

(51) Int. Cl.
*C12Q 1/6886* (2018.01)
*C12Q 1/6881* (2018.01)

(52) U.S. Cl.
CPC ......... *C12Q 1/6886* (2013.01); *C12Q 1/6881* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2010/0047778 A1 | 2/2010 | Koehler et al. |
| 2012/0107810 A1 | 5/2012 | Olek et al. |
| 2013/0260378 A1 | 10/2013 | Olek et al. |

FOREIGN PATENT DOCUMENTS

| | | |
|---|---|---|
| EP | 2141245 A1 | 1/2010 |
| EP | 2199411 A1 | 6/2010 |
| EP | 2248913 A1 | 11/2010 |
| WO | WO 2010/069499 A2 | 6/2010 |
| WO | WO 2012/045888 A1 | 4/2012 |
| WO | WO 2012/158556 A1 | 11/2012 |

OTHER PUBLICATIONS

Bilic et al., "Negative regulation of CD8 expression via Cd8 enhancer-mediated recruitment of the zinc finger protein MAZR", Nature Immunology, 2006, 7, 392-400.
Campbell et al., "Total lymphocyte CD8 expression is not a reliable marker of cytotoxic T-cell populations in human peripheral blood following an acute bout of high-intensity exercise," Brain, Behavior, and Immunity, 2008, 22:375-380.
Chetty et al., "CD3: Structure, Function, and Role of Immunostaining in Clinical Practice," Journal of Pathology, 1994, 173:303-307.
Correa et al., "Bisulfite genomic sequencing to uncover variability in DNA methylation: Optimized protocol applied to human T cell differentiation genes," Inmunologia, 2012, 31 (4):97-105.
Ehrlich et al., "DNA methylation in cancer: too much, but also too little", Oncogene, 2002, 21, 5400-5413.
Hamerman et al., "Distinct Methylation States of the CD8/3 Gene in Peripheral T Cells and Intraepithelial Lymphocytes1," The Journal of Immunology, 1997, 159:1240-1246.
Hassan et al., "Cd8 enhancer E8I and Runx factors regulate CD8a expression in activated CD8+ T cells," PNAS, 2011, 108(45):18330-18335.
Kioussis et al., "Chromatin and CD4, CDBA and COBB Gene Expression During Thymic Differentiation," Nature Reviews: Immunology, 2002, 2:909-919.
Sehouli et al., "Epigenetic quantification of tumor-infiltrating T-lymphocytes," Epigenetics, 2011, 6(2):236-246.
Ushijima et al., "Detection and interpretation of altered methylation patterns in cancer cells", Nature Reviews, 2005, 5, 223-231.
Wadsworth et al., "Origin and selection of peripheral CD4-CD8-T cells bearing a/β T cell antigen receptors in autoimmune gld mice," Eur. J. Immunol., 1990, 20:723-730.
Watanabe et al., "Long-Term Depletion of Naive T Cells in Patients Treated for Hodgkin's Disease," Blood, 1997, 90:3662-3672.
Werwitzke et al., "CD8$a$+$β^{low}$ Effector T Cells in Systemic Lupus Erythematosus," Scandinavian Journal of Immunology, 2008, 67:501-508.

*Primary Examiner* — Carla J Myers
(74) *Attorney, Agent, or Firm* — BakerHostetler

(57) ABSTRACT

The present invention relates to a method, in particular an in vitro method, for identifying CD8 positive subpopulations of a mammal, wherein said method comprises analyzing the bisulfite convertibility of at least one CpG position in the CD8 beta and CD8 alpha cell specific bisulfite convertibility gene region according to SEQ ID No. 1 and 2, wherein a bisulfite convertibility of at least one CpG position in said gene regions is indicative for a CD3+CD8+ and/or CD3+/−CD8+ cell. The analyses according to the invention can identify CD3+CD8+ and/or CD3+/−CD8+ cells on an epigenetic level and distinguish them from all other cells in complex samples, such as, for example, other blood cells.

9 Claims, 5 Drawing Sheets

Specification includes a Sequence Listing.

SEQUENCE LISTING

<160> NUMBER OF SEQ ID NOS: 25

<210> SEQ ID NO 1
<211> LENGTH: 46586
<212> TYPE: DNA
<213> ORGANISM: Homo sapiens

<400> SEQUENCE: 1

```
gccaagctca atggttccct tttcccggtc tttaggattt tgggcaaatt tattcaagat      60
ggatacattt ggttccacaa gggggacact ttggggttca caaggatggg ggccacagct     120
caccagggca gaacttgagc ccctatgac ttggggggtt gatggtggca gagaagtctc      180
tgctgggtgt gtgggaggat ccctctgagc gagggaggaa tctggtaaaa gtagtaaaga    240
tccactcatc aggacctgtg cttcttgcct atgttttcag gatccatggg ttaagcagct    300
tctgtgaggt tgtagtattg ctgtagtatc catgcaggca ttgggggaca aaggttcctg    360
atataccttc cccttgaggc cttgcaaaaa gaaaaacaag agagtctcaa tacatgcacc    420
aagtcaaggt gttggttact tattaagtaa tgactgattt ttttctgtga ctcagtcgag    480
tcagatgttg tgtcaaattc aacacagaaa gagccaggca tatagcactt gataggccta    540
gggttaccac aggatccaac cacatttgat tcaggatctc aaagccagaa acctctgttt    600
ctgtttcttg tgatttcttc tcagaaagag gaaaccacac acagagaatt acctgctcag    660
ttattcccca agttaatat catttgggaa agcgggtgag ggttttatcc ttccctcttg    720
ggcatcactg tcaattttat tgccatggtt aatcaaggtg aatttcaata gtgtctgacc    780
tgcaaattag ttttctgcca tttggaatca aggatgtacg ggtcaacagc tgcaggagac    840
ttcagagagg tccccatgct taaaaaattt ctctcaggag agtagtaagg tagggtggct    900
attgtcatca caggttggaa gacaagatgg tcacaaatgt tagagaattt attctgatgg    960
aaacttctcc tccgggggtac tttataatgg acatgaagac tcaacttcag gaagatgtaa   1020
gttttcccca gttaatctac agatccagtg cattcaaaat gccaaccaga ttttgctcac   1080
aagctgatta tcaaattcat atggaagtat aaagggccaa aaatagctga ataattttgc   1140
tgaagggtaa gggggggacc cattattcca catatcatga tttataaact ctagtaattt   1200
aaacacaaat agaacaatga aagagagtag ggggcctaga aaatacagat gtgaacatgt   1260
tggagatggc tgggcactcc tgtgggtaaa ggattcgatc attagtgctg tgacattggc   1320
ttcccatgtg ggaaaaacgt aaaacttgaa ctctatctca aaccattcac aaatgtatac   1380
tccagataga ataaatatga aaagcaaagt ttcaaaactt tttaaaaaaa tgtgttttta   1440
agacagagac atgataaggc acagaatttc ttggtcaaaa tataaaagga caagccataa   1500
aagtgtgatg ttaccattcg aacatttgtt taaagtatgc agggcaaaaa ccaatacaaa   1560
gttaaaggac aagtctcaaa ttagtagaag atatttgcag tgcataaaag caacagaaga   1620
tctttatcca taacatatca gactctcaca aagtaataag ttaaagacag cagaattaaa   1680
aatgggcaaa gtacgtgacc aagccaatat ccaaataaaa agatgccaaa cattacttga   1740
atcagtgaga tgcaaatgaa aacaaccaat atcattttat attcaaatta gcaaaatgaa   1800
caagaccaat aacatcaagc atgagggagg atatgaccaa ataactgtga tgcagtgttg   1860
atggggatgt aaattgttac aactgcagtg gagataattt gggatatcta gtaaaaatat   1920
ctattaaaaa tgaagatgct ctggccccag aacttccact tccagattca ttgctcagag   1980
aagttttgat gtataagagt gttcacagaa gcacaaacaa cagaaattgg aaaattgtaa   2040
taataattat aaactaatat ctaataggg aatgaataaa attgtaatac attaataaaa    2100
tatgacacaa taaatgaact agatccacag gcatcaacac aggtaaatct caaaaatatg   2160
ttgaatgaaa taagcaaatt ttaaaagtgc atgtacactc tgacattatt tataaaaaat   2220
aaaagcacat gccatatatt attcattatt atgtcattgt ttatagatac ttacataata   2280
```

```
agagaatcac aagtataaaa aaagcctgga ggcagaaccc acaaatttca agatagggta    2340
tgcagtatgg aggatggaat aggggtgaag aaggggtctc aacacaaaca ttttattgct    2400
tgaaataaaa gactgaagca aatttggcaa aagttaaatt tgctaaatct gacagattta    2460
tttagcaaat ctgctaattt gctaaataaa cttgaagcta gtatgttacc ttcagtagtt    2520
ttctttatat ttggcataat tcataattca tgggaggagg taattacata ttaaaaatat    2580
atattcactg gctgggtgca gtggcttatg cctgtaatcc cagcactttg ggaggccaag    2640
atgggtagat cacctgagtt caggagttcg agaccagcct ggccaacatg atgaaaccct    2700
gtttctacta aaaatataaa aattagccgg gcgtggtggc gggcacctgt ggtcccagct    2760
actcaggagg ctgaggcagg agaattgctt gaactgggag atggaggttg ctgtgagccg    2820
agactgtacc actgcacttc agtctgggtg acagagcgag actccatctc aaaataaata    2880
aataaataaa aataaataaa taaagtatat attcataatt aacagagtaa ctgtatgtaa    2940
tgagtacctg ctgtgttcca ggcactgttt aaagtacagg catacctcat tttattgcac    3000 tttattttt tattgtgctg cacgatgtt gtattttag caaattgaaa gtttgtggca     3060
accctgcctg gagcaaatct atcaatgctg ttttcaata gcatgtgttg actttgtgcc    3120
tctggatcac ctttaataa ttcttgcaat acctcaaact ttttcattat tattgtgtct    3180
gttctggtga ctgtaatcag ttatttttga tgttactatt ttaattgttt tagggcacca    3240
tgaaccatgc ccatttatga cagtgaactt gatcctaaa tgttgggtgt gttctgactg     3300
ctccatgacc agccattctg tatctccttc tccttaggcc cccctatgcc ctgagccaca    3360 aaatattaa aattaggcca attaataacc ctacaatggt ttctaagtgt tcaagggaaa     3420
ggaagaattg cgcatctctc actttaaatc aaaagctaga aatgattaag tttagtgagg    3480
aagggatgct gaaagtggag acaggctgaa agctaggtct cttgtgtcaa ataatgagcc    3540
aagttgagaa ggtagagaaa aagttcttga aggaaattaa aagtactaat ccagtgagca    3600
catgaatgat aagaaaacga aatagcctta ttgctgatat ggagagagtt ttagtggtct    3660
gggtaaatcg gaacagccac aaaattccct taagcaaaag cctaatccag agcaaagtcc    3720
caactctctt aaattttatg aaagctgaag tggtgaggaa gctgcagaag aaaagtttga    3780
agctaggaga ggttggttga ttcaagtggt ttaagggaag ataccatctc cttaacatca    3840
aaatgcaacg tgaagaagca ggtgctaata tagaaactaa taggtgctgc agcacagcag    3900
gttatccaaa agagctttct aagattattg acaaaggtgg ctacactaaa caacagattt    3960
tcaatgtaga caaaacagcc ttatattgga agaaagatgct actaggtctt tcatagctag    4020
agagaagtca atgcctggct tcaaaggaca gcctgcctct cttgttaggg gctaatgcag    4080
ctggtgactt taagttgaag ccaatgctca tttaccattc taaaaccct aagtcccta      4140 agaattatgc taagtctact ctacttatac tctgtaaatg gaatagcaaa gcctggatga    4200
cagcacatct gtttagagca tggtttactg aatatttaaa gcccactgtt gagactcgct    4260
caggaaaaaa gattcctttc aaaatattac tgctcattga aaatgtgcct ggtcacccaa    4320
gagatctgat ggagatgtac aaggagatta atattgtttt tcatgactgg taaaacaaca    4380
ttgattttac atggaccaag gagtaatttt gactttcaat tcttattaag aaatacattt    4440
cgtaaggcta gagctgccac agatgatgat tcctctgata gatctgggtg aaaccttctg    4500
gaaaggattc accattctag atgcaacaaa gaacatttgt gattcatggg agcaggtata    4560
aataccaaca ttaggaggag tttggaagca ggtgattcca attctcctgg atgagttgga    4620
ggagttcaag acttcagtgg aggaagtaac tgcaagtatg gtagaaatag caagagaact    4680
```

```
agagatagaa gtggagtctg aagacgtggc tgaattgttg caatcccgtg atcaaactta    4740
acacatgagg agtttattct ctctgatgag caaagaaggt ggtttcttga aatggaatct    4800
actcctggtg aagatggtgt gaacattgtt gaaatgacaa cagaagatag agaatgttac    4860
ataaacttag ttgagaaaga ggcgtcagta tttgagagga gtgactccaa ttttgaatgc    4920
tgttctactg taggtaaaat gctatcaaac agcatcgcat gctacagata aatcttttgt    4980
gaaaggaaga gtcaatcaat gtggcaagat tgttgttgt cctatttac gaaattggca      5040 cagccacgcc agcctttggc aaccaccatt ctgatcagtc agcagccatt gacatcaagg    5100
caagatgccc tccatcagca aagaaattat gactcactga agctcaggt gattttagca     5160 tgtatttggt aataaattat tttttgatta agacgtactt ttttttttcag acataatgtc   5220 tttgtacact tagtagacta ccttataggg taaacataac tttatgtac actgggaaac     5280 caaaaaatga atgtaactgg ctttattgtg atatttgctt tattgtggtg gtctggaact    5340
gaacctgaga tatctctgag gtttgcctat actggaattt ccaaggttag tgaaacatcc    5400
tttctgcagc ctgagtggtg agatttaggc tagtctcaaa aatataaaaa ataactagaa    5460
tataatgtaa taacagtgat cattaagata acaatgctag cagctaccat tgactgagta    5520
gtatgtgcca tgcactctgc aagcactatt ttattaatgc tcatgtgtga ggtagatatt    5580
atcattattc ttgttttata ttcaaggttc agagaggtta attcacttgc tcagagtcac    5640
acaggtagcc cagatctgct atgtgccagc cctaattact gagccatcct gtctgtccca    5700
ccttttctga cccaactccc cacttctgaa ccacaggcgg tgtagctggc tttgaatata    5760
ggtgctcttt ttatataggt actcttgaaa ggatcaactt tacttttttt ttttttttca    5820
aataatccaa taactttgac ttttttattag gttacactgg cattctccca agttttcat    5880 caaactcatg aagcctgctg ctccttcaat tctcaaggcg ttggagtgag ccgcctggg     5940 gtgaatcgaa gctttcggat ttatcaaatg tggtgtgatt tctaagacgc cattgagccc    6000
tgctaaagga gttgctaata tccacctcgt tctgcggtta agaaaccaac aggaaaaaga    6060
acgcacaact cccagcacag tgctggcgcc tgtgaggcac tcagccgacg ggagctttgt    6120
tcttcgttgt attgtggcgg ggaagcaaca tggggccttg tcctgcggac acacttgagt    6180
taagatcaca ctggggctcc ttcaggcct gggccaagtt ggggcacagg ccgagttcgg     6240
ttgttgctgt agcctcagaa ccacccgag ttgactgaag acactcgggg gcctccataa     6300
ctgagagcag gcagaggcat tgttttaac ccagtgtgga cccccaaatg gaacattttc     6360 cttcccctagg tgaacgcctt cggaaccctc cgaaaatcgc agtttcactt ttagcaaaga   6420
gccccgctgc agcaggggaa agccccaca aaccccgtcc tctccaaagg gaatgttccg     6480 agcccctgc ttcctccacc cttctcttcc cctggttaa ttccttcgct ccagctcgtt      6540
ctgccttctt tctttctttg ccttttcgag gcccgctctt ctctgatttt gaagggctgg    6600
cgcaggcttg ggcacttctt tcaggttctg tattgtatgt ctgccctgtg cttctcctt    6660 ttgcaactcc gagcaactct gtgcttggat tgcagctccc aacagtcctg ccctgacttg    6720
ccccagtcac agggcagaga tgaaccaggg actgtaccca gggttttgag ttcctgccat    6780
atttatagca tcaactctcc tttagctctt gggaaaaagg gttttaaagt gctgcaatct    6840
tctaacacaa aattatatca gtgctgaaaa tgtgttttcc acttataccc cagcaggaaa    6900
aaaaaaaaag atgatatctg tttcaggtaa gagtcatgat gacctcagaa agcaatatca    6960
gaagctatca aaatgtttat acctgtatat tcagtagtcc attctggaac atttctccag    7020
```

```
tggatgtaat cttagtcttg cacaataga gtatgaacag atgttaaa tgttaaaagc      7080 aatggaaatg ttcagaaata aagcaatatt taagtaaaca atgataatgc attcaatata   7140
attttaggca ttaacatgat gatgttttag aattatgaaa cctatggaaa ggttgacaag   7200
gaaaacgcag acagcatgct tgatataaac atacattcag catgattata actatgtaaa   7260
atgtaaaaaa tgttttaaa acattagaag aaaatacacc aagatgcgtt tcccttgctg    7320
ttgtttctag tggctaattt ttgcaatgtg tattactgca gttatatcac ctttacaaat   7380
ggaaagctta aaataactc acttcccttc ccagagagca atgttcagtg caaagccaca    7440
ctccactcca gggatggcct tcagcactgg acttttggg agccagaatc aagcagtatg    7500
tgtcacttct tatctcatgt tgttggtgcc acttactcat atgttgtctc atcattctgc   7560
agttgtttaa tgtgtttata tctttctcta caaccatttt ttaaaagcta tttttaaaat   7620
tgtggcaaaa tgtatgcata acataaattt accattttag tcatttctaa gtatacactc   7680
cactggcatt aagtatattt atattttgt gcaatcatta ccaccatgca tccacagaac    7740
tttttcatct tcctaaacta aaactctgta cccactaagc accaactccc cattccccct   7800
cccccagttc caggtaaccg ctatgatatt ttcagtttct ctgacgaatt cagagacacc   7860
actcttggta cctcctgcaa gtagaatcat actgtattta ccttttgca caatcatttt    7920 ttaaaactta aaaaaattt ttaattaatt tttttgagac agtctcactc tgtcacccag    7980
gctggttggt gtttgcagtg gcacgatcat ggctcactgt agccttcacc tcgtgggctc   8040
aagtgatctt cacatctcag actcccgagt atttgggact acaggcaccc accacggtgc   8100
ccggctaatt ttttaatttt ttgtggagat gaggtcttac tatgttgccc aggctggtct   8160
caaactccta ggcccaaggg atcctcctac ttcagccttt caaagtgctg agattacaaa   8220
gcgagccaca agcctcggcc tgcacaatca ttataaaaag ctctctgagg ataaggacca   8280
aggccctgat ttgttttcat tgtaaacata atgttcattt gctcattgat ttgatattga   8340
ctgtgcaccc acacgtgtgc tgggcactgt tcgaggcagg gtttaagaaa cgctcaagaa   8400
gcacatgtgg tctctcaagg ggacggtgta gtggacagag ataacaaaga aaaacacaga   8460
gaagaaagaa tgacggagag tgagaagtgc tgtaagtgca gtgacagaca ccgcccaag    8520 gcctcctgga caggctgcat gtttgtagga tgatggggag tggtcctgga aagactgag    8580 gaggagccct gggggtcca ggcagagaga ggaggggcac agagctggag gacgaaggg     8640 cctttgtaca gcatgtgtgt gtgtgtgtgt atgctggggg acacgcaggg agatggcagg   8700
cctcagcact ggggagagct ggagtgcatt ctagatgcag cagggagctg gagcagggac   8760
cctcttctcc ctgcctggcc tgagagcagg gaaggaggcc ctgggctgtg ctgattgca    8820 gtcaacactg aggaacaagt gccaatgctt catgcagggc acaacctctg ccacactttt   8880
acctatgtga ccttctgggc caggtactgt gaggtgcttc atttctcaga tagcaaggct   8940
gaggctcaga tcaatgctgc tttgcacaca gctggaagtg gccaaatcag cccgaaaccc   9000
ccattttgtt ctgcatcttt gtgcagggct gggtggctgt gtgtgcaatg tctgttgtgc   9060
tggacatgca acaggaaagc aattgttacc tctaattttt aggaggccaa agggcaagaa   9120
gccacgtgct ccaggccaaa gagcagctaa gggaatgaag agtaaatctg tgattgaatg   9180
aatgagcaga tgaaaagaga aaagcctcc ccctgcacaa acctgcaacc cattcccttc    9240
ctggggtcct gtggggaggg ggcttttcat cagtgccctg gtcagggaa gagagaggga    9300 ggccttgtgg tggagggaag gggaggagag ctcaccatca gaggtggaaa gaaggttcta   9360
gtccctccag agcacactca gggatgcttt cttgtgcttc tgtcccaagg ccttgtctcg   9420
```

```
accttgctta ctataaacac agtgctacat cctgctttc ctttacttca ttgcataaac    9480
cttccctgaa tcgcttccag aatctttaga accaccgttt ttaaggtttg aatacttgta   9540
taccaagtaa atgaccacag cttattgaaa ctcctctttta tagtcaacca cttaggttgt  9600
tctattgtta tttctagaac acataactaa tgccaataaa taatgatgat ggcacagatt   9660
agtatttcct gaggatggat ctcttgcgtg ggttccaaag ctctaagcaa tttatatggg   9720
ccctggagtt tcctccacag ctcctaaggc agctctggca catgaggagg ctgggaaaag   9780
agcaggggtg atgggtgcat ctgccttggt aagtgaactt gttggttctg tcccacgcag   9840
cttgggtgtc ggtgtggggg gtgtgctgct ggggttggag aggggccgcc ctacataacg   9900
tccccacata aaaggggcag gtgtgcaggt ggtcccaggg atggcggcag ctctgtctga   9960
ctcccccta ctgggggct atgggggctg tgggagtgga gggtgaggat caccgtcctc   10020
caggatcccc caaccctcc ttggccattc cctttgactt ccttgggaaa gagtccaggc    10080
ttcagaggat tctttgctca tttcaatctg accccatttg aatccccaag ggtcgcagta   10140
aaccccaggc acacaaagac agaggcttgt ggctggcttg cggttgctgt gatcacgatg   10200
gaatcagaca acggctgccc tggcaggcag cacccaggca cctctcaggt gggaaaagac   10260
tgagccaggt gaatgtccca gagctccagc cagctcaggc tcctatgggt gataactgca   10320
ctagacacct ctccgaagaa gccaacagaa actgcatgca gcggcaacat gagcaaagat   10380
aagtgttggg acccgttctt cgctgccacc tccaagtctg aacagcaggc tctaaggggg   10440
gcatgggagc ccctcagaaa gggccactgc ccatgcctca cctcctgccc gccactccac   10500
tctttattgt cctacctgac tgtaacaggc tgcatgctca acatggtgtc agctgcccca   10560
aagagcacca ggaggagaca ggggtgccat tcggacatga acaggagctc ctacctgaat   10620
gtgcagacct ccgccactgg agctctcggg gggaaaacat ccatgacagc ctccctgagc   10680
cttgaaacat ttgcagacca agcaggctca ggtgcccgtg tttgcaggcg gttttttaga   10740
acgtatcatt tgtcttatat tgatgtaccc ttcaaagccc gggaggaagt gtggtcttgt   10800
ggggagctct gtgcaggcaa catgagagtc tgtattgtct tcctagctct gccccggttg   10860
tcagaggagt ccatctgggc cacaggggtg aggagccgtc acccctgcct tttgtttagc   10920
cggtgacacc tccccagttg tgtggcgggt gatgcagcaa taatgcccac gagctcctct   10980
caacaatcaa aacaaaacag agagccactc taaaacagtg gctttcttgc aaatggaata   11040
tgctgagaat ctgtgacatg tgcaggtcgg taagtgagaa ggaaacagga accaccaatc   11100
gattctgaca atgtagaaag cagtggaggt ttggggccag gagaacaaaa gacctatggg   11160
agaggcggtg acccaggaag ggtggccatg gacttgggtg catcacctga gccctgtcac   11220
ttggaaagaa ccctaacgac catcttaatc ctgcctgtat agataccta ctgtgccgct   11280
gctgggtgtg aagcgtggct actaaaaatg ttcacttcat ttttaagaag tagaacaggt   11340
tcaaggttat tcctgtagac gacagtgtcg ctctcgccca agtacactgt gggaggcttc   11400
cttagcagga tcgaaagggg tggaattaca gtgggcactg gaattggctg tggttcacac   11460
atgtagacat gactgtgaat ttcttgtttt ttttttttt tgagacgggg tctcactctg   11520
tcacccaggc tggagtgcag tggcatgatc tcggctcact gcaacctctg cctctcgggt   11580
tcaagcgatt ctcctgcttc agtctcctga gtagctggaa ttataggcac ctgccaccac   11640
acccagcaat ttttgtattt ttagtagaga gagggtttca ccatgttggc caggctggtc   11700
tccaactcct gacctcaggt gatccactcg cctcggcctc ccagagtgtg aggattacag   11760
```

```
gcatgagcca ctgtgcctgg ctgactgtgg attttgtggc agcaaagagt tcatcttggt   11820
tcatcagcta agactgtgct caagtgtaag ccactgagta gacttgttta tgagtgattc   11880
ttggaagctt gcaaggactt cttttgagtt aaaaaaaaaa aaaccttctg gtagagttaa   11940
acatgaattg gcttgccctg agagttcggg ttttatgtca cgagaggtag ttaaatgtgg   12000
gctgggggcc tggtgtggtg gctaatgcct gtaatcccaa cacattggta gactgaggtg   12060
ggtggattgc ttgagcccag attgagacca gcctggccaa catggtgaaa ccccatctcc   12120
acaaaagtta aaaaaattag ccaggcatgg tggcatgtgc ctgtggtccc agctactcac   12180
gagctaagtg ggaagatcac tggagcccag gaggcagaga ttgcagtgag ccgagagggc   12240
accactgcac tccagcctgg gtcacagagc aagaccctat ctcaaaaaaa aaaaaaaaaa   12300
tgtggggtag acaaatatgg ggcagggttg ctgtaaaggg tgttcacgtt ttattttgga   12360
agctgaataa tgtagacttt aaattgtttt tgcaacatag agatctacag ctctggacta   12420
atggatcaga ttttgctagt tgcaaagatt tttgaatttt aattgcagtt tgctgctgtt   12480
tcacccacaa caaagtaga ggaagaactc atagcttata tgcagtgatc atgaactctg   12540
gggctttgta gatgagacta ggaaaacttg tgcaggacct gaagttgaac tgccttggct   12600
cttgttccca tgtgctgggg gatggggcaa ggacatctca ccaggtatca gtgggtggtc   12660
tacactattt gagtaaagtc ctatccttat agtgttgctt tcctgcctgg tgacttgact   12720
gagtttaggc ttagcgacct gcttataaaa tggcaagagt acgtacttgc ataagcggtt   12780
aattgacata atgcaggtaa atggaacagt accaaacgct taataacaaa tgcttaataa   12840
atgaagatgg tggctggcaa gtgggggcga atgtcaataa acaacatgta aaaatatgga   12900
tcatctggtc actttaaact tttagtgaga tcaaatgtgg gcaaaatttc tctacaaata   12960 actgaattg tgtgtgtgtg tgtgtgtgtg tgtgtgtgtg cgtgtctgga cccacagaga   13020 agttttaat gtagatatat aaagtagata atctcattta tattttggaa aattttaatt   13080
tttaaaaatt tttgttattt gatgatgatg atttgtttcc ccttcagagg aggttttcca   13140
gctctaggag atgctgttga caatctctct tctgaagtta aggggcccct tgagtggctc   13200
tggccactga gaagtgaaac cctgggagca gctagagatg ccagcctat gatattcaca    13260 gccaatgtgt taagtgtgaa gttctgtgca agtaggtttt aaataggtac agcctaaaat   13320
acataatttt cttattatca aaatcatgtg ccttttttaag gaaaaatcta agaaacacag   13380
aaaagcaaag agaagaggaa aataaagtat tcatatgggc ctacctccaa agatgcaacc   13440
agcaacctct actttattat cttctggatt cctttactct cttaaaaatg gggtcctact   13500
ctagttgttc taataactct tcatcacttt ttaaaaacag taatttgttt cttgtcatta   13560
tatcttctcc atatatacat acacactctt tttttttttc aaaatggaga ttgcattgtt   13620
gttttgcctg gctgtcagtg taatactcag atggaagtac tgcacatgca taaacaagac   13680
gataaagatc acttgtaatc tgccccacac caaccctgt cacatttgga gttaccattt    13740
tggcatatgc tctttacttt tttttttttt tttttttttg agacggagtc ttgctctgtt   13800
gcccaggctg gagtgcagtg gtgtgatctt agctcactgc aacctccgcc tcctgggttt   13860
aagcgatttc ccccgcctta gcctcagcct cctgagtagc tgggactaca ggtgcatgcc   13920
accatgcccg gctaattttt tgcattttag tagagacagg gtttcaccac attggcaagg   13980
atggtcttga tctcctgacc tcgtgatctg cctgtctcag cctctcaaag tgctggaatt   14040
acaggcgtga gccaccgcgc ctggctggca tatgatcttt ctgaatattt tgtttactgt   14100
ggattcctaa ttagggaaaa aggagtcagg ctggggggag tcaggcgggt gggagcaagg   14160
```

```
gaaaataaaa agagaaagca gataagcaac aagtctgcct ttctttatgg tccaggacac    14220
acagccctcc tgagcaagta actctcacca gacacgtgca agttagctca ctgcaacctt    14280
ggcgttatta atactacaca aagccctctt caacagatag cataaacgct accctgtaaa    14340
atcaccagca agcctttgtc tccttgcagt cagtttctct ctgctgcctg cctattgtcc    14400
ctctggcaat gtattttcta ataaatcttc tgccttcttt tacctgcaac tgtttcggta    14460
aatcttttac ctccacacca ccggctgtca ttcccccatg acatttaaca catgtttctt    14520
acacacagat aatttctctc ctcttctgcc gagagctggg ttcatagaat atctaacgtt    14580
tgataatctg cttttaaat ttaataatgc attgtgaaca tctttccact tattaaacat    14640
tcttgcacag cattatttta atgtcattta ttaccttgca tggatgtatt ctcatttatt    14700
tcactggtag atatgtagtt tttagcatgt ttttctttt tttgagacaa ggtctcgctc    14760
tgtcacctag gctggagtgc agtggtacga tcctggcaca ctgcagcctc agcctcctgg    14820
gctcaagtga tcctcccacc tcagcctcct aaagtgctgg gattacaggc atgagccaca    14880
ggtcccagcc agttttagc atgttttcaa tatgcttaca atactctgat gcatgtcttt    14940
gccactaata attcttgtgg ggccaggcat ggtggctcac acctgtaatc acagcacttt    15000
ggcgagtcag ttgaggccag cagttcgaga ccagcctagc caacgtggcg aaaccctatc    15060
tctactaaaa atacaaaatt tagccaggtg tggtagcata tgcctgtaat cccagctact    15120
tgggaggctg aggcatgaga attgcttgaa cctggcaggc agaagttgca gtgagccaag    15180
atcgtgccac tgcactccag cctaggggac agagtgagac tctgtctcca aaaaaaaaaa    15240
attattatta ttattgtgca taaccaataa tatcatgaat attttcgtga tatattcata    15300
gaagtgaaat tgctggttca aaaaaaaata cacaaatttg aggctctaga tatgtattgc    15360
caaattgccc ctcagaatgg tgggaccagc ctggactccc agcagtggat tatgaatggg    15420
cccgtttatc agcactctta tctatctgaa atgctatatt atggtacaat ctggtaaaat    15480
ccatttaaaa atgcattcct tttgtttatt attttaataa ttccaattta tattagaaac    15540
cagtttgcat ttaattttat tagattttgt tattaattaa attactaaat ttctggtttc    15600 tgtccttta agaaacgtta tttatttaaa tcatttagaa tttctttgg tgtcagatat    15660 gaagggctaa aactccattt tttccaaata tttaaccaat tgtctcggca ctctttatta    15720
taatctatta ttttgtttg tttgtttttg agacggagtc ttgctgtgtt gtccaggctg    15780
gagtgcagtg gtgcgatctt ggctcactgc aacctccacc tcttgggttc aagagattct    15840
cctgcctcag acttccaatc gctgggatta taggcacctg ccatcatgcc cggctaattt    15900
ttgtgttttt gtagaaacgg gtttcaccat attggccagg ctggtcttga actcctgacc    15960
tcaggttatc tgcctgcctc gacctcccga aatgctagga ttacaggcat gagccaccat    16020
gcctggcttc tataatctat tctttcccca tgtatgtgac tgctacattt gtcatgtaat    16080
ccacatgttc aaatggagtc tattcatgca tcacttcagt gattgaaatc agcaatttaa    16140
aattgatcag taaatatcta gcagctgata atcccatgag gagagagaaa cttcttttgc    16200
ctttgagaaa gaaaatgttt tccttctgat tctaaaagaa taggtgagtt gctttcctct    16260
atctctgcaa ttttttccctc tgctgggacc cacagatggg gaaatgagaa cctctgatga    16320
ggcagcagaa acccagaagc cagaacaccg ctaaccagta atgaagctgt gggatcactg    16380
aagctcccct gccccaggga gacacggggtg gtcaaagtag aaactgaaga tcagcctcag    16440
agactcccag actgaggagt cagcctaatt ttctgataag aaattaaaga ctaggggctg    16500
```

| | |
|---|---|
| ggggagtgag agaagtatta ttctcaaact tttaggaaaa aaaacaaaat gaaacaaaac | 16560 |
| agtgaaaaga atgatcagga agtcagtaac ttcattgtgc ctgtgcttac aatgccatct | 16620 |
| ttttaactgt aggaattggc cattgtaata acaaatgcca ctgctgtaag gaaggtatca | 16680 |
| gtgagtggga aagggtctta attgtgctgt ctcatctgac gagcttgagt gttcacacca | 16740 |
| cgcagccaca gccagagcag cacactctat ctggggtggt gaattgtaat tttaggcaaa | 16800 |
| tatcagagga gaaataaat taccttgagt gattataaaa ctaaaaatag taagagaagg | 16860 |
| ataggtgcag tggctcacgc ctgtaatccc agcactttgg gaggctgagg agggtggatc | 16920 |
| acctgaggtt aggagttcaa gaccagcctg gccaacatgg tgaaacctcg tctctactaa | 16980 |
| aaatacaaaa ttagccaggc atggtggtgt gtgcctgtaa tcccagctac tcaagaggct | 17040 |
| gaggcgggag aatcgcatga acccgggagg cagaggcttc agtgagccaa gatcatgcca | 17100 |
| ctgtactcca gcctgggtga cagagtgaga ctcgatctca aaaaattaaa aaaaaaaaaa | 17160 |
| gagatatcat atcaaataag aggaagggca cggtcacatg aggttttat gcagcaccaa | 17220 |
| ataacctgct cgagtgggga ataaatgccg acacttcagg ttgtgagcca ctatgatacc | 17280 |
| cacttttcct gcccccaccc tcccttctgt tgttggtttg ccccccaatt tactgctccc | 17340 |
| tgtgtgggtt gagctttgta agctgcccca aatccttttt gggaattaga caatgcaagg | 17400 |
| ataaataaaa acattgattc ttaggagctt ttcaatgtat tataaaattg aattttaaca | 17460 |
| gacaggttaa taaaaataaa aagaggaata cttttgtttt gatctcttgt tatttaaatg | 17520 |
| aaatttatcc cttttccagg ggaaagtttt tgttttgaca ctcatggtca gcactggtct | 17580 |
| cctctcctct cctctcctct cctccctct cctcccctcc cctctcctcc cctcccctcc | 17640 |
| cctcccctct tctctcctct cctcttctct ctctccctct ttcccctcca cccttcctct | 17700 |
| tgctgcagcc tcctcacagg gtcataggca caggaacaca gctacagaca tgaagatgct | 17760 |
| ttcctgtgtt acaaaaaagg atagtttaaa taattccctg catcctgctt ttcctcctta | 17820 |
| atagtacact ctggcagtgt tgccaagtta atctgtcttt ttttttttt ttttgagatg | 17880 |
| gagtctcact ctgttgccca ggctggagtg cagtggtgtg atcttggctc actgcaacct | 17940 |
| ctgcctccta ggttcaagtg attctctgcc tcagcctccc gagtagctgg gattacatgc | 18000 |
| ccggctaatt tttgtatttt tagtagagac agaattttgc catgttggcc aggctggtct | 18060 |
| caagctcctg acctcaggtg atggcccacc ttggcctccc gaagtactga aattacaggt | 18120 |
| gtgaggcacc gcaccggcc ctctcctctc ctctcctccc ctcccctccg ctctcctccc | 18180 |
| ctcccctccg ctctcctccc ctccgtccg ctctcctccc ctcccctctc tctccctccc | 18240 |
| tttctctctc acccttcccc ctccgcccat ttctccctct ttttccctcc ctccctccct | 18300 |
| ccttccttc cttccttcct tccttttctt gggggcagt ggggacagag ccttgctctg | 18360 |
| ttgccctggc tggagtgcag tggcttgctg taacctcaaa cttctggact aaagtgaccc | 18420 |
| tcttgcctca gccttcctag tagccgggac tataggcatc caccaccatg cctggctaaa | 18480 |
| ttttgtattt ttaatagaga tggggtttca ccatcttgac caggctggtc tcaaactcct | 18540 |
| gacctcgtga tccgcccacc tcagcctccc aaagtgctgg ggttacaggg gtgagccacc | 18600 |
| gtgcccggcc aaatcattct ttttaagtca ttcttttgat ggctacacga tattttggg | 18660 |
| tatagataga cagcaactta ttaaatgatt ccctattgat tatcttgggg ttgtttccca | 18720 |
| ttttattttt gcccaaacaa tatggataga atcatctttg tatatttatt ctgatgcaat | 18780 |
| gatgcttcta ctttcccggg gacccattcc caggagtgct gagtgacagt ccctaattca | 18840 |
| tattaaacac tactagatgg tgcccacctg ttttccacaa agctgtagcg ctcgcttatt | 18900 |

```
ccagcatcag caacacctgt gtgcccttgg ccacaagctt tccagcagtg agcagcatca    18960
ctgttttaca ttttttactca gtgacatttg tatgcaaatg acagattatt attttttctgg  19020 aaaatgtatg cttaaccatg ccagggtcat aactcatgct atgaaaaaga ttttggtgta    19080
gaggtcatgg cagaagaaat gagaacgtgt gaatcagctt tcttctctta cacacacaca    19140
cacacacaca aaagtcttaa ctgagcttgg atattaaaag cagtgtgggg gagagggtgg    19200
ggaggtttgg agttaccatc aggagcgtct gaccaggctc aaacgtggga tagctgtcca    19260
ttgaacagcc ctgtatgtca caatgactag gaaaaattta taagacagac gttccaggcc    19320
gggcacagtg gctcacgcct gaaatctcag cactttggga ggccaaggca ggaggatcat    19380
gaggtcagga gttcgagacc agcctgacca acatggtgaa accccgtctc tactaaaaaa    19440
tacaaaaatt agctgggcat gatggcgcgc acctggaatc ccagctactt gggaggctga    19500
ggcaggagaa tcgcttgaac ccgggaggcg gaggttgcag tgagccaaga tcgtgccact    19560
gcactccagc ctgggcaaca gagcaaaact ctgtctcaaa aaaaaaaaaa aaaaaaaaa     19620 aagacaagcg ttcccctgca cccgcccac caaatcgcct gccacacaca gaagcacgca     19680
caggcgcact ctgaaattac acagataaaa ggccgacagt attactccct ctcccactga    19740
taagctcctt tctgtgctgg gtggggctgg cggactttct gatggaggaa gatggaactg    19800
ccagagtgag cactggctct ggtctgagcc actgtgagcc tttcttctct cctccttcat    19860
cccctacacc acaagataga ccacccaaca tggctttctg agtttctagg gagctgggct    19920
ttgagcaggg cccacaaaag gacttcaacc aaagcctgct tgtcttgtgg aagccaccct    19980
acctccctgt ttccaaacca gaagcatcag tgtggctgca gggtaggtac tcggatagag    20040
gcagggacga cccaaactcc atcttctgcc ctggcccagc tagagccttc gtgatccgaa    20100
ggcaggcccg ccttttgtgc tgatcacgtt tactgttgct ctcccctccc tatgtccccc    20160
aaacttggct gaggctgagg taagggtgga gggtgggag tcatggcctc ccttttgcct     20220
ggtctggtct tgcccagaca gcaggcctag cccagcaggc agcttcaggc ttgcaggatg    20280
ctgaaggggt gctggggagg ggtgtgtggg aagaggagc ctccacccct ccaccaacac     20340
cacctcacat cttcccctcg taactttgcc ctcacccaac cgcagagacc tccacaaaat    20400
ctgtaagagg ctgtgaacaa cactcccagc caaacataac tttttgaga aggcaatcca     20460 tgccctctgc ttgtgttggt atcacccggg tctttctctg gtctgtccgg ggctggcatg    20520
aggctgcagc cagtgaggca ctgaggccac tcactcttgg agccacgcaa gtgccagcct    20580
tgagcctgtg tcccccggt catgagaatg aaagcccgtg gggttaggga catcttctga     20640
gccaaatctt tagtgtctga aacacatgcc tgattgagat ctgagttgtt gaacttggtt    20700
ctctaagggg attgtccatt gtacttggca gagtaaacat cccgagtggt cctcacagcc    20760
ttgaggagca cagaaaggtg ggtgggtgga tgggtggggg agccagcagg ggaggtgctg    20820
ggaggggcag tggagaggga gggctgtgct cccagcttgt gggggcctaa ggactttcta    20880
tctgagcctt ttgctttgtt cattcattca tttcagttct ggcctcaggc ttaggagtga    20940
tttgtacagg tggcaggaaa gagccagagg accccacag gcctcggccc tgggctacta     21000
gggagggaac tgaggcctag aggctgtaag caagactgcg agccctgggg gcccaactat    21060
gtccatcctg gccatgccgc acccctagtc ccagcacagg gctggctggg cacacagaag    21120
tttccccaaa tagatatatt tgaaccagca tcaagaaact taagggattg gcatggtgtg    21180
ctcatgcctg taatcccaac actttgagag gctaaggtgg gaggatcgct tgagctcagg    21240
```

```
agtttgagac cagcctgggc aacatagcga gacctcatct ctaccaaaaa taaaaaaaaa   21300
ttagctgggc atgctggtgc gcacctgtag tcccagctac ttgcttgagt cagggaggtc   21360
aaggctgcag tgagccatga tggcgccact gcacactagc ctgggcaaca gagcactgta   21420
cacacacacg cacaccccca aggaagagga gaattgagtg cagagttgtg ggtattagtt   21480
cagtcataaa tggggacagg agtggaaatg gtctacaatt aaaaatgcat gaaaaggcca   21540
ggtgctgtgg ctcattcctg taatcccagg actttgggag gccgagatgg atggattgct   21600
tgagcccagg agttcaagac cagcctgggt gacatgggga accccatctc taccagaaa    21660 tataaaaaat tagccaggtg tggtagtgca tgcccatagt cccagaaact caggaggctg   21720
aggtgcaagg atcgcttgag cctggagac agagcctgca gtgagctata agtgcgccac    21780
tacactccac cctgggtgac agagcaacac cctgtctcaa acaacaacaa aattatgtag   21840
aagaatggac atggtttcct ttcaaattta gaagtctaag caaagctctt aaaagggtac   21900
tcgcttgtga aaggcagtaa actaatggga aaagcaggat ccaggagagc caacagtact   21960
gtggaggttg taagtgtctt tttcagcgcc tctgctttca gctttacagg aatcacacgt   22020
gtcgtgcata tttctgtgaa tctcaaaccg acgcagggct ggggaatatg gtttccttct   22080
gtttgagtta tgtaactggg aggactccag gaaccagtga ctcacagttc cccggggagtg  22140 tcagtgacgc atcgaaggag gtttcccaag aagcgacaga ggaaatatct tttggaaggc   22200
ctctgaagac agggctcttt ctgtctttcc ctttgactgg gtggtagatt cggatcagct   22260
ttgcagccca cgcggggtcg gggatcactt tctgaaaaca agttgcccac ttcctacagg   22320
tagagacaca agctgcgggg cggggtggg gatgagtaag gatgaaaggg aggggtggt    22380 gtaggacccc ccttcttctt ttgaacaggc cggggtgggc tccacacctg caggctactt   22440
cccactgaaa ggaaggggc gggggaggg gggaacacca gtgctgctcc cagacccatt    22500
aaggtccaca gaaaacaca gaaaaggaag tactatagat gttctccttc agggcagaga   22560
acccaggctc acctaaggtt gctggagtgc agcccacccc tgccacgagc ccagccccat   22620
gtgaacttcc agacaagtaa atgcaattgc aaatgtagct cgcccaaagt ctacagctgg   22680
taaagaccca ggctgtgctg tctggccacc tcggacctgc ctcaccgtga tttccatggt   22740
tcagattttt ttaatttatg aataaatctt tcgtttgtgg atattttat tgattccaat    22800 ttcttattat aacaatggcc agaggttctt ttttccaaa cttttaattg cttttttccc    22860
aactacaaaa gtaatacatg atgtaaaaat tcacacaagg aactgtacaa agcagaagtg   22920
gaaattccgc agagtaactg caattaacag ctgaaagtaa atccttacag accttttcct   22980
gtacatatac aaacaaatat acccggaggc cttgatttat tattagagaa aaaagatcaa   23040
atctgcagaa caatattaga agatgtaatt ttctatattc tctattttat gtattatatt   23100
ctcaagattt caattttatg ttttaaaaaa tatgggaaga aaaaaaaaca agaaactttt   23160
tagaaaaaat ttatttttga gacaaggtct gtctgtgttg cccaggctgg agtgcagtgg   23220
cgtgatcaca gctcactgca gtctgaaact cctggggtca ggagatcctc ccacctcatc   23280
ctccctaata gctgggacta caggcaagca ccaccatgcc cagaaaaaaa tttaaaaatt   23340
ttttgtagag tcgaggtctt gctatgttgc ctaggctgct ctcaaactcc tgagctcaag   23400
tgatcattct gtgtgggcct cccaaagtac tgggattaca ggcgtgagct gtaatcccat   23460
gtgcttgctg aagaaacttc caaataccaa ttttacacat ttctacaatg ttctgtactt   23520
ggattttaaa aagtctcttt cttgaagtat aatttcatc tatatccata gctctaaagt    23580
caacatatct gagtgtacag cttgatgact tttactaatg aaacacactc atataagtga   23640
```

```
ttcccagatt gagaagcaga aatgctcacc ttcaaacctc atgctccctc ctaatgacca   23700
ccactggacc aagggtaact gtatcctaac ttctaacaac atatatttgt tttgcttgtt   23760
ttcttttgtg cttgaatttt aacagtgact acatattgtg ccatatattg tattaagaat   23820
aatctataca gatgttttaa aaatatatgc atttgtcata accatcattt gatatcagca   23880
tatatggatc tagctcattc cttagcagcc gcctaaaccc ccttattaga ctgtgtctga   23940
atttatctga ccagtcccct ttgatggaca tttggattat ttcccatttt tagctagtaa   24000
gcaacactag aaggaacaat ctgatgcgta tttctttgtg catgccactt tttgatgtat   24060
ttctttcaga taaatgccaa caagtggaat tgctagtcaa aagatagctg gatggagttt   24120
ggggggcata tttcatcata atggccctat agagtgtagt agcagctcag ctccttcttc   24180
aaacaaaggt caggtgctgg gtgcagacct tctcaccgca gcccccacca ttggcagccc   24240
agcctgctcc agctccctgg gcagccggag ctgagcccgc ctcggcaggt gcctgctgca   24300
cagaaaactg acagaggagc gcaaaccacc cctgccccca gcccaacccc atgagaactt   24360
gtgaacaagt acatgcaatt gcaaagacag cagcagggag acggtcaaat ttcaaagcct   24420
gcagtgggac aagaggcctt gtggcctgtt cttacttccg ctgtgcactg ggtgtgagcc   24480
ttcaaggagg gcagaccatg tgcactgcag gccttaatct cttatttgtt tgtgatgggc   24540
cgggtgaggg gcccacctga aacacgaacc ctagaggagt ctggtccagc tgaccccaat   24600
tctttcaccc ctcccctcag ccttggaagg cagcctgtcc cttgtcctca gagctgatgg   24660
gcagagcttt tgtttctttt gaacacctct tgctgaggca ggagtctagg gtctgggggc   24720
agggaatcta aggccaattc gtgctgaatc aaggagaaac atctatgtcc gggggcaggg   24780
aatctgaggc caatttgtgc tgacttctca aagctggatc aaatggaaaa cacctgggtc   24840 tggggcagg gcatctaagg ccaattcgtg ctgaatgaag gagaaacacc tacgtctggg   24900
ggcagggaat ctgaggccaa tttgtgctga cttctcaaag ctggagcaaa cggaaaacac   24960
ctgggtctgg gggcagggca tctaaggcca attaacatac accaaaagga aaaacccat    25020 ctccccacac tgagtaacca aggatcaaag gctactctcc ctacaaccct cccccttcca   25080
ctgcatctca gatggaaagg gagacggccc tggattgacc acagaccaag cacgggccat   25140
cccttcatcc gcatagggcg tcaattcacc tcagcctttc attagccatg gaccaaatcc   25200
ttcacccaga taaggggtag ccaacaggta cctcaaaagg ggtacttaaa acccagaaaa   25260
ctttgcaatt gggcccatgg gctatctgct tagggtccac tcctaccatg tggagtgctt   25320
tctcacttca ataaattctt ccttttgctg cttttattcc tttattactt tgtatgtttt   25380
gttcagttct ttgttcaaaa tgccaaggac ctggacaact tacactcaag gccctccttc   25440
cggtaacact gcatctatgc ctttctaact ccacccacca cacctcattc tgctgcggcc   25500
gcaccccaga tgccaggaga aggtcacact gccccttccc cagagtcgtc tttcctttcc   25560
tgtttttttt gtaacatttc ttacattctg tggttgtcac aggtaactga acataacctg   25620
atttgtcaat gtccttcttt gagctggcca ggaaaagcag gtgaggctgg attctccctg   25680
gacctggacg tggtgcttct gttaatgcag cctcaggttg cagtgtttta tggtgcaata   25740
gctcctaggc tgctaaagct caggtagggg cggctaagat gggtctcagg cacttttca    25800 aacccaggca cgaggtcctg ctcttcactc tccactcctg ctcagcactt tctccttgct   25860
ttttccttct ccaactgtca aggctaagaa tcaataagaa aatgaagaga catgtgacag   25920 aaccccctcat gcctcctacc ttctgttttgg tgcctgactt gaagccaggg atccctgcgg  25980
```

```
ttcaacccgc ggtagaaatg aacacgtgct agttcagctt gggagtgggc tgggagaggg    26040
gcctgaggca cctgcagcct ggctctgggt gccctgggcg cttcctagcc tctctaggac    26100
tctccacacc tacaacgtcg ggcaaatgag gatctcaggt gcaaaggag gatgtacaaa     26160 ttttctcctt ctggtttctg ttccacggag cactgatgtc tttgctgtag atgggctttc    26220
gcacgtttat gtcacaggag ccgtttgtta tctttaacct gggactttat ttgtacaact    26280 aagcatttg tataaaacaa acagaaaatg aaagaagcat taagccatgg gagagtagaa     26340
atgggagctg agaaacttaa gagtagaaat gggagctgag aagatgaagt gaactcctat    26400
cctcaaaccc gcaagttccc ggccccaaag gaagccctca gagactgata tgccttctgg    26460
gaactggaca gcccctctca gcaagcctca ttcccaacct gcacctggcc tctctgcgag    26520
gaaggtcagc cccagcctgg gaagaccaag agggagccag cccagcatca ccccatgaaa    26580
gacccaggac ccaatgttac tgccctacca gggcaaagca acctgcaaag atggtggcta    26640
aatggccacc actaaaggtc ccagttcagg gaaagcacag gagccggaag cggtggcatg    26700
ggcagcattt cttactcagt cctccagcac actctgtgaa gtgccctggg ggcaatgaaa    26760
ccttctccct agtattcccg atgacccacg aacaagttgc tcccatgcac atcacacaca    26820
gaaaggcctt gcagcagtga aaagcaggca gcttcagcag ccattgaact ctccaggggtt   26880 gaatgtgtcc cttctctcat ttttccacat cgtgctcgtt actgaccgat gtcttttgt    26940 agcaggacac caaaaccgta ttctctgctc atttgtaaaa tctgaaaaca acagcaagtt    27000
gtgaaaccac ttattttcag gcaaacgata ttgaatttcc tgtaacagag acaaatggca    27060
aatgagaatg cagagttcta ctccaagtag cctgggccg agagtttttt gttagtatgt     27120
ttctagggcc catcttagtc attaaaaaga ttgttaaggc taaaaaacaa aacaaaacaa    27180
aactgcagct caaagaacgg tagctttgaa ttgggttact tcctgtagta cctctaagat    27240
aatctaagag aatcacaaat ttatatcaag gggccagaag aaattagcct gcagatggga    27300
tgattttcta aggacagtta gaggctgggg aacaactacc tcaaatcgca actcagatct    27360
gtgagcacca caggctattt cctccatgcc tggatcatga gagcaaaacc agaggtggtt    27420
ttcaagcttt tttgaagcca caaacccttt tgttcaaatg acatgttaca ggtaagtgta    27480
aacccagaca atagaagaga gtacgtctgt tcaaaatgaa gagagtgagg aggtctcagg    27540 gtcccccac gaccacccag agcccctttc ctgcctcaag ctgatcctgg gcttgcaaaa     27600
gcatgaggtc ctgcatccag cctccccaaa actggcatca gatcactggg gagcaagtta    27660
aaatgaaggg gtggggacag acccagacca cagttagtac cagagaggga cttactttcc    27720
atgaaaggtc atcatgggag acattttgaa aggaactttc ttttttttt tgagacagag     27780 tttcactctt gttgcccagg ctgcagcgga atggtgtgat ctctgctcat tgcaacctct    27840
gcctccgggg ttcaagtgat tctcttacct cagcctctcg agtagctggg attacatagg    27900
cgcctgccac cacgtccagt taatttttg tattttagt agagatgggg tttcaccatg      27960
ttggccaggc tggtctcaaa ctcctgacct caggcgatct acctgccttg gcctcccaa     28020 agtgctggga ttacaggctt gagccactgc acccggcctt gaatggaact ttctagaggt    28080
ctggcctgag acagctacac tcaagttatt atctcttggg taggggcag cttctaaatc     28140 caacacacaa ggtgaaaatt gtacacaatt aaaatatcat tgaaaattgc ccataaaatc    28200
cagcaggcat gtttaagcca ctctcgatat aaatataatg tgtacaacaa tgcagagcat    28260
atagtaatat gaatttatat ggctatttac aattttagg tattcaaaaa tacattttgt     28320
ttgtccattg ctgcacttgc agagtggaat ttactgaagt gacttgagct tgtgctctga    28380
```

```
ctccggggtc ctggggccac atgctttaag gataataccc cagtgagtcc tcacactgac    28440
tgtgagattg gcactgttag ctcatttaac agacgagaaa tccgagactt ggagacgtga    28500
agtgacttgc tggctgtcac atggtgattg gcagacggga ttcaaaccca gccctgtctc    28560
cacctaaagc tggagctttt gagcaggaga acctgttgcc ctcttcaatt tagagttgtg    28620
tacttttgct cccccaaaca tttctgtata gaggggttg ttctaaggat caaatgtaat     28680
taactggata ggcagatgtg aaacagtctc tgttgtgagg aacaaaaatc aaatgcagga    28740
atgctgccct ggcccaggat ggcttccaac agcctcatga agacccagg acctaatgtc     28800 actgccctac cagggcaaag caacttgcaa aggtggtgac taaatggcca ccactaaagg    28860
tcccagccca gcccagggta agtacaggct ctttctcagc ttagtgggcc caagagtgc     28920 tatgtgactc tgtcaactcc tgggacccag atggggtcga gggcagcagg tgggacaaag    28980
gcagctccta gggaaggaaa gcaatggctg gtagaagagg ctggtcttca aatccgattc    29040
cagtagtctc tccactgatc tgtcaaatga gggtgataac cccttatctc acacagtacc    29100
aaggggatga aataataggt gggatgaaat aacggatggg atgagtttgg gatactctgc    29160
ggtattctgt gcatgcaaag cctgattgct ctcctcagga gagctaagaa tgttcttgaa    29220
atacatttaa cttactggtc aggtttttgt ttgtttaggt tatctcttag gttcctgaac    29280
tctatcaccc catctatta tacagtctgt aatttttttt tttagatgga gtctcactct     29340
gttgcccagg ctggagtgca gtggtaccat catagctcac tgcagccttg aactcctggg    29400
ctcaagtgat cctcctgctt cagcctcccg agtagctgtg actacaggtg tgcactacta    29460
tgcccggccg agtctatgat cttggaaga tgaggtctga ctttggctcc tcgctgcagt     29520
tagaggctgc aagctgcagc agggggctgag gaacccaagg ccacacccag gttatacact    29580
tactgtttca tgaaacgaag ccgggctctc ctccgccggc ctggaagagg aaagcaaggg    29640
cgccagtcag tgtgggctgt gggtcactgc gctgagcccc agaggccaag gaggattgtc    29700
acaggggcag ctgacacctc agcccacctc cctggtccca gaccctggcc caaacacttt    29760
acacatttta atcccttaa tgctcactga aaacctgagt tggatactac tttttaagatc    29820 tccattttat atgtgggaaa ctgagacaca gagtgagtga attactggat aacatgccca    29880
aagtcatgca gctagtaagt gggaaagcca gaattcaaac tcaattagtc agctgcagag    29940
tctgtgtcct taaacacacc tgcttgccct tcacagcagg tcagacatga aaggtcccag    30000
agacaggcag tctcaggcta gggcaattgc attcagaggg tgagcgagat ttcccactgg    30060
gagttaggaa gaaaataaaa gcatgtctat tgacatttgt atttcagcct ttattacttt     30120 tgatttcat ttatttttt aggaatgggg tcttattatg ttgtctaggc tagacttgaa       30180
ctcctgggct caagtgatcc tccctcctca gcctctcgag tacgggcact tgccactaca    30240
cccaacttac ttttcatttt gaagcacatt taataacata cataaaatat taaataagta    30300
aatacagcca actgctgcat ttactttata atattcaatt agctgtattc gcttatttaa    30360
tattttatgc atgttattaa atgtgtttca aaatatttta ccaatgagtt ccttccttga    30420
tcgagagagt ttgcaaacca ctgaaattta tgggtttctt agaatggggt acatgggccc    30480
ctctgtgggg aacaattgta ggcaaaagta tgctcctggg tgcatttctg tggggagagg    30540
tccgttattt tcatcgtatg ttcaaggggg tctgtgacct acaaaagtta agagccactg    30600
atctagttca tgcccttgct gtcccacctg cccatttcat agatgcgcag agaggggaag    30660
gggcttgctc gaggtggcac aggtgagcag aagaaccggg gtagagtctg ggctctgggc    30720
```

-continued

```
tctagggcag ccatgcaggc ctcccctctg gctccccgtc tttcttgtga acccagtgct   30780
gtgcagagct tggggtgggg gccatagaag gagacagtcc cgtctctggg gtggctggga   30840
gcagcagtca tttctgtttc ccacagcctc atcaatatcg gtgtcgtgga gaggatttct   30900
agcttctagg aacacaacac aaaccccata ggcaaacttt tctggacact gggctttggt   30960
ctcaactgct cacgtgagtt cccactcact gacacgtgcc gggtgccagg catttgggt    31020
aggaatttac aaacagcaac tctgggaggt agctaatgtc ctaccccat ctgaggcagc    31080
cgaggctcag agagaccggg gcactggatc aggaaacagc cacgttgcac tcaaacccag   31140
gtttgcctga ctccagggac agggtagtct ttggttttgg ctgcgtagcc ccaggccaag   31200
aactacctct ggaaataccg taggttctct gaggcaaatt cccaccaggc tgccatctgc   31260
tctgctcccc tagagaagaa aatatcccag ggacacttca aacagcaaac agggacaccc   31320
aacaacccaa gaggagacaa ctcacagcac aggtggatgg ccactcccag ggaaaccagc   31380
agaaccagga cgccagccac cagcaggcca agggtgatgg ggctacaaag tgggcctgga   31440
aaacacacat gtgacatgtg ttcaacacgg aacatttttc tgcatgagac acgcagaaaa   31500
atacaaggag cgaaaaattc aactggaagc cccacctccc agagaatacc accatttgta   31560
tttcgatgta atgtattttt cctcaagtat ttttttttt tttttttttt tttttttgag    31620
acagagtctt gctctgtcac ccaggccgga gtgcagtggt gcattctcag cttactgcaa   31680
cttccgcctc ctgggttcaa gggattctcg ttcttagcct cccgagtagc tgggactaca   31740
ggcatgtgcc accatgcctg gctaattttt gtatctttag tagagagagg gttttatcat   31800
gttggccagg ctggtctcaa actcctggcc tcaagcaatc cgcccacctt ggcctcccaa   31860
agtgctggga ttacaggcct gagccaccat gtccggccat cgtctagtct ttgtaagcac   31920
tttaaacatt attgaaatca ttttattata aaatttcatg tcccacattc aaattttaa    31980
gaagtagaca ttttcatgc ctggtaatga gtcttttact atttatttt aaaactttta     32040
atttcacaag aaatagctga atatatttc attgtaagac atttaaatat aggattagag    32100
tgctccctga catctttgct ccttcacaga attaatcacc actgataatt tagtaacttt   32160
ctctttccat gcctatgtaa ttttttatata tacatatagg gtttgttcgt ttgtttgttt   32220
gttttgacac agagtctcgc tctgtcacac acagtctcgc tctgtcgccc aggctggagt   32280
gcagtggcgc aatcttggct cactgcaacc tccgccttct gggttcaagc gattctcctg   32340
cctcagcctc tcaagtagct gggattacag gcgtccgccg tcatgcctgg ctaattttg    32400
tatttttagt agagacgggg tttcaccacg ttggccagga tggtctcaat ctcctggcct   32460
caagtgatcc acccgcctca gcctcccaaa gtgctgggat tacaggtgtg agctaccgca   32520
actggcctta aatacatata gttttaaaaa atatatagag tggattatac tgtacaaatt   32580
gttcttttgt acctttattt tttcaacgtg ccttttttcc ttcacttagt caatgtgttc   32640
tttcttccag cagagtaaca tctgacagca tggatgtacc atgagttact tgtcatcagt   32700
gggccttttg attgtttcct gtgttttact tttacaaata actctgcaga aaacaacctg   32760
tatatttcct tacaaaggca ccttcctgag gtaaatactg agaacgggaa ctactaaacc   32820
acagactttg cccattttaa attgtgacag atgctgtcaa atgcctccct aaaaggcggc   32880
actgacttcc gtccccaccc accaatagtg caccttgctg acccttgata tcatcaaaat   32940
gttttagttt ttgccagtca agtgggggaaa aatgttattt cacttaaatt ccctaatttc   33000
ttataagctt tggcctattt tcatatattg ggaacttgta tgattttcct tctacgagtt   33060
gactatctgt tcctttgtcc attttgtgtg ctatttaaac agcagacttt acactatcaa   33120
```

```
tgtcccaaat cctcctctga caccctt cag gccctgtgg ctggtccctt gagtagctga   33180
ggggcagagc agggcccatg ggtgaaaggg caaggctgca gatttgggct tgaggttcgg   33240
aaaattggaa agcattgtgg atgtcaagga agagagagaa ttttactga atacatatgt   33300 gctaagtaca tactaaatgc aaactcccat cttgtgagga agaaaggtat tggtattttt   33360
aaattattta tttatttatt tatttattta tttttgagac ggagttttgc tgttgttgcc   33420
caggctggag tgcaatggca agatctggac tcaccgcaac ctctgcctcc tgggttcaag   33480
cgattctcct ttctcagcct ccttagtagc tgggattaca ggcatctgtc accacacctg   33540
gctgattttt gtgttttag tagagatggg ttttcaccat gttggccagg ctggtctcga   33600
gctcctgacc ttatgtgatc cacctgcctt ggcctcccaa agtgctggga ttacaggtgt   33660
gagccaccgt gcctggcttg ccattatttt tacctctcat ttcacagttc aaaaaacaaa   33720
aacaacaaga ttcaaagagg ttaaattata taaccaaggt cacccagcta ctaaaaggca   33780
ggaccagggt gtggacacag atcctccgag ttccaagccc ctgtgggtcc cacctcagct   33840
gcatgagggc atgagaggta caggagggaa gggagtgggc tgctacatgg gtggcagccc   33900
actgtcacta gaggggaaca agccaaggct ggatggctgg ggtgtggaga ggagattcat   33960
acacggacag ggaggctgga tgaggggccc ctctgagatg ctgagggcat ctgctgggct   34020
ccctctcacc tcctatttgt tctcccaacc tggatgaacc tcaaaacatg gtgctaagtg   34080
aaagaagcca agcatgaaag accccatggt gtgtgattcc acttctatga gatgccctgg   34140
ggaggcaaat ctgcagaggt agacggtaga ttagtggctg ccaggggctg ggaacagaga   34200
tgagctgtga acaagcacag ggaatcttac tggggtgatg gaaaccttct aaaactagat   34260
tacggtaacg gtcgcccaac ttggtaaatt tacccaaaat cattgaattt gtatgcttaa   34320
aatgggtgaa ctttgcggta tgcaaattat atctcaacta aggtgttttt tttttttttt   34380
tttgagacag gtcttgctc tgtcgcccag gctggagtgc aatggcgtga tctcggctca   34440
ccacaacctc cgcctcctgg gttcaagcga ttctccttcc tcagcctcct aagtcgttgg   34500
gattacaggt gcccaccaca atgcccagct aattttgta tttttagtgg agacggggtt   34560
tcgccatgtt gatcaggctg gtctcgaact cctgacctca ggttatccac cagctttggc   34620
ctcccaaagt gctgggatta taggtgtgag ccaccatgcc tagctcaact aagttttaa   34680 aaactgtaat ggaggtgggt gcaggtcaca ggatgtaca gggcggcacg gctccttcct   34740
gaggagaggt catggttaag accactgtgg aggccagcaa tgtagctaca ggtctcctct   34800
ggagcactgt ctcccatcca aaatttgact ctccgggaaa agctgctgct gcaaataacg   34860
tgcttgggta aggggccatt tgccagagcc acaccaacga cacccccagc ccagccttcc   34920
tcatcttacc ggggcctcag ggtctcctga gctctggatc tgcactctgc tcctgagtct   34980
atggtttaga aatggtcccc cagcacctaa gggtgttgtc ttaggaacag acctaagcct   35040
caaggggcag tgccttctca gtgacccat gggtttcatt catgataaca ggctttgagg   35100
tctgtgtgga cgccccacaa gctctgagtg cctggtgtat aatagcatct catttagccc   35160
tgcatccccc attttacaga caaggaaact gaggttcata gaggctgaat cacctattca   35220
gtgtctcata gtacaggcag tggtagacag agattcagac ctaggcctga ctgacttgcc   35280
actaggctac actgacccag ggccactctc ctcagtgtaa cctccaccta cttttcccac   35340
acccatcccc agccttactc cactaggtca ccttcacaca catccgggtt attcttaata   35400
acctattaat gtttggtttg cattttgccc tgggaattta ctgagggtta gtacaagaaa   35460
```

```
tgatgcaaga ggccaggcgt agtggctcac gcctgtaatc ccagcacttt gggaggccaa   35520
ggcaggtgga tcacctgaag tcaggagctc aagaccagct tggccaacat ggtgaaaccc   35580
tgcctctact aaaaatataa aaattagcca gcgtggtgg tgggcacctg taatcccagc    35640
tactctggag gctgaggcag gagaatcact tgaacctggg aggcggaggt tgcaatgagc   35700
tgagatcacg ccactgcact ccagcctggg caacacagtg agactccatt tcaaaaaaaa   35760
aaaaaaagaa agaaagaaaa gaaattatgc aagaaatctg aagacctttg tttttgccat   35820
catttataaa agtatgactg agtttgccgt cattcagctg tccttacatg aagatgaatg   35880
ggcagattgc ttctcgaatt tagtgctagg atgaaggttt cttcttttgg tggcaggttg   35940 tttcttttcta tcactggggt tggggtgcca tacaacttgg ggtcttccct ttgtttaaac  36000
tgatgttgcc gggttctcca cagccgtagc acacaaccgg ttcttgcgcc ctcatcttag   36060
tggctctatt gtatttgcct tttatatcct ttttatggta gtctgcctga aatcgtttag   36120 gtgaagggt cagggcatgg gactttataa aataaggtta ctcttaagct ccttaagact    36180
ttactcttct gtacattggt tctgattttc tttttactgt gacctcatgt gacggcagct    36240
tcccaccctg gtctcccaga tcctattcag tgccgtcctc aataatttct ggtgcttaaa    36300
atatttaaga caaagcaaac tgagcagtgc gaggcagtgc tccaggggct gcttgtggtt    36360
tgttttctgg gtagcagcag atggcacttt ctgtttgtca ccagtgactt ttgctgggct    36420
gaggtcagta ttttttccaga aacacgtttg ggctgatggg tttaaggaaa acgtgtgcat   36480
gggcatgtgt gtctgtgtgt gtgtgtatgt ggcatacact ccagctgagg tgtctggtgt    36540
agcatagaga agcaaatgtg ttcatttgca aacaaacatg tattcatgaa ctagcacata    36600
ctgtgtatta ggtcctctgt taggtattaa aactggaaac ttttttttga gacagggtct    36660
ggctctatca cccaggctgg agtgcagtgg caggatctca gctcacttca atctccacct    36720
cccaggctca aggcatccac ctcagcctcc tgagtagctg ggactacagg catgtgccac    36780
cacgcccagc taattttttt acattttcgt agagacagag tttcaccgtg ttgcccaggc    36840
tggtctctaa ctcctgagct caaggcgatc cacccatctg ggcctcccaa agtgctggga    36900
ttacaggtgt gagccaccac atctggccaa aactggaaaa gtttaaagtg ctggtccttt    36960
gagtggattt tttgtttgtt aacagcttta ttgagttata atttacgtat aaagtcccct    37020
tgtttaaagt gtacaatgtc atggttttta gtgtattcat ggagttgtgc aaccattatc    37080
ataatgtaat ttcagaacat ttaaattccc ctaaaaagaa accttatacc cattaggaat    37140
cactccccat ttcttttccca gcccccagc cttaggcagc aaccaatcta cattctgtct    37200
ctacagagga tcatatgctg gatattccat aatcatggaa tcatatagta tatggatttt    37260
tgtgactggc tccttttcatt ttattcttta ttatggccaa acaatattcc acgataataa   37320
ataagccaca ttttgttaat cagctcatta gctggtggat gtttgggtag tttctgcttt    37380
tggctagtat gaataatgaa gctatggaca tttgtgtgca ggggtgtggg tggagatctc    37440
ctccattaag ctttgtccag taacaattta tgagtctgtc tcccacgaga ctgtgagttg    37500
ctggcacact cagcatcctt tctgacccta gcttaggccg gggagatagg ctctagagtt    37560
gacacttgga aagtgcctgg ggaaggaagg aggggaggga ggggagggcaa ggggatgtct  37620 gccttgtttc tgagggtgca gagggatagg gaactcaccc ttctgggtct ctggcctggg    37680
taaccggcac actctcttct tgagggtgga cttcttggtg ggctgggcag tggtgggaag    37740
gaaatcaact acagaaagaa agcaagacac atatcttagc caagtgaaca ccacgtggac   37800
tcaaagacaa aactttgtct tatggcgggt gcggtggctc atgcctggaa tcccaacact    37860
```

```
tccggaggcc aaggcaggag atcatttgag ctcaggaggt tgagaccagc ctgggcaaca    37920
tggtgaaacc ccctctctac aaaaaataaa aagtttagcc aggcgtggtg gcatatgcct    37980
acagtcccag ctacccagga ggctgaggtg agaggatcac ctgagcttgg gaagtcaagg    38040
ctgaagtgag ccatgatcat gcaactgcac tctggcctgg acgacagagc aagaccctgt    38100
ctcaagagca aataaatgaa caaatgaaca aaatttgtct tacatccaag tactgaagtc    38160
cttatgactg ttccccaggc tgctacaggg cttgaaggtc acagagcaat agaatgtttg    38220
atctgctttc tgaattctca gatgttggga aaggggtgag ggcctagaga tggggttcag    38280
cttggtgtcc tggagagagg aaggctctgg agccacacag aactgagcag agcctacacc    38340
tctgatttat ttatttttat ttatttattt atttatttat tttttgagac aaagtctcgc    38400
tctgtagccc aggctggagg gcagtggcac gatctcggct cactgcaacc tttgcctccc    38460
aggttcaagc aattatcctg cctcagcctc cagagtagct gggattacag gcacgtacca    38520
ctgcattcgt cgtgccactg cattcgtcgt gccactgcat tcgtctaatt ttttgtattt    38580
ttagtagaga cggggtttca ccatgttggc caggctggtc ttgaactcct gatctcaggt    38640
aatccactca cctcggcctc caaaagtgct agtattacag gtacgagcca ccgcacccgg    38700
ccgacctaca cccctgatta accgctgtgt gacttgggac aagtcatagc attttctgt     38760 gccttgattt cctatctgc tgaaataatg ataactgcca cctccttctt gggattatct     38820
gagaatgaaa gggacagtgt gtccaaaaaa agtttcagta gatgtggctc cacctggctg    38880
aagaccttga gccccagggc tggatcgccc agcctttggc acaacgagcc cctccgccca    38940
actcggcatt ccctaagcac atggaggaag ctcatggaag gaggggtgc ccttttctgc     39000 atgtagagta ccacacaggt gtcatatttg gggattggtt ttccttctca gatggcccta    39060
aaatatatat ataataccag agctaaggga agttcagtct caaactttaa tttcaaaggt    39120
gaacgccaga gatgagggga gctggcccct gcagccccaa gtggtgagtg ctgtgttggg    39180
accccaaacc cctgtcctga ctcctggatg ggtcacccct ctccttcatt tttacccagt    39240 gaccctgct gaagtgttgg gaggggcagt gggccagcac ccagagcaaa ggaagacagc     39300
tgtggctctg atgcctactg gggatgaagg gggcactgct ggccacagag tccaacccctt   39360 gcctttgtgg gttaaggaaa cagatctctc tgcactgatt ttctccaaaa tggtaggaga    39420
gggagtaagg agacaccatg aacctaaact ctagagtcag ggggacagaa aaaaaaaaa     39480 gaaaagaaaa gaaatattaa ggctgggcgc ggtgactcac gcctgtaatc ccagcacttt    39540
gggaggccga ggcaggcaga tcacctgagg tcaggagtcc aagaccagcc tggccaacat    39600
ggcaaaaccc tgtgcctact aaaaatacaa aaattagttg ggcgtggtgg cacgtgcctg    39660
taatcccagc tactcaggag gctgaggcag cagagtcgtt tgaacctgtg aggcagaggt    39720
tgcagtcagc caagatcctg ccactaaact ccagcctggg tgacagtgac tccgtctcaa    39780
aaaaaaaaaa ggttttgggg ggttgtaagg gggaacaggc aggggaagcc cacagatcag    39840
tcattttggg gctggcatct tctatataaa agtagacatt ttaaccccctc acctctctga   39900 gcctcctctg gaaagcggag agaacacgat ctgtttgtct gcttcaagac attgatggga    39960
agaagcaact aggatgaaag tgcactaagc tccaaccatg tgtggggagc agtgctgagc    40020
ctttcagcat aagtttactg gacacaacaa cttttggggc aggcactgtt gtccccattt    40080
tatccaggag gaagcctagg ctcagagagc tgaaataatg tgtccaaagt tagacagcca    40140
ctggctgcag agccagtatc tgcaccaaaa gaccttgatt ctagaacctg tgcttctcgt    40200
```

```
tctgccacac tacctcacgt gcaaagattt tctgacaaaa gttgaacact ttaggtccac   40260
ccaaggccct gggtcatcat agtgctgagg gcaactattg taagaggaaa ctgtcatcag   40320
cagggtcgga gagcgtgcaa cgagcctggc cctctcctgg gagtgttgcc tccttcaatc   40380
ctcatggccc tagaagtagt tctgtttgac ttattttcta cccgaggaag cagggacgtc   40440
tttcagatgg tcagtggtga gcccagaggg gagccaactc tttgggccct cagtgccttg   40500
gctgggcacc gccgcctggg tctagtggga gactcaggtt gggggactgt tctgttttaa   40560
attcttcttg cctagagcca ggtccccctg gattcctcct gagcacccag tttaatctct   40620
ccctctctgt tcttaaaagg aataaaactt cgagcccatg atatacttaa gggcctgaaa   40680
aaggccctgt cttccccaa acactttctc aaccatccca gctttgtcct ctaaaaggcc   40740
tttcttgggt gagaaggtgg ggttcggctc cgaagaaggt ctggttgcaa gccctgggga   40800
gaagcaggtt tggctgcaag ccagagctgg agagaggcat tgacattcct atagtgctgg   40860 gagggggtttg gggtttggaa acacggaagt caggagtgag tgcggttggg atggaggcgg   40920
tgggaagctc tggaaactag ctgtgtttat tgtaccctcc accttctcag actctgaaat   40980
ctcatgagtg gaaggtgtg gggcttacag agacaaaaac aataagctaa agccaaaccc   41040 caaccccaa accccaaact cccaaagtcc atttttcaat acgaaaatca gtggaccccc   41100
acgtgaaggg atgcctcagc ttcttgcctg caatacaccc tcccaggcta gcaagaggtg   41160
gcggggcatc acttttggttt gtgtcttcct aattgtgctg ctgtcccag ctgccccctgc   41220 acttcctcac gctgagtggt ctaatttctg ggtccccttg tggcttttag tgccctcaag   41280
tgagcaggaa gcagggcagt gggagccctg gaggggttg gctccagcct tgggccaagc   41340
tggaggtggg gctagagcca gagccaggct gtgagagtta ccacccataa ctaaatgcct   41400
tctgtccaat atgccacagg tgctgctgag cacatgaaat gtggccagtc tgaatcgaga   41460
tgagccatat gttttatgta aaatgctcat cgaacactta gtatgaaaaa tgaatgtaaa   41520
atatttcagc aatacttttt atattgatta catgttgaga tgaaaatata gttaataaat   41580
tgagttaaat ataacattat ttaaattaat tttacttgct tcttttgct tttttaaaca   41640 agactttaaa aatttagaat ttcatctgtg gcttgaaatg tgcgtctgct ggacttgctg   41700
acttaagtca gaggtctgca gcttctctgg gattaagtgg gtcatggagg ccatcagcac   41760
ccccgtgtga cacagaagag aacactgagg cccaggggag aaagcatggc aagtttgcaa   41820
gcagagctgg gcctggctca gtctccttac taacttcgac tcaggtatga attcgagctg   41880
taggccctca cagagaacat aagggcacct gccctagaa atgccctcac tgggtatatc   41940
agggcagtga gggcctcctt tccctgtgtg cacactctgg ggatttctaa caccactata   42000
aggccaaggg gctcagccca atccagccgt agctttgaat gtccctgatg tggcctgaag   42060
gacagcactg ccctgtcccc ataagaagaa taatgcctgg ccaggcatgg tggctcacgc   42120
ctgtaatcct agcgctttgg gaggctaagg tgggtggatc acttgaggtc aggagttcaa   42180
gacccacctg gccaacatgg tgaaatctcg tctccactaa aaatacaaaa aattagccag   42240
gtgtggtggc tcatgcctgt aatcccagct actcgggaag ctgaggcagg agaatcactt   42300
gaacccggga agcagaggct gcagtgagcc aagatcgcac cactgcaccc cagcctgggc   42360
aacacagtga ggctctgtct caaaaaaaat aataataata aataaataaa aagagaagc   42420 acaatgctca tctctgactc tggcccgtct cttctagttt catcttattc ccacctaaag   42480
tggttaggta atagacctac cttccagggt ggttggcagc attaagcaag ctaactatgt   42540
aaacacttgg aggggcttgg cctgggtaag tctccacatg ttctttctgt tactattagc   42600
```

```
agcagtgcca ttagtcacgg ctgcagagtg gggcacactg aagcctggtg gtcccagtgc   42660
ctggcacgtg cctggcacac aatcggtgct cactgatagc attgagcctg cttcttaccc   42720
acactcagct gagttccctt cccgaaggtc agctcggggc tcccgacgat catgcagaag   42780
tagatgccac tgtcttccgg cttcacgctt gtgagattga aatgaaccg gcttgcatcc   42840 cgaaacacag ctatcttctc ctgttccacc tcttcaccgt ggatagtccc ttttgcggaa   42900
tcccagaggg ccaggaactc gtggtgactg tcactgctcg gtgcctggcg ctgtctcagc   42960
cagtagatgc gcatgttact gagggagatt ttagcctcgc aggacagcat caccatcttg   43020
ttggtttgca cctttatgta tgcagggtc tgctggagga ctgagttgcc atggagaact    43080
aggaaaagcc aagaacagag acatcacaca ttttcctagc cacagctgtg ggaccttgca   43140
gtcacactga gtcaagtgtc aaaggaaaag ccatggaagg acctgcccag ttactgggtc   43200
cagggagtgt gttgagcgca gctgttggct cctggactca gagttcacat accccacctc   43260
ccaggagatc atctgaagg gaggtgttg ctaagttcag ctttacaaag gtacagggga    43320
gagagctgcc atttgtttat tgtgtactta tatgcctggc ccttgcataa aggaactcaa   43380
tcaagcctca aactggcttt ggaattttt aaaagacatg gggtcttgtt atgttgccca    43440
ggttggagtg gagtggctac tcacaggcac tatcatagta cacttcagcc ttgacctcct   43500
gggctcaatc tatcttccca cctcagcctc ccaagtagct gagagtatag gcatgtacca   43560
ccacaaaagg atagatccag gatttttaat cctcattaca cagatgagga aactgaggca   43620
tgaagttact tgttcaaagt cccacttaca gtatgtaagt ggcctaggag tcaaactcaa   43680
ggatttgaag tctgaagcca aagctggttg cctttcacct cccctggctg ccactggatg   43740
tacagccctt cggtaggctc caaactgccg aaggagaccc aggacaggct gggagaggag   43800
cccagaatca cagcagagca tgtggctggt ctgtccgttg ctggacagac cctggtaggt   43860
acaattacag cccatgaccc ccgagcccag caactgatgg gtcactggat ccctattccc   43920
cagtggaagg acagacacca cagaagcagg gctgggagtt catcttagac tctgacgaga   43980
agcacccggc aagcaggggc ttattcatga ggagctagag caggactcac agacctggcc   44040
ctgaacccag cctctggccg tgccagctgt gagacctcag gccagtcacc gagcctctgt   44100
cttcttatga acggaggaca gcttggggct gttgtcctgc ctgcctctga gggttggaaa   44160
taaatgaaat gctgtccaaa aaagcacact gtaaactgta tggccatgta cacaggtaaa   44220
tactgtccct gtgtctcata tcacagggtt gttactggag gtaaattaaa tctcaaggag   44280
aaggatcaga acaggttcca tacacaccaa ggctgcacag cttccaacaa acacaatctg   44340
acctggtgag cccttcattt tggctgtgga gcaagggag acattgcagg ccagggcaga    44400
gatgcaggag ttgggaggca cagagaggac acagacctgg gtaggcagag ggggccagag   44460
ggcatgtgtg tgtgcccaag aggagccagc ttactgagca cctcatgttt aaaatcctgc   44520
ctgcacttgc agctcaggct ccgtggcccc ataatggcct tctccaacac tgatgaaatg   44580
aacttcgact ttttgacttc gctcctggac cactcttagc tttcgctcgc atcaagaatg   44640
aaatgatggg gccgggtgtg gtggctcatg tttgtaatca cagcactttg ggagatcgag   44700
gcaggaggat cacttgggct caggatatcg agaccagcct gggcaacata gtgagacctt   44760
gtctctacta agaatacaaa aattatccag gcatgatggc gcgtgcctct aatcccagct   44820
actagggagg ctgaggcagg agaatcgctt gaacccggga ggcggagatt gcagtgagcc   44880
aagattgcgc cactgcactc cagcctgggc gacagagcaa gactccatct tggaaaagaa   44940
```

```
aaaattatta aaaataaaa ataaaaataa aacaagaag gaaatgatgc ctggggcaca    45000
agtggctgct ggacttcctc ttgtttcccc aaacaccaca ctgcggttcc agcagagcag    45060 aggttttttcc ttgctttggg tcactcactt cttggggggag ttaataagaa ccaataatgc   45120
cagtttattg agctgtgcct ggcatggcgc atacattatc tcatttgatc ctcaccaaat    45180
cctgtggggg agatactgtt ttgcacctac tttacccatg aggaaagaga gactcaggag    45240
ggttaaagat gtgctcaagg tcacacagtg atccagatta aaacccagct tgtgggaccc    45300
caaaacctga ctttgaacca ctgaattgaa gaaacctgca atcctctccc tgatggtggt    45360
tatgtgctca cgagcacaca gtggggctgc aagtacacag gtgcccgaag cccttccggg    45420
aaaacccaga agcgactcct gtaagagcaa ggcctgggct gtgagtgtgc atttcctctc    45480
ctggctgaga cacaccccgg ctcttcccgg ggcccacttg cttttttgtcc cctaggaact    45540 gaatactccg ggctgtggcc aaggccctgc tgtgtgctgg acatggagcc aggcctcact    45600
gcatgttccc ctcggtaacc caggaattcc attctcagag ggacctgatg tttctagatc    45660
catcagtaat gactttagtg ctctgaacgg cctgggctgt ttctatttat gatgttgcac    45720
tcactgggcc agaaccccccg gcgggcaggc cttgtcaccc cctggcaaga tgaccagctt    45780
tgggcttttt gggcacgaga gcaaatcgac cagtttggg agttttccgg gtgtgtggag     45840
gcttcttcca aaaggcagtc tggctgggct tattcagaag gacaatccag atgcccatc     45900 caactccaac aacccaacct ccaggctgct tcctagggag ccacgctacc catgacaccc    45960
aacaccagcg acatcaggga gaacgggagc cagagggatc accctgccct agccctccga    46020
gaactgagaa cgcccgatgt ttgtctgatt gtactacaaa cacttccccg gaagtaataa    46080
aaatgtgtcc acaggaccca tggcctggcc aaccttcctc cgagcacatc ctgcggggac    46140
cctgggcagg gacctgtttc cttccccctgg tgacctccag cgaccctctc tttccttccc    46200
tcactcgctc ccctttttcac tgcctccccct tctcctgcgt ccaggctttt gaggggaggt    46260
ggcctcagtc caggggctct ccggtccccc ggggtaatgc gatatggggg tattttattt    46320
ccacccttag ggaccgtgcc tgccaagctg cctcccgggc gccccgccac cgcgggctcg    46380
acgctgcacc ctgccaggac cagggccagg acagccactt atcacctccc cgctcaggcc    46440
ccgggagcgc agacccttgg gtagcccgcg cgccgccgcc ttacctgtca gctgcgcggc    46500
caagaggagc cacagccgcg gccgcatcgt ggcgcgcccg ggacacctgg ccccgggggc    46560
tcggcggaga cagtcgcggc tggggt                                         46586
```

<210> SEQ ID NO 2
<211> LENGTH: 23791
<212> TYPE: DNA
<213> ORGANISM: Homo sapiens

<400> SEQUENCE: 2

```
cggatgctgt ttacccatta aagaggatgc tacaaatgtt tattcattaa agccactcat      60
aacagcatag tacaaccta tttaaaaaag aaagacatat tttacatgta tgtgtagaaa      120
ataatcagga agaatgtaca ccatattaac aggagattat tcctaaggtg aagaattatg     180
agtggtcttt atttccttat ctacttaagt ttttctctc caatgggcag gcattgcttg     240
taccatacct taagcaagga agtgcatgtt tgggacagca gtttgggctc tcagcctcct     300
taagagagtc aggtctgcct catccctgta tctgctagtt gagcagaggc cagggctgtg     360
tgaggggctc tccaacaatt gtctttacaa agtataaaaa gtcatcagtg atcccaggaa     420
catgtttgta tctcaaattc agagattcaa gagggccctta gtttaacctc actgatgctc    480
```

```
aaattctatt tgtaaagggg tagcctgtcc tctttcatgg gcccctctgc aatgcaaggg    540
ctgggagagc aattccgcct ccacataggg gtttcacaga gattttcttt agagatagag    600
ggattcattt tccagggtta agctcaccac ttcattttat tttaggtcta tacaattta    660 ggcttgatta taaaaaaaaa aagtctgata ttgtttacat tatagaactc tgccaaaggc    720
agttctcttc tttaattcat tacctcctcg aggctctggg cacagtatcc caggtatcaa    780
gaagtacttg ttcccttgcc gttggagact caagcacctc accctgagac aggggcctcg    840
gaaagaaaga cctgaatggt gtggaggaaa gagccctgag ctgggagaca aggtccctcc    900
agctactgct ccaaccctga cttgctgtgt gcctttgatc aagctgtctc tgggctttag    960
cctccccctt tgtaaaacgg gcggggaaga ggttgagatg gcatgggtgc ctccagctct   1020
ctcagcatga ttctgagaac tctgcgggta gctctggcct gccccttttcc acgccctacc   1080 gcgatgtgcg cacaacagta ttgtgaccct tgtggtgtac tgtagatttt acctagtttt   1140
gtttcccgtc aaacacataa agaaaaagta atctttccca ccccgccccc actaaaataa   1200
taatcatgag aatgaataca cagggaggaa gactggaaaa aatgaaaggg aaggacttgc   1260
tccctcaaaa ggaaggatct cagtttgaag taatgtagtg gctgttgcac agggttagac   1320
gtatctcgcc gaaaggctgg gcttgtctcc cgatttgacc acaggcctga aagagaggaa   1380
agcgaccatc attgtagcca gaaccccgcc agtgcagcat ccatccagcc acgtccagcc   1440
tcccaatccc ccagcctttg aaaggtctga gaacctgttc ctggggcacc agcatgggac   1500
tgggtgaatg acgtcagcac agcacccgtg ctaaatgcct tacttgcacc atctcatgta   1560
atcctcacag cagccttaag ggtgggcact gagattgaga agttaaactt gcccaaggtc   1620
acacatctag gaggtggctg agccaggatc taaaccgagt tagtctagct tcctggagcc   1680
cctgtcaagg tctccacaga ggtgtgagag tgagactgat aaccaaagtc attagctgac   1740
ctgattctca gccccggagg atgacaggga gagaggagga tgtgagcaaa tcaccaccat   1800
cagccaaatg atgttacgct aaaaacgtgt taattcagca ccaggctagc accttgtaaa   1860
catgctaatt catcatgagc gtcatgtctg cactctcagc cctctaaaac ctctctgttg   1920
aagctgagcg gcccaccatc atcactgagt atattaactc gggtgttgga atttcccagg   1980
tgtgtttaat ctgtatagct ttgtatttta aggcagaact ttattctcag ttattcatct   2040
caaaatgaga gttttcagaa aagatcgaga aagggatgg tccttctgca aaagttccaa    2100
agtgcaccct gaataataaa aatgctaaaa actggccggg tgcggtagct cacgcctata   2160
atcccagcac tttgggaggc caaggcgggc ggatcacgag gtcaggagat cgagaccatc   2220
ctggctaaca cggtgaaacc ccgtctctac taaaaataca aaaaattagc cgggtgttgt   2280
ggcgggtgcc tgtagtccca gctacttggg aggttgaggc aggagaatgg cgtgaacccg   2340
ggaggcggag cttgcagtga gccgagatcg caccactgca ctcaagcctg gcgacatag   2400 cgagactccg tctcaaaaaa aaaaaaaaa aaaagaaaa gaaagaaaaa gaaaagctaa   2460
aaacttcccc ccccactttt tttttttttt tttgtgagat ggaatcttgc tctgttaccc   2520
aggctggagt gcagtggtac gatctcagct cactgcaacc tccgcctccc acgttcaagc   2580
gattctcctg cctcagcctc ctgagtagcc cggattatag gcatgcacca caatacccgg   2640
ctcatttcta aagtctttat cccttggta tatcacctgt aacatatgca ttggaaatcc   2700
attgcatttc cattgctaaa aacaacaatg tgtaaagtcc tgaacttgga ttccctcaga   2760
aaaatgtaaa ggagtataaa atgcaaactc caggtataaa atgtaaaata tttcatctac   2820
```

```
tgaaaagaac tggtgtacac agtcggttat ccttaacact tcagcctgca gccatgggga    2880
aggtgtctga gctttggatg gaagttgcag ctcccgggca gtatgacctt ggacaaatca    2940
ctaaatgttc taagcctcag tttccttatc tgtaaaatgc aggtaatcat gactacttta    3000
aaagttgtca taaaacttaa aattaaaaaa aatctataaa gcaagtaacg tgcgttgtag    3060
gctttcatca aatggttatt actattgata atctgagttt aatgtgcctt tgccacttta    3120
ctaatccctg agccatgaga tggcacaaag ttgctgtgag gattaagaga gatggggagt    3180 attacccct a tcacagtgcc tgactagagc aggcacttgt tagatgctac cacagggatg    3240
cctcagccaa cgggtggaga gaggttttta acagagaggg agagagagag agagtgtgtg    3300
tgtgtgtgtg tgtgtgtgtg tgatcatggg ctgaaactgg atgaggcagt cacttgagct    3360
gccagatagc caattgtccc tgcatctcgt tcccctttt t tctactccag tccttggcag    3420
caaaccaagg tcctacatga cacagagaag ttagcaacca aagccattat tattttggtt    3480
cagctgataa aagattggct ctccctcaaa aactagacc agccaagtag gaaaaaaat    3540 tgttttctta agaaaacaac aaaacccaga tggaataatc agaataaaga ggaggtcagg    3600
tcctacgagg agctaggata aattgggga atccctcagg tttttttttt tttttttgg    3660 aagtgccagg tcaataaga tggagattta ctggagtcac actgctgttg gcacccgcct    3720
aacccgggcc tccttttct caaagacaca ggccagatgc cagccttggc ctctctttgc    3780
tcaggaactg gctgactccc tgccccagga tttcacggcc atgacctctc tctgggaaaa    3840
gttcccacta tttgctgctg gggaaaccag gaccccaccc cagggctggc caaggtgagc    3900
aggctgagtt caaagagac tcaccgggga catttgcaaa cacgtcttcg gttccctgga    3960
taaggaaaaa gaagggaaaa agtgagtgcc cctatccatc aatagtcccc aaagacagtg    4020
tattttttgt tgttgctgtt gttgttgctg ctgttttttg gttttacaaa aaatcatttc    4080
agaacgatca tgggctgaaa ttggatgagg caaatagga attgcctcta cgaattctcc    4140 ttccttccc ctatttcttt gaggattata actcttgaga gccgggtaag ggcttcttat    4200
ccatccttcg tctcaagcat caattaaaaa aaattgcaac tacagacgcg ggcgaaagcg    4260
gggagcctgc agacctgatc cggcacctct cttgcatggg acccaaagca gggtgggcgg    4320
ttcgccgaag agggccaagg acgaacctca aactgatggt ggttttgact aaccctcctg    4380
ggcacttgac tcggccacag cggccccctc ccggcgggcg tttgtcatgt gtccagacat    4440
gtgcgcgcgc gctgcgggct tcgtcgacgg aacacacccg ctgcagcggc tctgggaacg    4500
cggctttgtc tcccaaaacc tctccgagag cgcaaggagc gggaagggct ttctcgcatt    4560
ctatctccca gaaagaagtg cctgtacctg cggggcagct cgggagtccc agaaaactca    4620
accccaagct cccccctcgc aaggtccgcc tggagctagc agagccaagg gcaggagcgg    4680
ggccgactcc ttcccgccgc gattcctcgg gacttactgt ggttgcagta aagggtgata    4740
accagtgaca ggagaaggac cccacaagtc ccggccaagg gcgcccagat gtagatatca    4800
caggcgaagt ccagcccct cgtgtgcact gacgacacca aagacgccga catttaggag    4860
agggcccggg acctcccaac cgccccaccg tcccgggaac gtctctccgc ctcagatctc    4920
ggtttcccac cacttggaca gcccttgact ctacctacag tatcagggct gtccctggca    4980
tgggctctcc ccgcggtgcg tgccgccccc gccccgggcc cccgcacgcc tcacctgcgc    5040
cccccgccgc tggccggcac gcctctgggc gcagggacag gggctgcgac gcgatggtgg    5100 gcgcggtgt tggtggtcgc ggcgctgcg tcgtggtggg cttcgctgca agagcaacag    5160
agcgtggttg ggggccaggc tggggttatg gaggcgcccc agccccggcc tcgcgcacct    5220
```

```
ttccccacgg ggacgcctcc ccccggtttt cctgggagaa gggatagcag aggagacagg    5280
atggggaccc cgggatgcgc gcggacccct gtgctcgggc ctcggctcag cccagcgcac    5340
ccggcgccca gagccggagc gcaggagcca gctccctgc  acctggcctc tctcccgggc    5400
tgaaccagca accctggagc gcgggttgat tgctgtccgc attttaccca cgagcaaacg    5460
gaggcgcaga taatttaagt catttgccca gaatcacaca agaatccgaa ctcgagtcca    5520
gatcggccga acgtaaaaag ccatcccag  tccctactca gcctcgcgtt agcctcagtt    5580
tgctgtgtct gtgaaatggg aacagtatct aagtcgcttc caggtgcgct aagaggcttg    5640
aaagcagggc ccaggtgtgg aaaacaggtt gaggtgaacc ccaagcccca cgcggagagg    5700
tgccgcaacc cggcgcgcgg acctggcagg aagaccggca cgaagtggct gaagtacatg    5760
atggagttgc tcaggccga  gcagaaatag tagccctcgt tctctcggcg gaagtcgctc    5820
agggtgagga cgaaggtgtc ccccaacctc ttgcccgaga accgctgggt gtccagcccc    5880
tcggccgcct tgggcttgtt tttgggagagg tataggagga aggtgggact ggcggcggcg    5940
ccgcgcggct ggaagagcca cgagcagccc gacgtcgggt tggacagcag cacctggcac    6000
ttcagctcca ctgtctcgcc caggttccag gtccgatcca gcggcgacac ccggaactgg    6060
ctcggcctgg cggcgtctgc aggcggcaag cagcgaggct gagcccgcag tcccgcgccc    6120 cccgccccc  gcccgcccca tcccctgcct tcccgggcgc tcaaactca  cggagcagca    6180 aggccagcgg caggagcaag gcggtcactg gtaaggccat gacgcgctcc ccaggacgct    6240
gcttggctcg aagctcgggc gcgaggggag gcgcgcggga gccggtgggg cgccgagggg    6300
ggaaagttgc gcccttcggc cggcccggag cctgatttcg catttggagg atgtgatgtc    6360
acccgaagcc cccgccgagg agagtcaccc tccttttcgc ggttgtcgcc ttccagcccg    6420
gcgaggaggc tggggcccgt gaatagggcc gtcgaggcag cctggccagg caactggggg    6480
cagctgaaaa ctgcgggttt ggggatgagg aaaagggctt ggaaatagtc cttggaaatg    6540
gttgtcttgt gagagtgaca gagtgggtga agggagacca aagatttcaa gaagtgaggg    6600
cgagagtagg cagcaaagga ggggagtgtc ccttcctttg ccttcactaa aggcgtctct    6660
tgtactgtca ccttgggact ttttattggc aaaatgggca ctgagggctg aaaaggaaga    6720
ggaactagcg acctgccgc  ttctgaggaa ctcgctagag cagccccagt tttcaccgag    6780
gaaggaccct ctcccttccc ccaggagatt tccatgagag cggcagcagc cgaagctttg    6840
ggtgtcggtg tcagtgcgct gctgacctca ttcttccggc cttcatcca  gcggctaaac    6900 tcaccacaca gcctcatctc ttcttggagc cattgcaaca gccttcaatt cacaccagtc    6960
tctctcctga tcagtcctcc agccacgttg ttataaaaat tattattctc acaaggggga    7020
tctgacagcg tcactgctgc agcctcccat ggcctgcatt gctggatgga aattcaaccc    7080
ccagcttggt tgaccagccc ttgggtgctg gctcctccca gcctccgcac agccccctgc    7140
cctgcctttc ccatacacct gcagctgcag cttcacaggc ttgaagtcat tcaaccctg    7200 cgctctgtgc tttcacgccc ttgcacttgc ggtccctcgg cctggaatgc tggtctgttt    7260
aagccctgga ggcagctcct gtgctgtctc atttggacct catttctttc accccagct   7320 ctgggtgctc tgcagggagg tgtgggtgat gtgggtgaat gctgggtag  aggcggtttt    7380 ctcttttctg tccctaacac atgtgtgtcc ccttcctttt tgtttcttta aaaaataaaa    7440
taaaataaaa aagactggag tctcgctgtt ttgctcaggc tggccttggg actcctgagc    7500
tccagtgatc ctcccacccc agccccctga gtagctggga ctacaggctc atctttcctt    7560
```

```
tttgactgtt gctgtcctga aaccttccag ctccagtggc atgccctctt cccatttctt   7620
cagggtttct gagtctttcc actttgaatc ccatagtggc tgcacctcac attgctactg   7680
cttgatccta gagacaagac acctggcatt ctgtgttcca tgtgtctgcc ccacccatta   7740
gttctgctgg gcgaggacca tgccgagact tcatgatgtg tcctccatcc ccagaaacac   7800
agcatgggct gagctgtgct tgttgaactg cattctcctt gtccttgtga agtacaaact   7860
taagtgttgg atgggttctt tgtcgttgtt gctattttt tttttgagat ggggtctggc    7920
tgtgttgccc aggctggagt gcagtgtggc accacctcgg ctcactgcag cctctacctc   7980
ccaggctcaa gtgatcottc cacctcagcc tcccaagtag ctgggaccac aggagcacac   8040
caccatgccc agctaatttt tgtattttt ggtagagatg gggtttcacc atgttgccca    8100
ggctggtctc caatgcccga ggtcaggcgc tttgccccgc cttggcctcc aaagtgttga   8160
gattacaggt gtgagccacc atatcagggc ctggatgggt ttttttttt ttttttaatt    8220
attttgattt cagtacctcc ttccagctcc ctcaaagcat ccaagatgct tattctagca   8280
tggaacatgt aacattttat attcagaaat ttttaaaaat gtcttttaag tgacaacagt   8340
gcaatatatt cttgtacgaa aacaaacaca aagttccctg tctcaactct cctcactgtc   8400
acctgctccc cacagaaaac cactgttaca gttgaatgtg tcccttagat attatctgta   8460
cataaacaga tgtttataca tcatcttaga cacatgggat tgtatgagat aaatattttt   8520
ttgcaaccta tcttgtttca cagtagaagg agagcgttca gcagatgaag atccaccoca   8580
ttcttataaa tgggtgcatt atatatgggt gttccataat ttaattctgc tgttagtgga   8640
catttaggcg atttctcatt attgcaacac tagcaaggct gtggtagata taatgtatct   8700
gtatcactga gggcttgcac cagtacctgc agcttttttca aatgggagat gagggagttg   8760
gggaagaaaa cacctttaca atgatggtta taactggcct atcgatgtat gcatgtgtgt   8820
gtgtgtgtgc atggtatgag ggtccctcgc tgtgtagaca cagtgctgtc cctcaactca   8880
catgaatgag ggagacaagg aagcaatcaa gtccagacag gccaccaaca catcaattct   8940
tgctgtagat ggtagtttgc cattttgctc agcaccacca gcactgtatc aggagtgtca   9000
aatggccctg ctggccaaag gctacaatca acagggtggt aaggaagatg gctagacacg   9060
aaactgcact tgcccagtgg tggaagcact gagggggcca gagtcaacct ccacctattt   9120
ggatcttgag aatcaggccc ctgagtgtga tgatggccag atttggggt gtactgcttt    9180
aaaatagact agttccatct tagtctcacg gaaatcagct tgggggcctt ctagccctgc   9240
agctcagaaa agtgtcagcc agtggggtgg cagccccttt gtacagagca ccatgggggt   9300
tggggtgggg aggataaggc aacatgtcaa acccatcaag gaggctttgt gaccccagtg   9360
atatttttg cagaacgtgg tggatttcg atgtgaccac aatgacatcc gccttgcagt    9420
ggcagaacag atgcaattgc acaagttctg gagaaacttt ctgtagacca ggtgtgcaga   9480
gggctgggtt gggcctgtcc atcactgcca ggtaagttcc caaacccac actgtagcac    9540
tgacttggga tggcatgaag aaatgtgaat gactgcactc ctttaagcaa gccccttatt   9600
taaaaaaata tccagaagta gatagagtaa gatagtaacc agtttctatg ctgatttaaa   9660
ctggtccatg gaaatggaaa actttaatgt agattaaaga catattcaaa atgcaaaacc   9720
gggcagagca gtggtaggaa atccatcagg gttctgtgcc actgctccta agacatgaac   9780
tgcaggggaca acttggaatc atggctggga aattgcctgc tgtgtcccca tcgccaattc   9840
aggtctatgg agatgttact gttccttgga ggagttagct tgtccagggc tagaaactct   9900
agagttatca gggcttgttt tatcttaatt ggaaatacca atcaatttgg cctcacttct   9960
```

```
gtcacctttc ttttcctcca ccccgagttc cccaagttca tctagctgct gtccttcttt    10020
cctggacttt tgcaatggcc tcttaactgg ccaaccccat ttctgctctg tcccttcta     10080 gagaaaatct catcatgcca acccctgct tcaacctgaa aggacttcct ggtgtcccta    10140
gtagaatgtc ggggatccct aatgttgcct gtgaggccct gcacacttgg tttcatagtc    10200
tctgtcctct tgtctgtcac cttcttcact cctcctaggt tccgcatctc tcatttctca    10260
agcggaccct agtcctttcc acttcagagc cattaaacat gctattccct cagccaagaa    10320
tgttctcacc tctgctctct gcttaccaaa ctcctctccc ttaagaccca gctcaagcat    10380
ctccttcctg tggggtttag ctccttcccc ctcccactcc cagacagtac agaccacatc    10440
cttctcttct ctgtgtcacc cggaccttgg gtatctgcag actggagcac aatggtttgt    10500
ttgcctgtcc agcttgacaa ccaaacccct ggtcccttga ggaaggagcc ttgtccctct    10560
catgtttaca ccagggtgcc aaacagaggg cttggcacac acttgagtgg cacacactca    10620
agaaattctt gctcagtaaa agctaaagga aggtagaagt agggtacagc agaccagagg    10680
aggcttagat agttcattcc aagtaagagt ggtcaggaaa ggcttcacat atagttgggt    10740
ttgaagataa aggaagaatt aggagagagg ttgtttagaa tgaggcattt gatatgtctg    10800
atcaagatca gctgatacca tgctttaaca tatagcaatg gtatagttaa aaacaaaaga    10860
agaggaggaa ggggagaagg cagatgtact caaaagcaag ataaacgtct tcaaggatgt    10920
agttgcagga caatggctgg aatcaggggc tggcttgctg ggatctgttc ttagcaaacc    10980
attcttgggc ctgggtcttg agggtctgtt cttagtgtag aggcaccaag agtttgactc    11040
cttcagctaa cagagtttca cagtgctttg cctatagagg aaggctggag ccaggctctc    11100
tgcttgaaac agggatttgg atctgatttt ctcttgattg aaagagagcc cacagccacc    11160
catgtaaggc ctagttctga ctgtgggccc tggaaagtca gaggctactt taaaaaactc    11220
aggaaaagag agagtaaaga gaggaagaga ttttcaaaaa tttctattca agataaccct    11280
gcacacacac tcgaaattca agtatacat aaaaaagact caacaagtgg aatgtgaatt    11340
cacttccaaa aagaggcaaa ttattgaaca atttgaaaaa tgtttaaaac aaagagaaca    11400
acaaatgtag aaaatgcaga aattaaagaa gaacagttga agatgataaa tactgagcat    11460
actggaaatg aacactctac atattaaaca aggatatact ctaggttgga catagttgaa    11520
gggataatta atgaattgga agctagcatt gagaaattca tagagaatgc aacacaggga    11580
gatgaagaca gaagcagttt gaaaaagctg ttgagatgta tattagcatg gtgaagtgtt    11640
taataggatt tcagaaaggg gagaacaaag ggaatgtgga gaagaaatat gggaagaaag    11700
catggctgaa aattttcac aattaaagac aaacattctc agatcaaaaa tactcttagt    11760
gccaagtata aaaacatata catctttgca catatcaagg tgaattataa acatcaagag    11820
taaagagaag agggcatccc aggaagctag gatgtttgaa atataattgg gagaatcctt    11880
gttgcagttt ggattgggca gagagggtaa gaagctgaac tgtaatgggg aaaaatatac    11940
acattttggt tacaccttgc attgactctc tgtcatcccc tcccttggtg ctgacacatg    12000
cttactgtaa aactgatcca atgatcccat agagttgatg tttgtggttt ctttgaataa    12060
acatataaat tgatccttgc cttcttaaaa cctgagaaag ttacatttgt cttatctgag    12120
ttcctttcta gggaaaccaa ctatcaggcc tcccagatgg tagcaatgag ctgaaactca    12180
ccagatcact tattatgaac aataagacgt cagactcttc acctggtatg atggcctaac    12240
taacctcctg tttcctgttg tccaactcct tttccttact cctcccaact tcctgttttc    12300
```

```
ccacacatga ttacatgtct tccctgctat ataaacccct taattttagt caggtcagag    12360
ggatggattt gagactgatc tcctatctcc ttggctgcag cacctgacta aattcttctt    12420
ccttggcaat acttgttgtc tcagtgattg gctttctgtg aggtgagcag aaggacctag    12480
atggatcccc cggtgtttcg gtaacaaaat tgttttggat ctttaatctc agtaacactg    12540
aaacagaagc gttctgaatg caactggaga gccaggattt gagttcagaa gagggtcag    12600 ggctggggat gtagccttgg gaaggaggtg ataagttgtg agagtgggtg tcattgcaaa    12660
gggaggtggt gtggaaagaa catacagaag agtatatgga accttcaggg aaggctcgta    12720
ttgaagagca ggaaataaaa cattggcaag gaatccaggt agtgcaggaa attcagaatg    12780
gggcttgaga aggtggaaga acttcacagg ggaggtttgg gctataagag aagcacagag    12840
aggacatcaa agcctgtggc aggtagagat tgtaagctca tgtctgcccc tgacccacat    12900
gaggatgtcc cacatgtttg ccattggtgg atgataagat gaggaggact cacaggagaa    12960
aggccaacaa gggagggtag gggcagcatg gggacttgtg gagggcaatg tcagatgaag    13020
tgatgttgac ttctgaactt cattcattat tcactcattt aaatatttct gctattcact    13080 ttttttaaaaa aaagttttga aaacatttta acatagaaca atatgtcaaa taatataaaa    13140
tgcccactct ttataagtgt tagcattttg tcgcattttcc ttcacatgaa cattacagat    13200
aaaactgtac cctcccaagt accaccccac ccgccttctc atgaaaagct aaatttggag    13260
ttttgttcat taattatgac agaaagatgg taagttttt aattttaat ctgttaacct    13320 ttcctatgga gctgagagag aaggatgccg aatgtccaat gagtgtggat ttgtctattt    13380 ctcctttttaa ttcagttcat attttgtctc ctatattttg aagctttgtt attaggtgca    13440
tacacattta gaattgtgcc ttctggatga attcactctt ttatcattat gaaatgttcg    13500 tctttaccte tgcctctggt aatactttgt tgtgaagtct accttttatt cataaggaac    13560
agagctttct ttcttttttt tttttttgag atggagtttc cctcttgttg ctcaggttgg    13620
agtgcaatgg cacgatgttg gctcaccgca acctccacct cccaggttca agctattctc    13680
ctgcctcagc ctcccgagta gctgggatta caggcatgca ccaccacgtc cggctaattt    13740 tgtatttttta gtagagacag gtttctcca tgttggtcag gctggtctcg aactcccaac    13800
ctcaggtgat ccacctgcct cagcctccca aagtgctggg attacaggca tgagccactg    13860
tgcccggcca gaaacacaac tttcttatgc ttcccgtttg cataatgtat cttttccttt    13920 ttctttttt tttttgaggc agagtctagc tctgttgccc aggctgcagt gcagtggtgc    13980
gatctcatct cactgcaacc tttgcctcca gggttcaagc aattctcctg tctcagcctc    14040
ctgagtagct aggactacag gtgcacggca ccatgcccag ctaatttta tatttttagt    14100 agagatgggg tttcactatg ttggccaggc tggttttgaa ctcctgacct caggcaatct    14160
gcccacctgg ccttccaaag tgctgggatt acaggcatga accactgtgc ccagcctgca    14220
taatgtatct ttttctatcc atttactttc aacttcccct tctctgtttt gaatgtttta    14280
ctagatatgt atacatgtat atgtgtatat atatctataa atgctatata atttttatttt    14340 ctgagagttt caaaatacag aaatgtcatc atattgtgtg tctttgagct atgttgatac    14400
atatagattt attttaaatg ctgtgtgtg tattatcctg tgaatgtgcc acagtttcat    14460
gttcagtggt tcttgaacca gagtgttcat ctctctggaa gtatatggag ctgtccttg    14520 gggatacaca taattttaag gaaattgttt tccagattct caactcccat tggttctctt    14580
ctcataaaat ggacctgccc aagaacaagt ccctgtgttt aggctttgtg ctcgttctcc    14640
tttctggcct attctttcat gattatttta tttcccactt taaaactgaa aggcaaactt    14700
```

```
cccgccctcc tgttccttac tatgctccag aggtgggcac gtaatcctct gggccaccaa    14760
taaaaagaca aatccaaaca tttttcatgt aatttccatc cgttagaaat tgccaaagaa    14820
tgcatttctc ctgagcagag tccccagtat ccaggtagag tcatctgggg gccgggcacg    14880
gtggctcacg cttgtaatcc cagcactttg gaaggccgag gtgggcggat cacgaagtca    14940
ggagatcgag accatcctgg ctaacacggt gaaaccccat ctctaccaaa aatacaaaaa    15000
attagccggg cacggtggcg gcgcctgta gtcccagcga ctcggaggc tgcggcagga     15060 gaatggcttg aacccgggaa gtggagcttc cagtgagcca agatcacacc actgcactcc    15120
agcctgggcg acagagcgag actctgtctc aaaaaaaaaa gaaagaaaag agtcatctgg    15180
gagggatgca ggaggcagag tgcctcacag caggctttgg ggcctcatcc ctctactcag    15240
ctctctatca tcgagctaga attcagaggt gagacagtca ttatgaggat gcatattaac    15300
gtgttcatta tgattacaaa aggaatcaga attcttttt ttttttttaa cagaaattaa    15360
gtctgagttg ttaattggtt tgacattgaa gaccagcttt gccaatgagg ttaatggcag    15420
tattttaact ttccttgaat ctagtgagct aaatctttag ctccaaggtt ttgatgagaa    15480
tcaagtttag cgctaaagaa acagcttaga aaagaaaga aagaaaaca cttttaacaa      15540 gtttaaaatc tatgataaga taaaagcatt ttggccaggt gcggtggctc atgcctgtaa    15600
tcccagcact ctgggaggcc gcagtgggtg gatcacaagg tcaggagttt gagactagcc    15660
tggccaacat ggtgaaaccc cgtctctact aaaaatacaa agaaaattta gtcgggcatg    15720
gtggcaagcg cctgtaatcc cagctactca ggaggctgag gcaggagaat tgcttgaacc    15780
caggaggtgg aggtagcagt gagccgagat cacaccactg cactccagcc tgggcgacag    15840
aaaaaaaaaa aaagaaagaa aaaaaagat aaaaacatta tatcacaata ttgtttgtat    15900
tggaatttgt cttgaaatta aattaaaaat atttctaata ccccaacact ttccaagtta    15960
atcaatttca gcaatcgttt ttaagtgaaa gaagaatgat gtcattgatg gctacttggt    16020
aggcttcggt aaaacctagt ttagggcttc caaaacccaa gaaagtgaat aaatctaaaa    16080
atggtaacaa acccatgtgc aggtcagtgg ttcccaagtg tttgctttca acaaaattgg    16140
aagaaggcct tctagatttg gcaactatca caggttgaat tgtgtccccc caagtatatt    16200
tgttgaagtc ttatactcta gcatctcaga atgtgacctt atttggagac aaggtcctta    16260
cagaggtaat caagttcaaa tgaggccaat aggatgggtc ctaatccaat ataactggtg    16320
tccttgtgga aaggggcaat caggacacac acacagagaa catcatctga aaacaaggca    16380
gagatggggt gatgtttcta caagtcaagg aatgccaaag attgccagca actgactaga    16440
agctaggtga gaagcatgga acaaattcct tctgtagccc tcagaaggaa cacacccagc    16500
tgacaccttg atcctgaact tctagcttct agaactgtga ggcaataaat ttcttttgtt    16560
gaagccacct agtttgtggt actttgttaa aacagccctg gcaaactaat acagcaacta    16620
atagatcatt aaaattaatt tttgatgata gataacattg tctccctccc tccctgcctc    16680
cctcccttcc ttccttcctt ccctccttcc cgctctcttt ctctctctct ttttcccttt    16740 ctcccttttct ctctctctct ctctttctcc cttggagaaa gggtcttgca ctttcgccca   16800
ggctggagtg cagtggagtc actgcagcct caacctcctg ggctcaaaca gtcctcccac    16860
ctcagcctcc caagtagctg ggactatggg tgcacaccat catacctggc taaattttg     16920 tagagatggg ggttcaccat gttgcccagg ctggtcttga actcctggac tcaaggaatc    16980
catccatcca ccttggcctc caaaatgctg ggattacaga cgtgagccac tgcacctggt    17040
```

```
tcatgctttt gtcttttga  aaaaaaaagg aaaaagttaa aagatttagt gattctgctg  17100
taacaaagcc aactatttat ttatggagac aaaatttctc agtacttaca ttgtatgaca  17160
aacaaaagca aaacaaaatt aatactgaac tctgtctcat tctagcaatc aataaataaa  17220
ataaatcctg ttatttatg  ggttcattaa ttaattggac cacaaaattc atttgtgggg  17280
ggtccatttc attaagagct gaattttccc ccaaaattat gttttaaaaa gctttttttg  17340
agataattgt agattgacat gcacatacaa gaaagggtac agagaattcc ataccttca   17400 cccagtttcc cctaacaaag gttacttta  tatttattta tttatttta  gagacagagc  17460 attcttctgt tgcccaggct ggagtgcagt ggtgtgatct gggcccactg caacctccgc  17520
ctcctggatt caagtgagtc tcttgcttca gcctccctag tagctgggat tacaggcacc  17580
cgccatcatg tctggctaat ttttgtattt ttagtagaga caggatttca ccatgttagc  17640
caggctggtc tcaaactcct gaactctagt aatctgcctg cctcggcctc ccaaagtgct  17700
gggattacag gtgtgagcca ccatgcctgg ccaaaggtta cttttaatgt tcattaattt  17760
tgaagacttg cagtttattt atgctataaa ggacaattgt gcactattaa tagtcgcaat  17820
gatgacataa tctaagactt ttaatattta gaaacttatg gttgcaggaa attaaaaatt  17880
catctcatgt gcttttttgg cagagaagta tgaaatattg atcaatataa ggtccttaag  17940
catatgcacc tattaaactt ttatggagga agtagaatag aattcataag tccatttgtt  18000
tttactcttt attttttga  gacagagtct cactctgccg cccaggctgg accgcagtgg  18060
cacaatctcc actcactgca acctctgcct ccttggttca agtgattctc gtgtctcagc  18120
cacctgagta gctgggattg ctactcaggt gtgcaccacc acacccgact aattttgta   18180 tttttagtag agatgggatt tcacccctt  ggccaggttg gtcttgaact cttggcctca  18240
agtgatctgc ctgccttggc ttcccaaaat gctgggatta caggtgtgaa ccatcgcgcc  18300
tggcctagaa ttcataagtt taaggagaaa aaggagtgat gaaaaatttc caaaagttaa  18360
gaactttttc ttgtatttta aaaatgagtg acggttgaaa caaaattgat atattattta  18420
tgtgctatta gaaataatta aaaagaataa ggttttcttt tttaaaaatc aacatttact  18480
ttggaaatta tgtcctttat agtgatgaaa atgtttgat  gtcaagttaa aagtgagtaa  18540
agaagtacat tcattttata acagcatttt tcacagtagc taaaatgtgg tagcaaccca  18600
agtgtttatt actggatgaa tagataaaca aaatgtggac tcaggcatct ctcttctggg  18660
ctcataccca aaggaaatga aatcaccacc tcaccaaggt atctgtactc ctgtgtttat  18720
tgtagcatta ttcataataa ccaagatatg gagacaacct agacaaccat caatggacga  18780
atggtttaag aaattgtggt acggatatat acaagggaat tcagccttaa aaaggagga   18840 gatagcattt gccataacct agacgggcct ggaggacatt atgctaaatg aaagaagcca  18900
gacacagaaa aaaatattg  cacgatctta cctgtatgtg aatcttta   tttatttatt  18960 ttcttagacg gagtctcact ctgttgccca cgctggagtg cagtggcgca attttggctc  19020
accgcaacct ctgcctcctg ggttcaagta attctcctgc ctcagcctcc tgagtagctg  19080
ggactacagg cacctgccac cacacctggc taattgtatt tttagtagat atgggttttt  19140
gccatgttgg ccaggctggt ctcaaactcc tgacctcaga tgatccacct gccttggcct  19200
cccaaagtgc tgggattaca ggtgtgagct accatgcctg gcctgtggaa tcttttaaaa  19260
aggtcaaata tatagagaat aaaacagtgg ttatcaagat tggagtagga gagaggaaat  19320
gggcagatgt aggcctaagg atacgaagta gcaaacatat aggatgaaca agtcaaataa  19380
agtacaatat gaagactaca attaataata gcatattatt ccaggatttt tgctagatga  19440
```

```
gcatagttgc ttttgctaca ggaggaaata aatgggtaac taagtgagat gatgcataag   19500
tcaatttgtt tcactatagt atccattcta ctaaatatgt gtgtcttata ccatgatgtt   19560
gtatatacct tatatataca caataaaatt tatttaaaca aacaaaatgt ggtatataca   19620
tagagtggaa tattattcag ccttaaaaag gaagttctga cacatgccac aatatggatg   19680
aatcttgagg atattatgct aagtgaatta agccagtcac aaaaaaccaa atactgtatg   19740
attctatgta tttgaggtat ttaaagtagt caaaataata gagacagaaa gtagaatggt   19800
ggttgggaca ggctggggag agggaggagt gggagttatg tttaacggtt atagagtttt   19860 agttttcta gatgaaaaga gttagagaga aggatggtgg tgaaggttgc acaacaatgt   19920
gcatgaactt aataccactg aactgtacac ttaaatgtta aaatggtaag attgttatgt   19980
gtattttgcc acaataaatt agtattatta ttttttttag agacagagtc tagctctgtc   20040
aaccaggttg agtgcattgg tgtgataaca gctcactgca gcctccaact cttgagcccc   20100
caactcctgg cctcaagcag tcctcctgcc tcagcctccc aaagtgctga gattacaggg   20160
gtgagccatt cactgttcct tgctaaatct tttttttttt tttttttttt tttttgagac   20220
agagtctcgc tctgtcaccc aggctggagt gcagtggtgc gatctcagct cgctgcaagc   20280
tccacctcct gggcttaaat gattttccta cttcagcttc ctgagtagct gggattacag   20340
gcacacgcca ccatgcctgg ctaattttg tatttgtagt agagacagag ttttgccatg   20400
ttggccagac tggtctcgaa ctcctgacct caagtgatcc acctgcctaa gccttcctaa   20460
gtgttgggat tacaggcatg agccaccaca cctggcctaa atttttttttt ttaatgagtg   20520 aaggagtcca tagtctttca tactttgggg tgatacaaga aaaggaaaaa ggtttaatga   20580
caactgccac tttcatttat tcattccttt gttgatgtac ttttgggctg ggttttgctg   20640
ttataagcta aactacaatg gacatccttg tacacattcc ctagagtcca agtacaagat   20700
tttctctagg gtgttttcct ggaaaaggaa tgacttgagg agtatggcaa ccttgtgaga   20760
aatgactgat tcgaaagatg tgtcccatag cttttgatac attttctcc gaagtcatgg   20820 ttccagtcca cactcacacc agctgtggag gagttttcat ttacccacga gctttgttat   20880
ttctggtttt gtcagtcttt tcaattctgc caatctcata gggtgtgatg gtatctcgtt   20940
gtttaaacct gacttctctt gttaaggttg agaccgagca tctggcccca tgtttgctgg   21000
ctattcagct ttcctcttct gcagactgcc cgtttgtcca ctgctctgtt tcagtaactt   21060
ccatatacca agaactctct gccttccata actcacatca cttaaaatac gaattttttt   21120
gatgcttaga gaacctgatt tccttccaac caattgtgct ctcctaattc caacaaccaa   21180
atgaagcttc aactcttctt tttgttcaga gccctcctga gtcctgtcct actcacagta   21240
aaggctgtgg caaataaat aaataagtaa ataaagggga aaaatacact gcatccaaaa   21300
aaggctcgtt tctttttctt tctttctctc tctctctttc ttttctttt tctcttgttg   21360 tgacaattgt cacaacaaaa tgtgtatgtg acaatttgtt atcttaaaac agtttaccca   21420
aaatagaaac cttacaaagc cagtggaaac ttttctttt gcataagttg gttaattctt   21480
ttgagtgctg gcctgggatc catgaaataa cctcaactcg accataaaac ttttcactcc   21540
cacgttatgc aaacggtgat gaccttgttg gtggcaagcc ccccgtgtga ctttccgagg   21600
ggatctgagt ggtgcaaggt ggaggacgca gtgatggaaa cattgcgaga gggaaggcgt   21660
ctgtttccac ccacttaccc tcagagcatg agggctgggc gaaggctctg actcctgtag   21720
ggggtgaccc atttctagga ctatagaagg agaggtgtgg acctggaaaa aggaaggaaa   21780
```

```
gaccacggca aggaaagtca agaagtggga gaagtcaagg gctctctcct cccttcctcc   21840
ttgtccttgg cctgcagcaa ctcctctttc tcttttttgtg gggacagact gaagaggatt   21900
tcttagtatg gtttgtacct tcccagtaga gcaggaaaaa gaggaacgag ctgctccctc   21960
cacacctcag acgctgaggt caactgcccct tgggcgggg cacgttggct cacgcatcta   22020
atcccagcac tttgggaggc cgtgagggga gcatcacttg agcccaggag ttggagaccg   22080
gcctgggcca catagtgagg ccccatcctc cggcttgcac cactcaaatt ccctcgtaaa   22140
gtcacacggg gagcttgccc ccagcaaggt cgtcagtttg caaaacatgg gagtgaaaag   22200
ctttatggtg gagtgtaggt tatttcatgg atcccaggcc agcacccaaa gaattaacc    22260 atcttgtgca aaagaaaat tttccactac ttttttaaag tttctatttt gggtaaatcg     22320
tttcaagata acaaattgga gagagaccta gagagaaatg agcctttta agatgcagtt    22380 tattttgccc catgatgttt ttgttttttgt ttttgccaga gcctttactg tgagtaggac   22440
aggactcagg aggcctctga acaaaaagaa gcgttgaagc ttcatttggt tgttggaatt   22500
gggagagcac aattggttgg aaggaaatca ggttctctca aaaataaaa taaaataaaa    22560 taaaaaaaaa agccagcgtg ctggcgcggg tccatggtcc aagctacttg ggaggctgag   22620 gtgggggat cgcttgagcc cggaagtcga ggctgtagtg agccgtgatt gcaccactgc    22680
actccagcct gggcgataga acaagaccct gtctcttaaa acaaacaaga aacaaaacaa   22740
aacaaacaac aaaaaaattc atttgggaat gtttctgcgc gtgcccataa gcagagccat   22800
gctataggat ctcccctgtg ccccaacaat cagcttctta cttggagggt agagaacggt   22860
gcttccccac gctgctgtgc aatggatagg agctatgtga agctggcgta tgggtggggt   22920
ttgcaggctt cgtccggctt catcgccggc tgctgacccg gcaccaattc ctgttctgca   22980
ggtctcaccg cagaggggca cgccagccat gaggacagat gagggaacac gtgatgccac   23040
gatgggggtg ccaggatgag gtgggtgcgg tcgcggacag gcgcacgagg agcccagcgg   23100
agcgccaccc ggagcaggcg cggaggaggg ctggggaggg ccaccaaggc gacgagagcc   23160
ggtgtgcctg aatcagccta aggagacgg aggaggagtg tggtgggcgc aggggcaggg   23220
agctggggga agggcggggg gctagcccag gctgaaggca ggcaggagca gggccgcgat   23280
gtcagacaag aaacggcagc agtgtgtttg ggaacctagc accaaccgca ccggtggaga   23340
cagggtctgc tgtagaggag gtggggccgg gtcccagcta agtaaggcgg tggatcttgc   23400
agcccttcca tcctcagccg ctcattctgc gcaaatctcg gggccagcct tggtggagcc   23460
gtaaagcgtc caccagaacc tggatccctc cgccaccttt cccatgaatt caccttttctg  23520 tacacagcaa gcgcctgagc ggagacggcc gacacgtttc ccactgttac cccaggaaac   23580
cgcggctcct gagggggtca gggcctgggc aggggcaga gctcagcgcg ccgtactgag   23640
gcagaaacgg ggtccagaga gggtgggtg ggggtacagg aagggtcgc ccgaaggtcc    23700 ctggcgcagg gaggacagag gagggatcta gaattcgtag gggagaagag aactcagaaa   23760
agatccggcc cagcgcattt atttttacaga g                                23791
```

<210> SEQ ID NO 3
<211> LENGTH: 692
<212> TYPE: DNA
<213> ORGANISM: Homo sapiens

<400> SEQUENCE: 3

```
aaaggaagga aagaccacgg caaggaaagt caagaagtgg gagaagtcaa gggctctctc    60
ctcccttcct ccttgtcctt ggcctgcagc aactcctctt tctcttttttg tggggacaga   120
```

| | |
|---|---|
| ctgaagagga tttcttagta tggtttgtac cttcccagta gagcaggaaa aagaggaacg | 180 |
| agctgctccc tccacacctc agacgctgag gtcaactgcc ctttgggcgg ggcacgttgg | 240 |
| ctcacgcatc taatcccagc actttgggag gccgtgaggg gagcatcact tgagcccagg | 300 |
| agttggagac cggcctgggc cacatagtga ggccccatcc tccggcttgc accactcaaa | 360 |
| ttccctcgta aagtcacacg gggagcttgc cccagcaag gtcgtcagtt tgcaaaacat | 420 |
| gggagtgaaa agctttatgg tggagtgtag gttatttcat ggatcccagg ccagcaccca | 480 |
| aaagaattaa ccatcttgtg caaaagaaa attttccact acttttttaa agtttctatt | 540 |
| ttgggtaaat cgtttcaaga taacaaattg gagagagacc tagagagaaa tgagcctttt | 600 |
| taagatgcag tttatttgc cccatgatgt ttttgttttt gttttgccaa gagcctttac | 660 |
| tgtgagtagg acaggactca ggaggcctct ga | 692 |

<210> SEQ ID NO 4
<211> LENGTH: 16040
<212> TYPE: DNA
<213> ORGANISM: Homo sapiens

<400> SEQUENCE: 4

| | |
|---|---|
| agccccttag tcgaagcgcg tcctgctgcc agctactacc aagtccttag gccgagcccg | 60 |
| tttctctcct ggtgatgtga atcctcgttt tttgttgttg ttgttgtcgt ttactgaagt | 120 |
| cccgggctga ttagacacag caatggaagc tgggggtggc ctgggccgtg cattgaattt | 180 |
| gtgactttag caagtcccta aattcctctc tgcctcactt tgctgtgtct ttttaggtta | 240 |
| aaaatatttt ggagaataga aaacagaaca aaacaaaaat aatggcttat agtgccaata | 300 |
| tggaattata gtcactccta acattttggt atattgtttt gcatttgctt tgtttctatt | 360 |
| ctatgcttat atattttta tttttttcca tcactgtcat catatttcct attcaggtct | 420 |
| ccagcctgct ttaaaaattt tttaatcata agttccata aaatttttat ttcagccaat | 480 |
| ttctttata acacgttctt catgaatctt atctgatatc tgcataatat tccactcata | 540 |
| ctttgcacaa ttagacatta aggtcgtgtg tacttttaa attatgatac agcaatttct | 600 |
| aaatagtgta taatttcaat ttttgtttct tagttatcat aacagttctt aaaaggtgat | 660 |
| aacaaatttt taagtggata cattttttcc cccttctttg gtttataatt ttattgctct | 720 |
| gtggtctgag aatgtggctg tatttacgct ttttgaaatt gaagttttg attgatggtt | 780 |
| gatttcgtaa ataagtttag gcacagtttt gtataaatga ttgggcacaa aattctttat | 840 |
| attagatcaa gctttgtaaa atgtattatc catatctgct atgtcttttt aaaatttta | 900 |
| tctacttgat ctaatttctg aaagagctgt aagttttta aatgtgtttg tggatttact | 960 |
| atttcttctt tatatata tatatata tatatatttt ttttttttt tttttttttt | 1020 |
| ttttttttg agacggagtc tcgctctgtc gcccaggctg gagtgcagtg gcgtggtctc | 1080 |
| ggctcactgc aagctccgcc tcccgggttc acgccattct cctgcctcag cctcccgagt | 1140 |
| agctgtggtt actggcgccc accaccacac ccggctaatt ttttgtattt tttagtagag | 1200 |
| acggggtttc accgtgttag ccaggatggt ctgcatctcc tgacctcttg atccgcccac | 1260 |
| cccggcctcc caagtgctgg gattacaggc gtgagccacc gcgcctggcc tcttgttat | 1320 |
| atttctaaca gtttgtgcat tatatatttt aaagtgatgt tatggagtat aaaaaccata | 1380 |
| tggctgttaa agtaataaac aaagaaacat tttggcttat atatcttttt gtgcatttga | 1440 |
| attattttct tggtttgaat ttttagaagg aaatggctct taaaggcaag ttggccttt | 1500 |

```
aaagatttga cagatgtata ctgttggctg catcagagtt cttctttcac taacccctgg    1560
tcagccccag gaattaaaaa acaaattaca cacacacaca cacatacaca cagatacacg    1620
catatagtaa gtcttcactg tcatccatag gttcttggaa actgcaactt taagccaaac    1680
aacatataat aaaaccagtt tttcaatcaa cattgtaaca aaacaacatt gaatgaaaaa    1740 atacttttg aggatctgct gtatgttatt ttgcttaaaa tcacagtttc caagaaccta     1800
tacatgatgt taagtgagga cttagtatgt gtggtgtgtg tgcgtgtgtg tgtgtgtgtg    1860
tgtgtgtaca tgcatcagtg ttattttggg agaagcaaga agtgggataa ttttacaat     1920 ctcctttgat ttttattgcg gttgacggtt tttctgtaga tctgtaatca cttgaattt     1980 cttttttgtg tgtggattgt ctgttcttgt ccttttgtgc ttctgttttc taacttttaa    2040
ctgaaggagg ttaatgtctt tcagctctta acactgtagg aattacattg ctatttcttc    2100
taccacaaaa caccttattg aaaagaaaa actccagcac accaaacaga tgcctcaaat     2160
tcaccctgac tgcccctgct cccctggat cttagcagaa atttcagtgt ggcaaacaaa     2220
gcagatagag ttcctatggg gcctaaagct tatgcaattt gggaaacttc tttaaccatt    2280
ttttttttga gtagtgagat tttagcatat tttggctaaa atatgggaa aaataatgcc    2340 cagtgagatt acatgatttt cctgggattg atagattcat gtctcaattt ccatcagaga    2400
aagggagtgg ggtggtgagg aagggaaagt agtatggaga gttaggaccc tttgccttct    2460
ttcaggataa gaaagaaaag gaatagccga gcttgccata cacaagcggc cccattcatt    2520
tgtaatattc cttcggtatc cttttattgt ctgtgagatc catagtgatg atctctcttt    2580
tgtttctgat atgagtaatt tttgccttct ctctttttc ttggttagat tgactagagg     2640
tttaccaatt ttactgatct tttcaaagaa atagcttttg ttttatttc tctattgttt     2700 cctgttttca gtttcattga tttctctaat ttttattatt tttattcttc tgcttgcttt    2760
aggcttgtat tgctcttcct tctcttgttt cctaaggtgg aattttagat ggtcaatttt    2820
agatctcttt tcaaaatatg tgtatttaat gctataagtt tccctcgaag tactgcattg    2880
ctgcatccca tgaatttga gaagttgcat tttcatttag ttcaaaatat tttaaaatat     2940
ctcttgagac gtcttctttg acccatgtgt tatttagaag catgttgttt aatcttcaaa    3000
tatttggaga cttttcagct ctcttttttgt tattaatttc tagtttaatt ctgttgtggt    3060
ctgacagcat actttatatg atttctgttc atttcagttt gttaaagtgt gttttatggg    3120
aaagaatgca atctcttttg gtaaatgttc catgtgaact tggaagaata tgtattttgt    3180
tgttggatag agtattctat aaatgtcaat tagatcaaac tggttgagag tgctgttgag    3240
gtcaattaaa tcattactga ctttctacct gctagattta tcaattattg agagagaagt    3300
attgaaatat ccaactataa tagtgacttt gtgtattttt ccttgcatac ctatcatttt    3360
ttctctcagg tattttgatg ctttgctaat acatgtatgc atgttaagga ttgttttgtc    3420
ttcttggaga attgacccctt ttaatattat gtaatgtcct tctttatccc tgatgattt    3480 ccttgctatg aagtctgctt tgtctgaaat tagctactcc agctttcttt tgatagtgtt    3540
aacaagatat atctttctct attccttata acccatctga gtcttacatt taaggtgggt    3600
ttcttgtgga cagcatatgg ttaggccttg ctttttact actctgacaa tctctgtctt     3660
ttacttggat atatttagac cattcacatt gaaagtggtt attgatatag ttggattagt    3720
atctactatg ttcgtaactg ttttctattt gttacagttg tttttttgtct cttctttccc   3780 ctgtcccgtc cattgtaatg actgtttatc aacgttttcc caaagattgc ctgagctctc    3840
aaccagtatc atgtctatct ctgtgtgcag caaaatatac ttcctcatac ctgtgcataa    3900
```

```
taaggcaggt gcgaaggtgt tcatgcagca ctgcctttaa agtgggaaaa cccagtcttc    3960
atcaatgggg caataggaat ttaaattatg gttcaccgac ctacaggaat accaggaggc    4020
agtcaaacat aagccaatac atctatatgt cctggaatat agcaaattct gacatatatt    4080
gtcaagtaaa aaaagctagt tgcagaccaa tatatatatt ataactcttt taggtaaaaa    4140
tcgtgtgtgt gtgtgtgtgt ctgtgtgtga atgtctaaat gcacagaaaa atgtgtgtct    4200
aaatgcagag aaaaatctct aggtttatac aaactgtgtg ttttttacaaa ctgatggcag    4260 atttgggaaa gcaagaaat attaattata ttttttctga caaaacttat attcatgtat    4320
ttgtaagctt taaacacaca cacacacaaa cacacacaca cacacacaca cacacgcaca    4380
acttatttaa gaccagactg gccaacatgg tgaaaccctg tctctacaaa aatacaaaat    4440
ttagccaggc atgatgccag cgcctgtaa tcccagctac tggggaggct gaggtggaag    4500
aattgcttga acccgggaag gtggaggttg cagtgagcca agatcacacc accgcactcc    4560
agcctgggca acagagtgag actctgtctc aaaaaaaaaa aaaaaaaaaa agggctgggc    4620
atggtgctca tgcctataat cccaacattt tgggaggctg aggcaggcag gttgcttgag    4680
cccaggagct caaggccagc ctgggcaaca taaggagacc ccgtgtctac aataaataca    4740
aaaatttgcc aggtgtggtg gtgtgcacct gtagtctcag ctacccagga ggctgaggtg    4800
gaagaattgc ctgagcctgg gaggtcaacg ctagagtgag ccgtgattgc accactgcac    4860
tccagcctgg gtgacagagt gagaccttgt ctcaaaaata aaaataaat taaaagtagg    4920 ccgggcctgg gtggttcatg cctgtaattc cagcactttg ggaggccgag gtggttgaat    4980
cacctgaggt caagggttcg agaccaacct ggccaaacat ggtgaaaccc cgtctctact    5040
aaaaatacaa aaattaacca tgtgtggtgg catgtgcctg tagtcccagc aggcagaggc    5100
aggagaatca cttgaaccca ggaggcagag attgtagtga gccaagatcg agtccctgca    5160
ctccagcctg ggtgacagcg agactccgtc tcaaaaatat ataaataaat aaaaaaaata    5220
aattttttaa aagcaaagaa gcttaaaaac gctttccttc acaaggaaag aacatctgcc    5280
tgacataagt aaccctctct aacctcagca tttggcggct gttctgaaat gggtggtcca    5340
tactcatagt gatctggtgc tagagatgca ggaagcaaag atgttcccca gtacttgcca    5400
agctcaatgg ttcccttttc ccggtcttta ggattttggg caaatttatt caagatggat    5460
acatttggtt ccacaagggg gacactttgg ggttcacaag gatgggggcc acagctcacc    5520
agggcagaac ttgagccccc tatgacttgg ggggttgatg gtggcagaga agtctctgct    5580
gggtgtgtgg gaggatccct ctgagcgagg gaggaatctg gtaaaagtag taaagatcca    5640
ctcatcagga cctgtgcttc ttgcctatgt tttcaggatc catgggttaa gcagcttctg    5700
tgaggttgta gtattgctgt agtatccatg caggcattgg gggacaaagg ttcctgatat    5760
accttcccct tgaggccttg caaaagaaa acaagagag tctcaataca tgcaccaagt    5820
caaggtgttg gttacttatt aagtaatgac tgatttttt ctgtgactca gtcgagtcag    5880
atgttgtgtc aaattcaaca cagaaagagc caggcatata gcacttgata ggcctagggt    5940
taccacagga tccaaccaca tttgattcag gatctcaaag ccagaaacct ctgtttctgt    6000
ttcttgtgat ttcttctcag aaagaggaaa ccacacacag agaattaccct gctcagttat    6060 tccccaaagt taatatcatt tgggaaagcg ggtgagggtt ttatccttcc ctcttgggca    6120
tcactgtcaa ttttattgcc atggttaatc aaggtgaatt tcaatagtgt ctgacctgca    6180
aattagtttt ctgccatttg gaatcaagga tgtacgggtc aacagctgca ggagacttca    6240
```

-continued

```
gagaggtccc catgcttaaa aaatttctct caggagagta gtaaggtagg gtggctattg    6300
tcatcacagg ttggaagaca agatggtcac aaatgttaga gaatttattc tgatggaaac    6360
ttctcctccg gggtacttta taatggacat gaagactcaa cttcaggaag atgtaagttt    6420
tccccagtta atctacagat ccagtgcatt caaaatgcca accagatttt gctcacaagc    6480
tgattatcaa attcatatgg aagtataaag ggccaaaaat agctgaataa ttttgctgaa    6540
gggtaagggg gggacccatt attccacata tcatgattta taaactctag taatttaaac    6600
acaaatagaa caatgaaaga gagtaggggg cctagaaaat acagatgtga acatgttgga    6660
gatggctggg cactcctgtg ggtaaaggat tcgatcatta gtgctgtgac attggcttcc    6720
catgtgggaa aaacgtaaaa cttgaactct atctcaaacc attcacaaat gtatactcca    6780
gatagaataa atatgaaaag caaagtttca aaacttttt aaaaaatgtg tttttaagac    6840
agagacatga taaggcacag aatttcttgg tcaaaatata aaaggacaag ccataaaagt    6900
gtgatgttac cattcgaaca tttgtttaaa gtatgcaggg caaaaaccaa tacaaagtta    6960
aaggacaagt ctcaaattag tagaagatat ttgcagtgca taaaagcaac agaagatctt    7020
tatccataac atatcagact ctcacaaagt aataagttaa agacagcaga attaaaaatg    7080
ggcaaagtac gtgaccaagc caatatccaa ataaaaagat gccaaacatt acttgaatca    7140
gtgagatgca aatgaaaaca accaatatca ttttatattc aaattagcaa aatgaacaag    7200
accaataaca tcaagcatga gggaggatat gaccaaataa ctgtgatgca gtgttgatgg    7260
ggatgtaaat tgttacaact gcagtggaga taatttggga tatctagtaa aaatatctat    7320
taaaaatgaa gatgctctgg ccccagaact tccacttcca gattcattgc tcagagaagt    7380
tttgatgtat aagagtgttc acagaagcac aaacaacaga aattggaaaa ttgtaataat    7440
aattataaac taatatctaa taggggaatg aataaaaattg taatacatta ataaaatatg    7500
acacaataaa tgaactagat ccacaggcat caacacaggt aaatctcaaa aatatgttga    7560
atgaaataag caaattttaa aagtgcatgt acactctgac attatttata aaaaataaaa    7620
gcacatgcca tatattattc attattatgt cattgtttat agatacttac ataataagag    7680
aatcacaagt ataaaaaaag cctggaggca gaacccacaa atttcaagat agggtatgca    7740
gtatggagga tggaataggg gtgaagaagg ggtctcaaca caaacatttt attgcttgaa    7800
ataaaagact gaagcaaatt tggcaaaagt taaatttgct aaatctgaca gatttattta    7860
gcaaatctgc taatttgcta aataaacttg aagctagtat gttaccttca gtagttttct    7920
ttatatttgg cataattcat aattcatggg aggaggtaat tacatattaa aaatatatat    7980
tcactggctg ggtgcagtgg cttatgcctg taatcccagc actttgggag gccaagatgg    8040
gtagatcacc tgagttcagg agttcgagac cagcctggcc aacatgatga acccctgttt    8100
ctactaaaaa tataaaaatt agccgggcgt ggtggcgggc acctgtggtc ccagctactc    8160
aggaggctga ggcaggagaa ttgcttgaac tgggagatgg aggttgctgt gagccgagac    8220
tgtaccactg cacttcagtc tgggtgacag agcgagactc catctcaaaa taataaaata    8280
aataaaaata aataaataaa gtatatattc ataattaaca gagtaactgt atgtaatgag    8340
tacctgctgt gttccaggca ctgttttaaag tacaggcata cctcatttta ttgcacttta    8400 ttttttttatt gtgctgcacg gatgttgtat ttttagcaaa ttgaaagttt gtggcaaccc    8460
tgcctggagc aaatctatca atgctgtttt tcaatagcat gtgttgactt tgtgcctctg    8520
gatcaccttt taataattct tgcaatacct caaacttttt cattattatt gtgtctgttc    8580
tggtgactgt aatcagttat ttttgatgtt actatttaa ttgtttagg gcaccatgaa    8640
```

```
ccatgcccat ttatgacagt gaacttgatc cataaatgtt gggtgtgttc tgactgctcc    8700
atgaccagcc attctgtatc tccttctcct taggccccccc tatgccctga gccacaaaaa   8760
tattaaaatt aggccaatta ataaccctac aatggtttct aagtgttcaa gggaaaggaa    8820
gaattgcgca tctctcactt taaatcaaaa gctagaaatg attaagttta gtgaggaagg    8880
gatgctgaaa gtggagacag gctgaaagct aggtctcttg tgtcaaataa tgagccaagt    8940
tgagaaggta gagaaaaagt tcttgaagga aattaaaagt actaatccag tgagcacatg    9000
aatgataaga aaacgaaata gccttattgc tgatatggag agagttttag tggtctgggt    9060
aaatcggaac agccacaaaa ttcccttaag caaaagccta atccagagca aagtcccaac    9120
tctcttaaat tttatgaaag ctgaagtggt gaggaagctg cagaagaaaa gtttgaagct    9180
aggagaggtt ggttgattca agtggtttaa gggaagatac catctcctta acatcaaaat    9240
gcaacgtgaa gaagcaggtg ctaatataga aactaatagg tgctgcagca cagcaggtta    9300
tccaaaagag ctttctaaga ttattgacaa aggtggctac actaaacaac agattttcaa    9360
tgtagacaaa acagccttat attggaagaa gatgctacta ggtctttcat agctagagag    9420
aagtcaatgc ctggcttcaa aggacagcct gcctctcttg ttaggggcta atgcagctgg    9480
tgactttaag ttgaagccaa tgctcattta ccattctaaa aaccctaagt cccttaagaa    9540
ttatgctaag tctactctac ttatactctg taaatggaat agcaaagcct ggatgacagc    9600
acatctgttt agagcatggt ttactgaata tttaaagccc actgttgaga ctcgctcagg    9660
aaaaagatt cctttcaaaa tattactgct cattgaaaat gtgcctggtc acccaagaga    9720
tctgatggag atgtacaagg agattaatat tgtttttcat gactggtaaa acaacattga    9780
ttttacatgg accaaggagt aattttgact ttcaattctt attaagaaat acatttcgta    9840
aggctagagc tgccacagat gatgattcct ctgatagatc tgggtgaaac cttctggaaa    9900
ggattcacca ttctagatgc aacaaagaac atttgtgatt catgggagca ggtataaata    9960
ccaacattag gaggagtttg gaagcaggtg attccaattc tcctggatga gttggaggag   10020
ttcaagactt cagtggagga agtaactgca agtatggtag aaatagcaag agaactagag   10080
atagaagtgg agtctgaaga cgtggctgaa ttgttgcaat cccgtgatca aacttaacac   10140
atgaggagtt tattctctct gatgagcaaa gaaggtggtt tcttgaaatg gaatctactc   10200
ctggtgaaga tggtgtgaac attgttgaaa tgacaacaga agatagagaa tgttacataa   10260
acttagttga gaaagaggcg tcagtatttg agaggagtga ctccaatttt gaatgctgtt   10320
ctactgtagg taaaatgcta tcaaacagca tcgcatgcta cagataaatc ttttgtgaaa   10380
ggaagagtca atcaatgtgg caagatttgt tgttgtccta ttttacgaaa ttggcacagc   10440
cacgccagcc tttggcaacc accattctga tcagtcagca gccattgaca tcaaggcaag   10500
atgccctcca tcagcaaaga aattatgact cactgaaagc tcaggtgatt ttagcatgta   10560
tttggtaata aattattttt tgattaagac gtacttttt tttcagacat aatgtctttg    10620
tacacttagt agactacctt atagggtaaa cataactttt atgtacactg ggaaaccaaa   10680
aaatgaatgt aactggcttt attgtgtatat ttgctttatt gtggtggtct ggaactgaac   10740
ctgagatatc tctgaggttt gcctatactg gaatttccaa ggttagtgaa acatcctttc   10800
tgcagcctga gtggtgagat ttaggctagt ctcaaaaata taaaaaataa ctagaatata   10860
atgtaataac agtgatcatt aagataacaa tgctagcagc taccattgac tgagtagtat   10920
gtgccatgca ctctgcaagc actattttat taatgctcat gtgtgaggta gatattatca   10980
```

```
ttattcttgt tttatattca aggttcagag aggttaattc acttgctcag agtcacacag    11040
gtagcccaga tctgctatgt gccagcccta attactgagc catcctgtct gtcccacctt    11100
ttctgaccca actccccact tctgaaccac aggcggtgta gctggctttg aatataggtg    11160 ctcttttat ataggtactc ttgaaaggat caactttact tttttttttt ttttcaaata    11220
atccaataac tttgactttt tattaggtta cactggcatt ctcccaagtt tttcatcaaa    11280
ctcatgaagc ctgctgctcc ttcaattctc aaggcgttgg agtgaggccg cctggggtga    11340
atcgaagctt tcggatttat caaatgtggt gtgatttcta agacgccatt gagccctgct    11400
aaaggagttg ctaatatcca cctcgttctg cggttaagaa accaacagga aaaagaacgc    11460
acaactccca gcacagtgct ggcgcctgtg aggcactcag ccgacgggag ctttgttctt    11520
cgttgtattg tggcgggaa gcaacatggg gccttgtcct gcggacacac ttgagttaag    11580
atcacactgg ggctccttca ggccctgggc caagttgggg cacaggccga gttcggttgt    11640
tgctgtagcc tcagaaccac ccagagttga ctgaagacac tcgggggcct ccataactga    11700
gagcaggcag aggcattgtt tttaacccag tgtggacccc caaatggaac attttccttc    11760
cctaggtgaa cgccttcgga accctccgaa aatcgcagtt tcacttttag caaagagccc    11820
cgctgcagca ggggaaagcc cccacaaacc ccgtcctctc caaagggaat gttccgagcc    11880
ccctgcttcc tccaccctc tcttcccct ggttaattcc ttcgctccag ctcgttctgc    11940
cttctttctt tctttgcctt ttcgaggccc gctcttctct gatttgaag ggctggcgca    12000 ggcttgggca cttctttcag gttctgtatt gtatgtctgc cctgtggctt ctccttttgc    12060
aactccgagc aactctgtgc ttggattgca gctcccaaca gtcctgccct gacttgcccc    12120
agtcacaggg cagagatgaa ccagggactg tacccagggt tttgagttcc tgccatattt    12180
atagcatcaa ctctccttta gctcttggga aaagggttt taaagtgctg caatcttcta    12240
acacaaaatt atatcagtgc tgaaaatgtg ttttccactt ataccccagc aggaaaaaaa    12300
aaaaagatga tatctgtttc aggtaagagt catgatgacc tcagaaagca atatcagaag    12360
ctatcaaaat gtttatacct gtatattcag tagtccattc tggaacattt ctccagtgga    12420
tgtaatctta gtcttggcac aatagagtat gaacagagat gttaaatgtt aaaagcaatg    12480
gaaatgttca gaaataaagc aatatttaag taaacaatga taatgcattc aatataatttt    12540 taggcattaa catgatgatg ttttagaatt atgaaaccta tggaaaggtt gacaaggaaa    12600
acgcagacag catgcttgat ataaacatac attcagcatg attataacta tgtaaaatgt    12660
aaaaaatgtt tttaaaacat tagaagaaaa tacaccaaga tgcgtttccc ttgctgttgt    12720
ttctagtggc taatttttgc aatgtgtatt actgcagtta tatcacctttt acaaatggaa    12780 agcttaaaaaa taactcactt cccttcccag agagcaatgt tcagtgcaaa gccacactcc    12840
actccaggga tggccttcag cactggactt tttgggagcc agaatcaagc agtatgtgtc    12900
acttcttatc tcatgttgtt ggtgccactt actcatatgt tgtctcatca ttctgcagtt    12960
gtttaatgtg tttatatctt tctctacaac cattttttaa aagctatttt taaaattgtg    13020
gcaaaatgta tgcataacat aaatttacca ttttagtcat ttctaagtat acactccact    13080
ggcattaagt atatttatat ttttgtgcaa tcattaccac catgcatcca cagaactttt    13140
tcatcttcct aaactaaaac tctgtaccca ctaagcacca actccccatt cccctcccc    13200 cagttccagg taaccgctat gatatttttca gtttctctga cgaattcaga gacaccactc    13260
ttggtacctc ctgcaagtag aatcatactg tatttacctt tttgcacaat catttttta    13320 aacttaaaaaa aaattttttaa ttaattttttt tgagacagtc tcactctgtc acccaggctg    13380
```

```
gttggtgttt gcagtggcac gatcatggct cactgtagcc ttcacctcgt gggctcaagt    13440
gatcttcaca tctcagactc ccgagtattt gggactacag gcacccacca cggtgcccgg    13500 ctaattttt  aatttttgt  ggagatgagg tcttactatg ttgcccaggc tggtctcaaa    13560
ctcctaggcc caagggatcc tcctacttca gcctttcaaa gtgctgagat tacaaagcga    13620
gccacaagcc tcggcctgca caatcattat aaaaagctct ctgaggataa ggaccaaggc    13680
cctgatttgt tttcattgta aacataatgt tcatttgctc attgatttga tattgactgt    13740
gcacccacac gtgtgctggg cactgttcga ggcagggttt aagaaacgct caagaagcac    13800
atgtggtctc tcaaggggac ggtgtagtgg acagagataa caagaaaaa  cacagagaag    13860 aaagaatgac ggagagtgag aagtgctgta agtgcagtga cagacaccgc cccagggcct    13920
cctggacagg ctgcatgttt gtaggatgat ggggagtggt cctggagaag actgaggagg    13980
agccctgggg ggtccaggca gagagaggag gggcacagag ctggaggacg aagggcctt    14040 tgtacagcat gtgtgtgtgt gtgtgtatgc tgggggacac gcaggagat  ggcaggcctc    14100 agcactgggg agagctggag tgcattctag atgcagcagg gagctggagc agggaccctc    14160
ttctccctgc ctggcctgag agcagggaag gaggccctgg gctgtggctg attgcagtca    14220
acactgagga acaagtgcca atgcttcatg cagggcacaa cctctgccac acttttacct    14280
atgtgacctt ctgggccagg tactgtgagg tgcttcattt ctcagatagc aaggctgagg    14340
ctcagatcaa tgctgctttg cacacagctg gaagtggcca aatcagcccg aaaccccat    14400 tttgttctgc atctttgtgc agggctgggg ggctgtgtgt gcaatgtctg ttgtgctgga    14460
catgcaacag gaaagcaatt gttacctcta attttagga  ggccaaaggg caagaagcca    14520
cgtgctccag gccaaagagc agctaaggga atgaagagta aatctgtgat tgaatgaatg    14580
agcagatgaa aagagaaaaa gcctccccct gcacaaacct gcaacccatt cccttcctgg    14640
ggtcctgtgg ggaggggggct tttcatcagt gccctgggtc agggaagaga gagggaggcc    14700
ttgtggtgga gggaagggga ggagagctca ccatcagagg tggaaagaag gttctagtcc    14760
ctccagagca cactcaggga tgctttcttg tgcttctgtc ccaaggcctt gtctcgacct    14820
tgcttactat aaacacagtg ctacatcctg cttttccttt acttcattgc ataaaccttc    14880
cctgaatcgc ttccagaatc tttagaacca ccgttttaa  ggtttgaata cttgtatacc    14940
aagtaaatga ccacagctta ttgaaactcc tctttatagt caaccactta ggttgttcta    15000
ttgttatttc tagaacacat aactaatgcc aataaataat gatgatggca cagattagta    15060
tttcctgagg atggatctct tgcgtgggtt ccaaagctct aagcaattta tatgggcccc    15120
ggagtttcct ccacagctcc taaggcagct ctggcacatg aggaggctgg gaaaagagca    15180
ggggtgatgg gtgcatctgc cttggtaagt gaacttgttg gttctgtccc acgcagcttg    15240
ggtgtcggtg tgggggggtgt gctgctgggg ttggagaggg gccgccctac ataacgtccc    15300
cacataaaag gggcaggtgt gcaggtggtc ccagggatgg cggcagctct gtctgactcc    15360
cccctactgg ggggctatgg gggctgtggg agtggagggt gaggatcacc gtcctccagg    15420
atcccccaac ccctccttgg ccattccctt tgacttcctt gggaaagagt ccaggcttca    15480
gaggattctt tgctcatttc aatctgaccc catttgaatc cccaagggtc gcagtaaacc    15540
ccaggcacac aaagacagag gcttgtggct ggcttgcggt tgctgtgatc acgatggaat    15600
cagacaacgg ctgccctggc aggcagcacc caggcacctc tcaggtggga aaagactgag    15660
ccaggtgaat gtcccagagc tccagccagc tcaggctcct atgggtgata actgcactag    15720
```

```
acacctctcc gaagaagcca acagaaactg catgcagcgg caacatgagc aaagataagt    15780
gttgggaccc gttcttcgct gccacctcca agtctgaaca gcaggctcta agggggcat     15840 gggagcccct cagaaagggc cactgcccat gcctcacctc ctgcccgcca ctccactctt    15900
tattgtccta cctgactgta acaggctgca tgctcaacat ggtgtcagct gccccaaaga    15960
gcaccaggag gagacagggg tgccattcgg acatgaacag gagctcctac ctgaatgtgc    16020
agacctccgc cactggagct                                                16040

<210> SEQ ID NO 5
<211> LENGTH: 464
<212> TYPE: DNA
<213> ORGANISM: Homo sapiens

<400> SEQUENCE: 5
cctgctgctc cttcaattct caaggcgttg gagtgaggcc gcctggggtg aatcgaagct     60
ttcggattta tcaaatgtgg tgtgatttct aagacgccat tgagccctgc taaaggagtt    120
gctaatatcc acctcgttct gcggttaaga accaacagg aaaaagaacg cacaactccc     180
agcacagtgc tggcgcctgt gaggcactca gccgacggga gctttgttct tcgttgtatt    240
gtggcgggga agcaacatgg ggccttgtcc tgcggacaca cttgagttaa gatcacactg    300
gggctccttc aggccctggg ccaagttggg gcacaggccg agttcggttg ttgctgtagc    360
ctcagaacca cccagagttg actgaagaca ctcgggggcc tccataactg agagcaggca    420
gaggcattgt ttttaaccca gtgtggaccc ccaaatggaa catt                     464

<210> SEQ ID NO 6
<211> LENGTH: 475
<212> TYPE: DNA
<213> ORGANISM: Homo sapiens

<400> SEQUENCE: 6
ccacccagag ttgactgaag acactcgggg gcctccataa ctgagagcag gcagaggcat     60 tgttttaac ccagtgtgga ccccccaaatg gaacattttc cttccctagg tgaacgcctt    120
cggaaccctc cgaaaatcgc agtttcactt ttagcaaaga gccccgctgc agcagggaa     180 agccccaca aaccccgtcc tctccaaagg gaatgttccg agcccctgc ttcctccacc      240 cttctcttcc ccctggttaa ttccttcgct ccagctcgtt ctgccttctt tcttttcttg    300
ccttttcgag gcccgctctt ctctgatttt gaagggctgg cgcaggcttg ggacacttctt   360 tcaggttctg tattgtatgt ctgccctgtg gcttctcctt ttgcaactcc gagcaactct    420
gtgcttggat tgcagctccc aacagtcctg ccctgacttg ccccagtcac agggc         475

<210> SEQ ID NO 7
<211> LENGTH: 318
<212> TYPE: DNA
<213> ORGANISM: Homo sapiens

<400> SEQUENCE: 7
gggacagact gaagaggatt tcttagtatg gtttgtacct tcccagtaga gcaggaaaaa     60
gaggaacgag ctgctccctc cacacctcag acgctgaggt caactgccct ttgggcgggg    120
cacgttggct cacgcatcta atcccagcac tttgggaggc cgtgagggga gcatcacttg    180
agcccaggag ttgagaccg gcctgggcca catagtgagg ccccatcctc cggcttgcac     240
cactcaaatt ccctcgtaaa gtcacacggg gagcttgccc ccagcaaggt cgtcagtttg    300
caaaacatgg gagtgaaa                                                  318
```

```
<210> SEQ ID NO 8
<211> LENGTH: 23
<212> TYPE: DNA
<213> ORGANISM: Homo sapiens

<400> SEQUENCE: 8
cctactactc cttcaattct caa                                          23

<210> SEQ ID NO 9
<211> LENGTH: 22
<212> TYPE: DNA
<213> ORGANISM: Homo sapiens

<400> SEQUENCE: 9
aatgttttat ttgggggttt at                                           22

<210> SEQ ID NO 10
<211> LENGTH: 22
<212> TYPE: DNA
<213> ORGANISM: Homo sapiens

<400> SEQUENCE: 10
ccacccaaaa ttaactaaaa ac                                           22

<210> SEQ ID NO 11
<211> LENGTH: 20
<212> TYPE: DNA
<213> ORGANISM: Homo sapiens

<400> SEQUENCE: 11
gttttgtgat tggggtaagt                                              20

<210> SEQ ID NO 12
<211> LENGTH: 22
<212> TYPE: DNA
<213> ORGANISM: Homo sapiens

<400> SEQUENCE: 12
gggatagatt gaagaggatt tt                                           22

<210> SEQ ID NO 13
<211> LENGTH: 23
<212> TYPE: DNA
<213> ORGANISM: Homo sapiens

<400> SEQUENCE: 13
tttcactccc atattttaca aac                                          23

<210> SEQ ID NO 14
<211> LENGTH: 27
<212> TYPE: DNA
<213> ORGANISM: Homo sapiens

<400> SEQUENCE: 14
ggttaagaaa ttaataggaa aaagaat                                      27

<210> SEQ ID NO 15
<211> LENGTH: 21
<212> TYPE: DNA
<213> ORGANISM: Homo sapiens

<400> SEQUENCE: 15
```
cttccccacc acaatacaac a                                          21

<210> SEQ ID NO 16
<211> LENGTH: 27
<212> TYPE: DNA
<213> ORGANISM: Homo sapiens

<400> SEQUENCE: 16
ggttaagaaa ttaataggaa aaagaac                                    27

<210> SEQ ID NO 17
<211> LENGTH: 18
<212> TYPE: DNA
<213> ORGANISM: Homo sapiens

<400> SEQUENCE: 17
ccccatatta cttccccg                                              18

<210> SEQ ID NO 18
<211> LENGTH: 33
<212> TYPE: DNA
<213> ORGANISM: Homo sapiens

<400> SEQUENCE: 18
tgtttgtgag gtatttagtt gatgggagtt ttg                             33

<210> SEQ ID NO 19
<211> LENGTH: 28
<212> TYPE: DNA
<213> ORGANISM: Homo sapiens

<400> SEQUENCE: 19
cgtttgtgag gtatttagtc gacgggag                                   28

<210> SEQ ID NO 20
<211> LENGTH: 27
<212> TYPE: DNA
<213> ORGANISM: Homo sapiens

<400> SEQUENCE: 20
ggttaagaaa ccaacaggaa aaagaac                                    27

<210> SEQ ID NO 21
<211> LENGTH: 21
<212> TYPE: DNA
<213> ORGANISM: Homo sapiens

<400> SEQUENCE: 21
cgttgtattg tggcggggaa g                                          21

<210> SEQ ID NO 22
<211> LENGTH: 27
<212> TYPE: DNA
<213> ORGANISM: Homo sapiens

<400> SEQUENCE: 22
ggttaagaaa ccaacaggaa aaagaac                                    27

<210> SEQ ID NO 23
<211> LENGTH: 18
<212> TYPE: DNA
<213> ORGANISM: Homo sapiens

<400> SEQUENCE: 23

```
cggggaagca acatgggg                                                    18

<210> SEQ ID NO 24
<211> LENGTH: 33
<212> TYPE: DNA
<213> ORGANISM: Homo sapiens

<400> SEQUENCE: 24
cgcctgtgag gcactcagcc gacgggagct ttg                                   33

<210> SEQ ID NO 25
<211> LENGTH: 28
<212> TYPE: DNA
<213> ORGANISM: Homo sapiens

<400> SEQUENCE: 25
cgcctgtgag gcactcagcc gacgggag                                         28
```

EPIGENETIC METHOD FOR THE IDENTIFICATION OF SUBPOPULATIONS OF CD8+ T LYMPHOCYTES, IN PARTICULAR CD8 ALPHA AND BETA T LYMPHOCYTES

CROSS-REFERENCE TO RELATED APPLICATION

This application is a continuation of U.S. application Ser. No. 14/443,223, filed May 15, 2015 which is a National Stage Application of International Application Number PCT/EP2013/074642, filed Nov. 25, 2013; which claims priority to Great Britain Application No. 1221133.0, filed Nov. 23, 2012; all of which are incorporated herein by reference in their entirety.

The Sequence Listing for this application is labeled "113828.000014_SeqList_March2019.txt", which was created on Mar. 11, 2019 and is 116 Kilobytes. The entire content is incorporated herein by reference in its entirety.

The present invention relates to a method, in particular an in vitro method, for identifying CD8 positive subpopulations of a mammal, wherein said method comprises analyzing the bisulfite convertibility of at least one CpG position in the CD8 beta and CD8 alpha cell specific bisulfite convertibility gene region according to SEQ ID No. 1 and 2, wherein a bisulfite convertibility of at least one CpG position in said gene regions is indicative for a CD3+CD8+ and/or CD3+/−CD8+ cell. The analyses according to the invention can identify CD3+CD8+ and/or CD3+/−CD8+ cells on an epigenetic level and distinguish them from all other cells in complex samples, such as, for example, other blood cells. The present invention furthermore provides an improved method for quantifying CD3+CD8+ and/or CD3+/−CD8+ cells in complex samples, in particular based on a comparison of the CD8 beta and alpha gene bisulfite convertibility with a bisulfite convertibility of at least one marker selected from the group of CD3, CD4, FOXP3, NKT, NK, T helper cells and/or GAPDH. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure particular subsets of CD8+ cells of the blood within any solid organs or tissue or any body fluid of a mammal. Employing this method, the inventors provide novel, not previously known means for determining, quantifying and routinely measuring CD8 alpha/beta and CD8 alpha/alpha cells.

BACKGROUND OF THE INVENTION

CD8 (cluster of differentiation 8) is a transmembrane glycoprotein expressed on the surface of cytotoxic T-cells, but also of natural killer cells, cortical thymocytes and dendritic cells. CD8 forms a homo- or heterodimer comprised of either CD8 alpha and/or CD8 beta chains. CD8 interacts with class I MHC receptors during antigen-specific activation, functions as a co-receptor which associates with protein tyrosine kinase p56lck, and participates in T-cell receptor-mediated activation. According to current research, homodimers only exist as alpha/alpha chains and are expressed by CD3+/−CD8+ cells (cytotoxic T cells, NKT cells), whereas the heterodimer alpha/beta is expressed by CD3+CD8+ cells only. In humans, the CD8 alpha and beta molecules are encoded by CD8 alpha gene and CD8 beta gene.

T-lymphocytes are a major component of the mammalian immune system. Cytotoxic CD3+CD8+ T-cells are an important part of the cell-mediated immunity and hence mediating the cytotoxic immune defense. CD8+ cytotoxic T-cells lyse cells displaying epitopes of foreign antigens on their surface in order to kill infected, cancerous or damaged cells to prevent cancer, autoimmunity or infection. Natural killer cells, cortical thymocytes, and dendritic cells do not belong to cytotoxic T cells but express CD8 protein as well.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

It is commonly thought that immune cell quantification is relatively easy and fully standardized, since the non-adherent, non-matrixed cells in peripheral blood can be marked with antibodies and flow-cytometrically quantified. Providing that cells are non-adherent, single cell suspensions, intact and cell-type specific surface antigens are available, flow cytometry is indeed a highly accurate cell quantification tool.

However, for many applications in research and medical routine, the named prerequisites for such precise measurements are not given:

1. Often, the material/samples measured are not derived from peripheral blood and thus the solubility and single cell suspension property is not met. This is, for example, true for all biopsy analyzes, such as performed in the pathological routine.
2. Even if the analyte is peripheral blood, the prerequisite of having intact cells is difficult to meet, since—in order to maintain their structural integrity ("intactness")—these cells must not be frozen or stored as EDTA-blood for more than 6 hours, before subfractions, such as granulocytes start disintegrating.
3. In contrast to the common perception, there are not highly specific (surface) antigens for all immune cell types and hence the identification of cell types is not as unambiguous as may be hoped. Since antigen expression is not a digital process, thresholds must be defined to decide, whether cells belong to the positive or negative fraction. For T cells, this problem is particular apparent:

Hence, for many applications the current methodological approaches for a quantitative determination of immune cells remain problematic, such as for routine testing in clinical applications, which usually requires some lag times, and hence robustness and stability of the analyte. As said, the flow cytometric methods used for measurement of cells in peripheral blood are not adequate for immune cells infiltrating other tissues, including solid tissues during tumor development or at/after inflammation. Hence, flow cytometric methods are not applied in these areas and the surrogate methods (mostly immune histochemistry) are at most semi-quantitative methods.

Hamerman et al. (in: Hamerman J A, Page S T, Pullen A M. Distinct methylation states of the CD8 beta gene in peripheral T cells and intraepithelial lymphocytes. J Immunol. 1997 Aug. 1; 159(3):1240-6) describe the CD8 coreceptor as expressed on both immature and mature T cells as either an alpha-beta heterodimer or an alpha alpha homodimer. Thymocytes and peripheral T cells express CD8 alpha-beta, whereas TCR alpha-beta+ intraepithelial lymphocytes (IEL) express CD8 alpha alpha or CD8 alpha-beta, and the majority of TCR gamma-delta+ IEL bear CD8 alpha alpha. The presence of CD8 beta enhances the signaling and adhesion properties of the CD8 alpha-beta coreceptor and is necessary for efficient T cell development in the thymus, but is not required for the extrathymic maturation of CD8 alpha alpha+ IEL. To address whether CD8 alpha alpha+ IEL express CD8 beta during their development, Hamerman et al. examined the methylation state of cytosines in the CD8 beta gene 5' regulatory region to identify those for which the methylation state inversely correlates with expression of the CD8 beta protein. They identified four such cytosines that were demethylated in CD8 beta-expressing thymocytes and T cells. Interestingly, these cytosines were also demethylated in CD4+ lymph node T cells that had transiently expressed CD8 beta during their development. The methylation state of these cytosines was examined in DNA purified from TCR alpha-beta+ CD8 alpha alpha+ and TCR alpha-beta+ CD8 alpha-beta+ IEL, as well as from TCR gamma-delta+ CD8 alpha alpha+ and CD3− CD8 alpha alpha+ IEL. The methylation pattern for TCR alpha-beta+ CD8 alpha alpha+ IEL DNA was distinct from that seen for DNA from CD4+ lymph node cells, suggesting that TCR alpha-beta+ CD8 alpha alpha+ IEL have not previously expressed CD8 beta. Analysis of DNA from CD3− CD8 alpha alpha+ IEL indicated that the unique methylation pattern of the CD8 beta gene in TCR alpha-beta+ CD8 alpha alpha+ IEL DNA was not due to transcription of the CD8 alpha gene or the influence of the gut microenvironment.

EP 1 213 360 describes a method of identifying a cell, tissue or nucleus, comprising collecting information on the methylation pattern of DNA isolated from the cell, tissue or nucleus and analyzing the resultant information.

WO 2008/132755 describes a test kit method for estimating CD4+/CD8+ T-cells based on anti-CD4+, anti-CD8+ monoclonal antibody detection carried out on microscopic glass slide. Additional staining visualizes T-cells to further enumeration under a microscope.

WO 02/083162 describes a method to treat, inhibit or prevent immune-driven rejection of grafted tissue or cells in a recipient host by administering a pharmaceutically effective amount of CD8+ T cell inhibitory agent.

EP 2058399 describes methods and reagents for vaccination which generate a CD8 T cell immune response.

EP 1753452 describes a method for altering the CD4/CD8 ratio and the mononuclear cellular infiltrate into a tumor whereby CD8 T cell level strongly decreases.

EP 1616016 describes gene therapy vectors having reduced immunogenicity based on CD8 alpha-chain finding use in extending the survival of transplant allografts and treating graft versus host disease in transplant recipients.

The above mentioned inventions require precise quantification on CD8 and it s subpopulations, which the present invention provides by a new methodology to effectively detect and quantify CD3+CD8+ and/or CD3+/−CD8+ cells, in particular for the first time detect and quantify CD8+ beta cells. Moreover the present invention enables flexible pre-clinical time framing which is not dependent on quick sample processing but rather allows long term sample storage and individual coordination between sample collecting and sample processing.

Furthermore, the publications of Melvin et al. (Hypomethylation in IFN-Gamma Gen correlates with expression of IFN-G, including CD8 cells., Eur J Immunol. 1995 February; 25(2):426-30), Landolfi M M et al. (CD2−CD4−CD8− lymph node T lymphocytes in MRL lpr/lpr mice are derived from a CD2+CD4+CD8+ thymic precursor J Immunol. 1993 Jul. 15; 151(2):1086-96), and Carbone A M et al. (Demethylation in CD8 suggests that CD4+ derives from CD8+ cells. Role of methylation pattern during cell development. Science. 1988 Nov. 25; 242(4882):1174-6) disclose methylation in connection with expression and differentiation.

WO 2008/132755 describes the identification of CD8 using immune histological methods.

While the measurement and determination of CD8+ cells is generally easy and is usually achieved through analyzing the expression of CD8 on the cellular surface, clinically, it remains challenging to specifically detect, identify, discriminate, and quantify actual CD3+CD8+ alpha/beta cells from whole CD8+ cells. Currently, clinical routine application is limited to the detection of CD8+ cells via detection of CD8 alpha and therefore lacks an established method to differentiate between CD3+CD8+ and CD3+/−CD8+ as well as to detect CD8 beta.

In view of the above, it is an object of the present invention to provide an improved and in particular robust method based on cytosine bisulfite convertibility analysis as a superior tool in order to more conveniently and reliably detect, identify, discriminate, and quantify CD3+/− subpopulations of CD8+ cells.

The present invention solves the above object by providing method for identifying subpopulations of cytotoxic T cells, comprising analyzing the bisulfite convertibility of at least one CpG position in a gene selected from the group of $CD8^+$ alpha and $CD8^+$ beta, wherein a bisulfite convertibility of at least one CpG position in the $CD8^+$ beta gene is indicative for a CD3+CD8+ cytotoxic T cell, and a bisulfite convertibility of the $CD8^+$ alpha gene is indicative for a CD3+/−CD8+ cytotoxic T cell.

Currently, no data describing CD8+ beta/beta cells exists. However, in a preferred embodiment thereof, the present invention for the first time will allow detection of such cells. Moreover, it is expected that the novel marker for CD8 beta will reveal new scientific insight into cell origin and cell state of CD8 beta chain expressing cells.

Currently, it is described in the literature that CD3+CD8+ NKT cells express the CD8 beta chain. However, the results of the present inventors indicate that for a portion of these cells there may exist a different epigenetic regulation that does not simply reflect or correspond to the currently known protein expression pattern.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma$(C and/or mC and/or hmC and/or fC and/or cC)
$b=\Sigma$(C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

The present invention is based on the surprising identification of a region of the CD8 gene by the inventors, namely the CD8 beta and alpha gene region, as specific epigenetic markers, allowing for the first time the identification of CD8 subpopulations of CD8 beta and alpha chain bearing cells as well as the clinical routine application of said analysis.

In the context of the present invention, the genomic region according to SEQ ID No. 1 is herein designated "CD8 beta chain specific bisulfite convertible region", which allows the identification of CD3+CD8+ cytotoxic T cells (alpha/beta CD8+ cells), and the genomic region according to SEQ ID No. 2 is herein designated "CD8 alpha chain specific bisulfite convertible region", which allows the identification of $CD3^{+/-}CD8^+$ cells (alpha/alpha CD8+ cells). Surprisingly, the discriminatory pattern of bisulfite convertible and non-convertible cytosine is exclusively limited to the genomic region according to SEQ ID No. 1 for CD8 beta bearing CD8+ cells as shown using the amplicons according to SEQ ID No. 5 and/or SEQ ID No. 6, and to the genomic region according to SEQ ID No. 2 for CD8 alpha bearing CD8+ cells as shown using the amplicon according to SEQ ID No. 7.

In a preferred embodiment of the method according to the present invention, both genes for $CD8^+$ alpha and $CD8^+$ beta are analyzed, preferably by analyzing amplicons derived from SEQ ID No. 1 and SEQ ID No. 2, and/or the CD8alpha specific non-methylated region derived from SEQ ID No. 3 and/or the CD8beta specific non-methylated region derived from SEQ ID No. 4.

In a preferred embodiment of the method according to the present invention for identifying a subpopulation of cytotoxic T cells (identification of CD3+CD8+ cells), said at least one CpG position is selected from a CpG position in an amplicon according to SEQ ID No. 2 and 3, and is preferably selected from positions 67, 92, 116, 123, 133, 161, 199, 231, 255, 267, and 291 in the amplicon No. 2004 according to SEQ ID No. 7 (CD8 alpha Assay), and positions 40 63 95 135 142 169 194 213 216 232 245 273 339 345, and 393 in the amplicon No. 2007 according to SEQ ID No. 5, and positions 165, 196, 219, 267, 277, 307, 314, 341, and 410 in the amplicon No. 2008 according to SEQ ID No 6 (CD8 beta Assays).

The inventive concept is based on the specific bisulfite convertibility of the CD8 beta and CD8 alpha specific region in CD8 positive cells. Using a simple and precise quantitative PCR method, the inventors show that specific pattern of cytosine modification of the said gene regions represents a specific marker for CD3+CD8+ and CD3+/−CD8+ cell counts in blood or tissues. In one preferred embodiment, one highly discriminative region of the CD8 beta and CD8 alpha gene is designated by the nucleotide sequence according to SEQ ID No. 3, and SEQ ID No. 4, which displays differential bisulfite convertibility when alpha/beta and alpha/alpha CD8+ cells are compared with all other cells.

The inventors could demonstrate that in the CD8 beta bearing cells the CpG motifs are almost completely convertible by bisulfite (i.e. to more than 70%, preferably 80%, preferably, more than 90% and most preferred more than 95%), whereas the same motifs are completely methylated in all CD8− and alpha/alpha CD8+ cells. In the same context, the inventors could demonstrate that in the CD8 alpha bearing cells the CpG motifs are almost completely convertible by bisulfite as well (i.e. to more than 70%, preferably 80%, preferably, more than 90% and most preferred more than 95%), whereas the same motifs are completely methylated in all CD8− cells.

The differential methylation of the CpG motifs within the aforementioned regions correlates with expression of CD8 alpha and beta chains. Thus, determination of the bisulfite convertibility of the CD8 alpha and beta locus is a valuable tool to identify subpopulations of CD8+ cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of CD8+ subpopulations without purification or any staining procedures. It even reports in solid tumors or other solid tissues the number of cells bisulfite convertible in said region, thus showing the total amount of tumor infiltrating CD8+ subpopulations.

The inventors found a bisulfite convertibility at the human CD8 beta and alpha locus to be restricted to CD3+CD8+ and CD3+/−CD8 cells, respectively, when tested against all major peripheral blood cell types. These data indicated that epigenetic modifications in the CD8 beta and alpha locus serve as valuable markers for the identification CD8+ subpopulations, regardless of the expression of both, CD8 beta and alpha chain.

Another preferred aspect of the method according to the present invention then further comprising a quantification of the relative amount of CD3+CD8+ and/or CD3+/−CD8+ cells based on comparing the relative amount(s) of bisulfite convertible DNA in regions specific for CD8 alpha and/or beta with the relative amount(s) of non-bisulfite convertible DNA of cell-specific regions. Said quantification thus is achieved based on the ratio of the bisulfite convertible DNA to non-convertible DNA in the genetic regions of CD8 beta and alpha as described and analyzed herein. Most preferred is a quantification of the relative amount of CD3+CD8+ and/or CD3+/−CD8+ cells is based on an (preferably parallel or simultaneous) analysis of the relative amount of bisulfite convertible DNA of cell-specific regions for CD8 alpha and/or beta, and of the relative amount of bisulfite convertible DNA of cell-unspecific genes (preferably designated "control genes" or "control regions", such as, for example, the gene for GAPDH). The analysis preferably further comprises an analysis of the bisulfite convertibility of at least one CpG position in a gene selected from cell-specific genes of CD3 T cells, CD4 T cells, regulatory T cells, monocytes, granulocytes, B cells, GAPDH, Th1, Th2, Th9, Th17, Th22, Tfh, NKT, and NK. In some embodiments, ratios of markers and respective numbers and/or amounts of cells can be determined and established based on, at least in part, the present analysis, for example of CD8+ beta to CD8+ alpha, overall CD8+ (alpha+beta) to overall CD3+, CD8+ beta to CD3+, CD8+ alpha to CD3+, and/or CD3+CD8+ to CD3+CD4+, and/or CD8+ beta or CD8+ alpha to Treg or overall CD8+ to Treg cells and/or markers, in a sample to be analyzed.

In a further preferred embodiment of the method according to the present invention, said analysis of bisulfite convertibility comprises amplification with at least one primer of suitable primer pairs that can be suitably designed based on SEQ ID No. 1 or SEQ ID 2, preferably oligomers according to any of SEQ ID No. 8 to 13.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the CD8 beta and alpha gene is produced that is a particularly preferred "tool" for performing the method(s) according to the present invention. Consequently, oligomers according to any of SEQ ID No. 8 to 13 or an amplicon as amplified by a primer pair based on SEQ ID No. 1 or 2 as mentioned above constitute preferred embodiments of the present invention.

The person of skill will furthermore be able to select specific subsets of CpG positions in order to minimize the amount of sites to be analyzed, for example at least one of CpG position 40, 63, 95, 135, 142, 169, 194, 213, 216, 232, 245, 273, 339, 345, 393, 165, 196, 219, 267, 277, 307, 314, 341, and 410 of the CD8$^+$ beta specific bisulfite convertible region (SEQ ID No. 1 or 4), or all sites as present on the CD8$^+$ beta specific bisulfite convertible region according to SEQ ID No 1 or 4. The positions are numerically counted from the 5'-end of an amplicon (e.g. positions 40, 63, 95, 135, 142, 169, 194, 213, 216, 232, 245, 273, 339, 345, and 393 in the amplicon No. 2007 according to SEQ ID No. 5, and positions 165, 196, 219, 267, 277, 307, 314, 341, and 410 in the amplicon No. 2008 according to SEQ ID No. 6) as generated and analyzed. Preferred are combinations of 3, 4, 5, 6, 7, 8, 9, or 10 positions, the analysis of which produces sufficient data and/or information in order to be informative in the context of the present invention, such as, for example, positions 142, 169, 194, 213, 216, 232, 245, 273, in the amplicon No. 2007 according to SEQ ID No. 5.

The person of skill will furthermore be able to select specific subsets of CpG positions in order to minimize the amount of sites to be analyzed, for example at least one of CpG position 67, 92, 116, 123, 133, 161, 199, 231, 255, 267, and 291 of the CD8 alpha specific bisulfite convertible region (SEQ ID No. 2 or 3), or all sites as present on the CD8+ alpha specific bisulfite convertible region according to SEQ ID No 2 or 3. The positions are numerically counted from the 5'-end of an amplicon (e.g. positions 67, 92, 116, 123, 133, 161, 199, 231, 255, 267, and 291 in the amplicon No. 2004 according to SEQ ID No. 7) as generated and analyzed. Preferred are combinations of 3, 4, 5, 6, 7, 8, 9, or 10 positions, the analysis of which produces sufficient data and/or information in order to be informative in the context of the present invention, such as, for example, positions 116, 123, 133, 161, 199, 231, 255, 267 in the amplicon No. 2004 according to SEQ ID No. 7.

In order to analyze the bisulfite convertibility of CpG positions, any known method to analyze DNA modification can be used. In a preferred embodiment of the method according to the present invention, the analysis of the DNA modification comprises a method selected from single molecule real-time technology (SMRT), DNA-modification-dependent polymerase kinetics, DNA sequencing through nanopores, strand sequencing, exonuclease sequencing, DNA-modification-dependent DNA hybridization, methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said CD3+CD8+ and CD3+/−CD8+ cells from all major peripheral blood cell types and/or non-blood cells, preferably, but not limited to, from CD19+ B lymphocytes, CD3+CD8+ T-Cells, CD15+ granulocytes, CD14+ monocytes, CD56+ Natural Killer Cells and CD3+CD56+ Natural Killer T-Cells, and CD3+CD4+ T helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, rat, monkey or human. The samples can be suitably pooled, if required.

Another preferred aspect of the method according to the present invention then further comprises the step of concluding on the immune status of said mammal based on said CD8+ subpopulations. The CD8+ subpopulations can be quantified and be used as a benchmark to relatively quantify further detailed subpopulations (as but not limited to CD4, Th1, Th2, Th9, Th17, Th22, Treg, Tfh), or it can be used as a predictive and/or screening and/or diagnostic and/or prognostic and/or adverse events detecting factor, or it can be used to finally detect this population to determine the overall immune activity status.

Another preferred aspect of the method according to the present invention is directed at the use of cytosine modification analysis of cell specific genes for CD3+, CD4+, regulatory T cells, Th1, Th2, Th9, Th17, Th22, Tfh, NKT, NK, monocytes, granulocytes and/or B cells for the detection and quality assurance and control of alpha/beta and/or alpha/alpha CD8+ cells.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of CD3+CD8+ and/or CD3+/−CD8+ cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said subpopulations of CD8+ cells as e.g. a sample for cell transfer into a patient.

Another preferred aspect of the method according to the present invention then relates to a method as above, further comprising formulating said subpopulation of cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID No. 8 to 13, an oligomer designed based on SEQ ID No. 1 or 2, the CD8 alpha and/or beta gene specific non-methylated region according to SEQ ID No. 3 or 4 or an amplicon selected from any of SEQ ID No. 3 to 7.

Yet another preferred aspect of the present invention then relates to a kit for identifying and/or monitoring said CD8 subpopulations (CD3+CD8+ cells and/or CD3+/−CD8+ cells) in a mammal based on the analysis of the bisulfite convertibility of at least one CpG position in the CD8 beta and CD8 alpha cell specific bisulfite convertible gene regions according to SEQ ID No. 1 and 2, respectively, and/or at least one amplicon selected from any of SEQ ID No. 3 to 7, respectively, comprising materials for performing a method according the present invention as described herein. Preferably, said kit comprises a) a bisulfite reagent, and b) materials for the bisulfite convertibility analysis of at least one CpG position selected from the positions 67, 92, 116, 123, 133, 161, 199, 231, 255, 267, and 291 in the amplicon No. 2004 according to SEQ ID No. 7, and positions 40, 63, 95, 135, 142, 169, 194, 213, 216, 232, 245, 273, 339, 345, and 393 in the amplicon No. 2007 according to SEQ ID No. 5, and positions 165, 196, 219, 267, 277, 307, 314, 341, and 410 in the amplicon No. 2008 according to SEQ ID No. 6. Further preferred, the positions consist of all positions in the CD8+ cell specific non-methylated region according to SEQ ID No. 1 and 2, respectively, and/or said amplicons according to any of SEQ ID Nos. 3 to 7, or positions 142, 169, 194, 213, 216, 232, 245, 273, in the amplicon No. 2007 according to SEQ ID No. 5 and/or positions 116, 123, 133, 161, 199, 231, 255, 267 in the amplicon No. 2004 according to SEQ ID No. 7.

The present invention also encompasses the use of oligomers or amplicon or a kit according to the present invention for identifying and/or for monitoring CD3+CD8+ and/or CD3+/−CD8+ cells in a mammal as described herein.

In summary, using the CD8 beta and alpha marker, the inventors very specifically identified, quantified and particularly differentiated both CD8 positive cells as such and its subpopulations, and in their relation to other cell types in a sample, for example to overall T-lymphocytes using the epigenetic markers for CD3, or their association to the CD4 T helper cells using the marker CD4. By such means for example CD4 positive T-lymphocytes could then be further distinguished from CD8 lymphocytes. This was not possible before the invention, since the protein expression of the marker CD8 beta and alpha cannot be used to reliable identify and quantify CD8 positive alpha/beta and alpha/alpha cells, nor was it possible from a (fresh, embedded or frozen) whole blood or tissue sample without specific means of conservation to provide a routine technology for the quantification of these cell types. Additionally, up to now no marker for CD8+ alpha/beta cells was discovered to identify and quantify said cells.

The invention will now be further described based on the following examples and with reference to the accompanying figures and the sequence listing, without being limited thereto. For the purposes of the present invention, all references as cited herein are incorporated by reference in their entireties. In the Figures and Sequences,

SEQ ID No. 1 shows the CD8 beta chain specific bisulfite convertible region according to the present invention.

SEQ ID No. 2 shows the CD8 alpha chain specific bisulfite convertible region according to the present invention.

SEQ ID No. 3 shows the sequence of the CD8A specific non-methylated region (alpha); the sequence contains discriminatory amplicon 2004 (AMP2004), and is confined at the 5' and 3' end by the non-discriminatory AMP 2003 and AMP2005, respectively.

SEQ ID No. 4 shows the sequence of the CD8B specific non-methylated region; the sequence contains discriminatory overlapping amplicons AMP2007 and AMP2008. The sequence is confined at the 3' end by the non-discriminatory amplicons AMP2011 and AMP1479 (near the CD8alpha gene).

SEQ ID No. 5 and SEQ ID No. 6 show the sequences of amplicons Amp 2007 and Amp 2008 for CD8 beta (overlapping), respectively.

SEQ ID No. 7 shows the sequence of amplicon Amp 2004 for CD8 alpha.

SEQ ID No. 8 to SEQ ID No. 13 show the sequences of specific oligomers according to the present invention.

SEQ ID No. 14 to SEQ ID No. 25 show the sequences of specific oligomers according to the present invention; SEQ ID No. 14 shows the forward Primer (nmF1.3) for AMP 2007; SEQ ID No. 15 shows the reverse primer (nmR1.5) for AMP 2007; SEQ ID No. 16 shows the forward primer (mF1.3) for AMP 2007; SEQ ID No. 17 shows the reverse primer (mR1.9) for AMP 2007; SEQ ID No. 18 shows the probe (nmP1.2), and SEQ ID No. 19 shows the probe (mP1.2); SEQ ID No. 20 shows the genomic sequence/position forward primer (nmF1.3) for AMP 2007; SEQ ID No. 21 shows the genomic sequence/position of reverse primer (nmR1.5) for AMP 2007; SEQ ID No. 22 shows the genomic sequence/position of forward primer (mF1.3) for AMP 2007; SEQ ID No. 23 shows the genomic sequence/position of reverse primer (mR1.9) for AMP 2007; SEQ ID No. 24 shows the genomic sequence/position of probe (nmP1.2) for AMP 2007, and SEQ ID No. 25 shows the genomic sequence/position of probe (mP1.2) for AMP 2007.

EXAMPLES

Example 1

The inventors have purified various blood subsets by FACS sorting including B cells (CD3−CD8−)(BLC), cytotoxic T lymphocytes (CD3+CD8+)(CTL), CD3−CD8− granulocytes (GRC) and CD3−CD8− monocytes (MOC), NK cells (CD3−CD8+)(NKC), NKT cells (CD3+CD8+) (NKT11), CD3+CD8− NKT cells (NKT14), and T helper cells (CD3+CD8−) (THC). DNA from the purified cells was bisulfate-treated and analyzed at various CpG dinucleotide motifs within the CD8 alpha and the CD8 beta gene. The inventors then compared the bisulfite convertibility (T for cytosine that was not-methylated in the original sequence versus finding C as for Cytosine that was methylated in the original (genomic) sequence).

Figure 1:
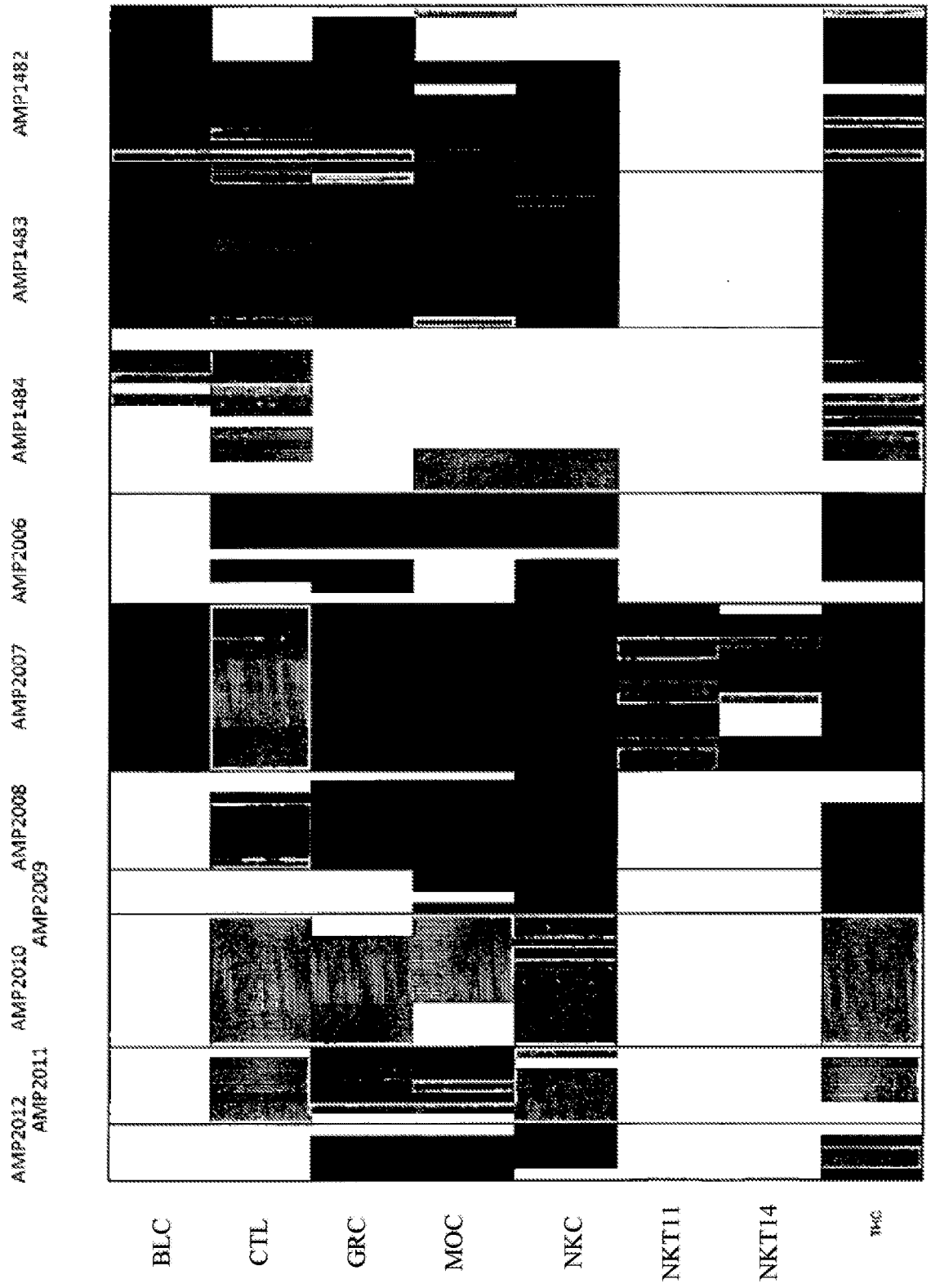
FIG. 1 shows the analysis of CpG sites on amplicons No. 1482, No. 1483, No. 1484, No. 2006, No. 2007 (SEQ ID No. 3), No. 2008, No. 2009, No. 2010, No. 2011, and No. 2012, respectively, within the CD8 beta gene. The numbers on the left indicate the respective CpG position on the respective amplicon. The abbreviations at the bottom indicate B cells (CD3−CD8−)(BLC), cytotoxic T lymphocytes (CD3+CD8+)(CTL), CD3−CD8− granulocytes (GRC) and CD3−CD8− monocytes (MOC), NK cells (CD3−CD8+)(NKC), NKT cells (CD3+CD8+)(NKT11), CD3+CD8− NKT cells (NKT14), and T helper cells (CD3+CD8−) (THC), respectively.

The CD8 beta data (FIG. 1) showed various CpG positions in the Amp 2007 of CD8 beta gene (see SEQ ID No. 1) that were non-methylated in CD3+CD8+ cytotoxic T-cells and partially non-methylated in CD3+CD8+ NKT cells while methylated in all other analyzed blood cell types. The differentially cytosine modified gene region Amp 2007 for CD8 beta is shown in SEQ ID No. 5.

Currently, it is described in the literature that CD3+CD8+ NKT cells express the CD8 beta chain. However, the results of the present inventors indicate that for a portion of these cells there may exist a different epigenetic regulation that does not simply reflect or correspond to the currently known protein expression pattern. This was also shown earlier for Treg cells and Th17 cells (see EP1826279 and PCT/EP2012/070676, both herewith incorporated by reference). Moreover, it is expected that the novel marker for CD8 beta will reveal new scientific insight into cell origin and cell state of CD8 beta chain expressing cells.

Figure 2:
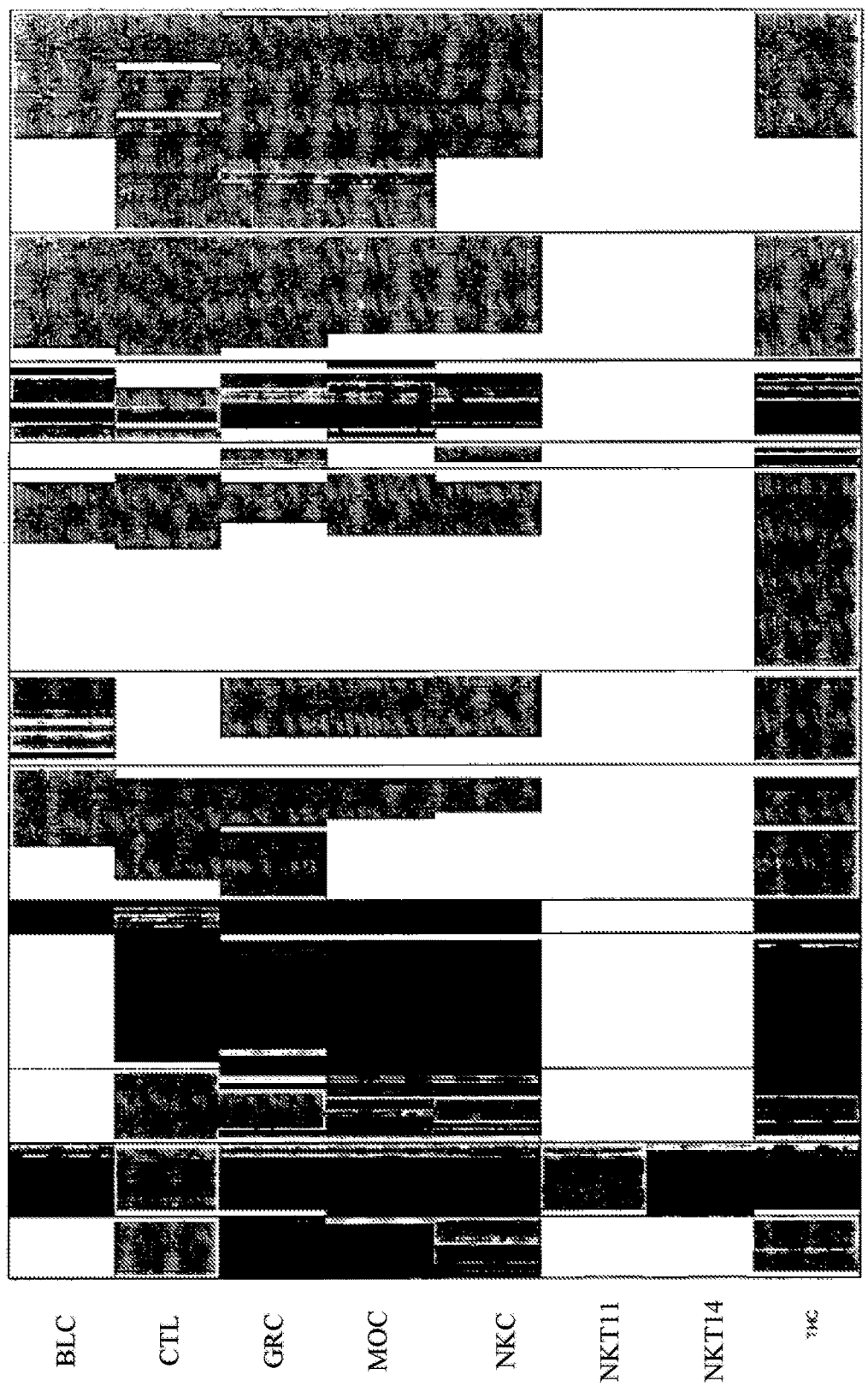
FIG. 2 shows the analysis of CpG sites on amplicons No. 1474, No. 1475, No. 1476, No. 1477, No. 1478 (SEQ ID No. 3), No. 1479, No. 1480, No. 1481, No. 2002, No. 2003, No. 2004, and No. 2005, respectively, within the CD8 alpha gene. The numbers on the left indicate the respective CpG position on the respective amplicon. The abbreviations at the bottom indicate B cells (CD3−CD8−)(BLC), cytotoxic T lymphocytes (CD3+CD8+)(CTL), CD3−CD8− granulocytes (GRC) and CD3−CD8− monocytes (MOC), NK cells (CD3-CD8+)(NKC), NKT cells (CD3+CD8+)(NKT11), CD3+CD8− NKT cells (NKT14), and T helper cells (CD3+CD8−)(THC), respectively.
Figure 3:
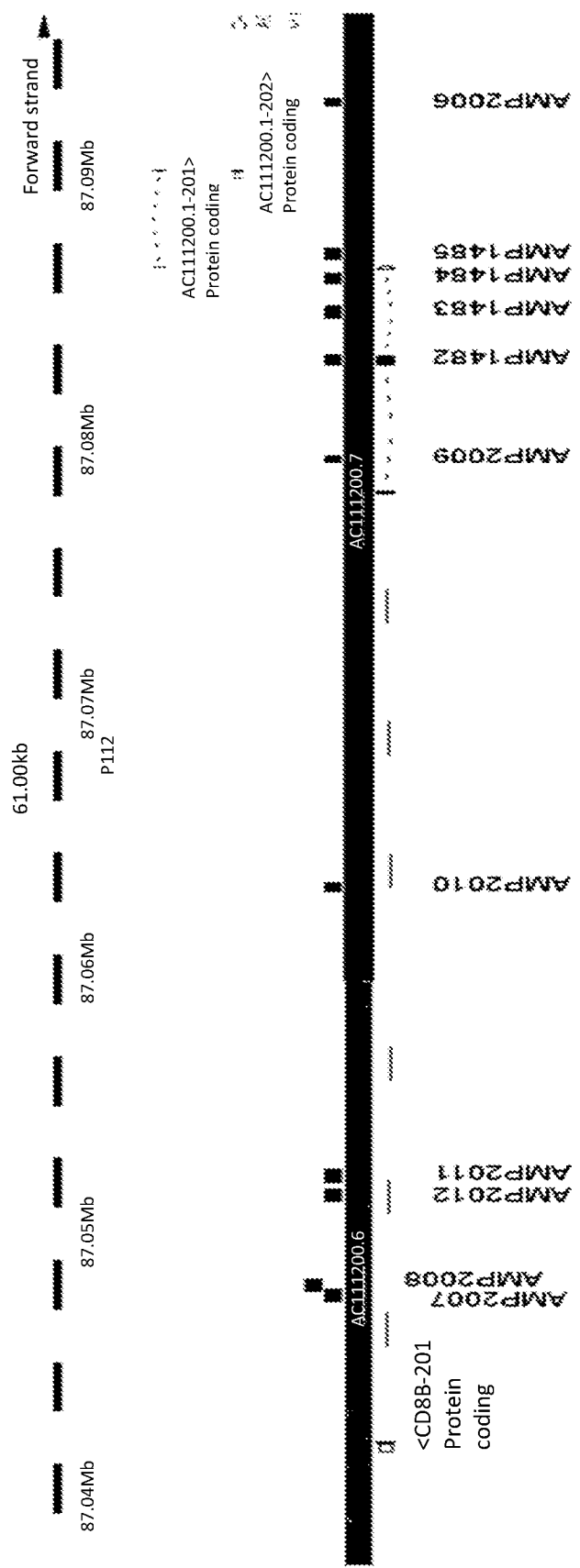
FIG. 3 shows the position of the specific bisulfite convertible regions within the CD8 beta gene according to the present invention, and the alignments of amplicons as analyzed (gray squares) against this region.
Figure 4:
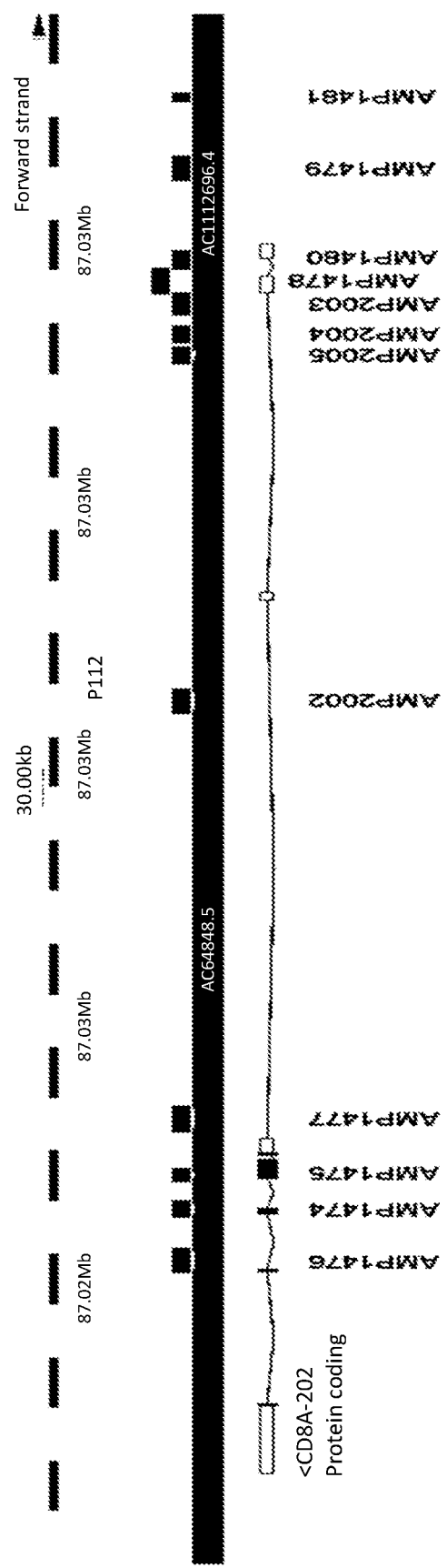
FIG. 4 shows the position of the specific bisulfite convertible regions within the CD8 alpha gene according to the present invention, and the alignments of amplicons as analyzed (gray squares) against this region.

The CD8 alpha data (FIG. 2) showed various CpG positions in the Amp 2004 of the CD8 alpha gene (see SEQ ID No. 2) that were non-methylated in CD3+CD8+ cytotoxic T-cells and in CD3+CD8+ NKT cells while methylated in all other analyzed blood cell types. The differentially cytosine modified gene region Amp 2004 for CD8 alpha is shown in SEQ ID No. 7. Similar to the bisulfite conversion pattern of CD8 beta, also for the CD8 alpha gene there was a partial methylation found for cells that in the literature are described as CD8 alpha protein expressing cells (NK cells). FACS sorting via protein expression does not reflect actual epigenetic regulation status. Future scientific studies on the epigenetic pattern in the CD8 alpha gene using the present epigenetic CD8 alpha marker will further deepen the understanding of e.g. origin and state of said cells.

Example 2: Assessment of $CD8^+$ CD3+ T-Cells in Human Peripheral Blood

Novel epigenetic assays were compared with flow cytometry assays for the detection of CD8 and CD3 cells and ratios thereof. As both techniques determine the same biological variable, they should be essentially concordant.

Human peripheral blood was obtained from healthy volunteers. DNA from venous blood was purified using DNeasy Blood&Tissue Kit (Qiagen) according to manufacturer instructions. Additionally, capillary blood was spotted on FTA® Cards (Whatman) and dried at room temperature overnight. DNA was extracted from 6×6 mm spots using QIAamp DNA Kit (Qiagen). Following, DNA was bisulfite converted: Up to 1.5 µg genomic DNA were converted applying Epitect (Fast) Bisulfite Kits (Qiagen) according to manufacturer's protocol. Whole blood DNA was purified using a Microcon®-30 Centrifugal Filter (Millipore). qPCR: Highly cell-type specific methylation-dependent qPCRs for quantification of $CD3^+$ and $CD8^+$ T-cells were developed and performed as follows: One set of oligonucleotides (i.e., forward/reverse primer and hydrolysis probe) specific for TpG- or CpG-variant was used. Reactions were carried out in triplicates in 10 µl total volume using 2× Probe Mastermix (Roche), 15 pmol of each primer, 1.25-2.5 pmol probe, 25 ng λ-DNA (NEB) and up to 82 ng template DNA or plasmid at 1×95° C. 10 min, and 50 cycles 95° C. 15 sec and 61° C. 60 sec. For CD8B TpG, $MgCl_2$ was added to a final concentration of 4.7 mM. Amplification crossing points were determined using LightCycler480 software (Roche) deploying the second-derivative maximum method. Percental target cells were calculated as previously described (Sehouli, J. et al. 2011. Epigenetic quantification of tumor-infiltrating T-lymphocytes. *Epigenetics* 6:236-246). For blood samples, normalization of qPCR values ($x_N$) was carried out as follows: $x_N = qPCR_x/qPCR_{Cal}*FCM_{Cal}$ using a calibrator (Cal) with a determined FCM value ($FCM_{Cal}$). Plasmids: Synthesized target regions for real-time qPCR assays were inserted into plasmid pUC57 or pJet1.2 (Genscript Inc.). Linearized plasmids were diluted in 10 ng/µl of λ-phage DNA (NEB) to obtain qPCR standards of 31250, 6250, 1250, 250, 50, and 30 copies per reaction.

Oligonucleotides: qPCR: The sequences of amplification primers are as follows:

```
Forward Primer (nmF1.3) AMP 2007:
                              (SEQ ID No. 14)
GGT TAA GAA ATT AAT AGG AAA AAG AAT Reverse primer (nmR1.5) AMP 2007:
                              (SEQ ID No. 15)
CTT CCC CAC CAC AAT ACA ACA Forward primer (mF1.3) AMP 2007:
                              (SEQ ID No. 16)
GGT TAA GAA ATT AAT AGG AAA AAG AAC Reverse primer (mR1.9) AMP 2007:
                              (SEQ ID No. 17)
CCC CAT ATT ACT TCC CCG
```

The sequences of probes are as follows:

```
Probe (nmP1.2):
                              (SEQ ID No. 18)
TGT TTG TGA GGT ATT TAG TTG ATG GGA GTT TTG
```

```
Probe (mP1.2):
                                        (SEQ ID No. 19)
CGT TTG TGA GGT ATT TAG TCG ACG GGA G
```

Genomic positions of amplification primers and probes are as follows:

```
Genomic forward Primer (nmF1.3) AMP 2007
                                        (SEQ ID No. 20)
GGTTAAGAAACCAACAGGAAAAGAAC Reverse primer (nmR1.5) AMP 2007:
                                        (SEQ ID No. 21)
CGTTGTATTGTGGCGGGGAAG Forward primer (mF1.3) AMP 2007:
                                        (SEQ ID No. 22)
GGTTAAGAAACCAACAGGAAAAGAAC Reverse primer (mR1.9) AMP 2007:
                                        (SEQ ID No. 23)
CGGGGAAGCAACATGGGG Probe (nmP1.2) AMP 2007:
                                        (SEQ ID No. 24)
CGCCTGTGAGGCACTCAGCCGACGGGAGCTTTG Probe (mP1.2) AMP 2007:
                                        (SEQ ID No. 25)
CGCCTGTGAGGCACTCAGCCGACGGGAG
```

CD3− and GAPDH-qPCR positions of amplification primers and probes were described previously (Sehouli, J. et al. 2011. Epigenetic quantification of tumor-infiltrating T-lymphocytes. *Epigenetics* 6:236-246).

Flow cytometry: Cell sorting: Peripheral blood samples were fractionated in a MACS/FACS sorting protocol (Baron, U., Floess, S., Wieczorek, G., Baumann, K., Grützkau, A., Dong, J., Thiel, A., Boeld, T. J., Hoffmann, P., Edinger, M., et al. 2007. DNA demethylation in the human FOXP3 locus discriminates regulatory T cells from activated FOXP3(+) conventional T cells. *Eur J Immunol* 37:2378-2389.) for granulocytes (CD15$^+$), monocytes (CD3$^-$/CD14), NK cells (CD56$^+$/CD16$^+$), B cells (CD19$^+$), CD8$^+$ T-cells (CD3$^-$/CD8$^+$/CD4$^-$). Cell counting: 50 µl peripheral blood was stained in TruCount™ tubes (Becton-Dickinson) with anti-CD3 FITC, anti-CD4 PerCP and anti-CD8 APC. After staining and erythrocyte lysis, cells were analyzed on FACS-LSRII (Becton Dickinson). Absolute CD3$^-$ and CD3$^+$CD8$^+$ T-cell counts per microliter of peripheral blood were calculated by the ratio between analyzed cells and fluorescent TruCount™ beads according to the manufacturer's instructions. Anti-CD45 PE staining was performed for assessment of relative cell counts.

Statistical analysis: For Bland-Altman plots, errors were given in percent (FCM-qPCR). Two-sided t-tests were performed to test if mean differences (bias) were significantly different from zero. Linear regression was performed to obtain slope and intercept. Shapiro-Wilk tests and Q-Q-Plots were used to assess normality assumptions of regression residuals. Residuals were visually inspected with respect to homogenous scattering. P-values <0.05 were considered significant. In ROC analysis optimal cutoff value and accuracy was determined as value minimizing the Euclidean distance to the coordinate point with optimal sensitivity and specificity. All p-values correspond to two-sided tests. Statistics software SPSS 21.0 (IBM) and R 2.14 were employed.

T-cell counts in peripheral blood. Randomly selected and blinded peripheral blood samples from 39 healthy and 86 HIV$^+$ donors were tested with epigenetic assays for CD3 and CD8B and compared with the according Flow-Cytometry (FCM)-based T-cell counting procedures. Healthy and HIV$^+$ subjects had a median age of 55 (range: 19-67) and 46 (range: 23-75) years, respectively. 87.2% of HIV subjects were treated with anti-retroviral therapy and 17.4% had opportunistic infections.

Figure 5:
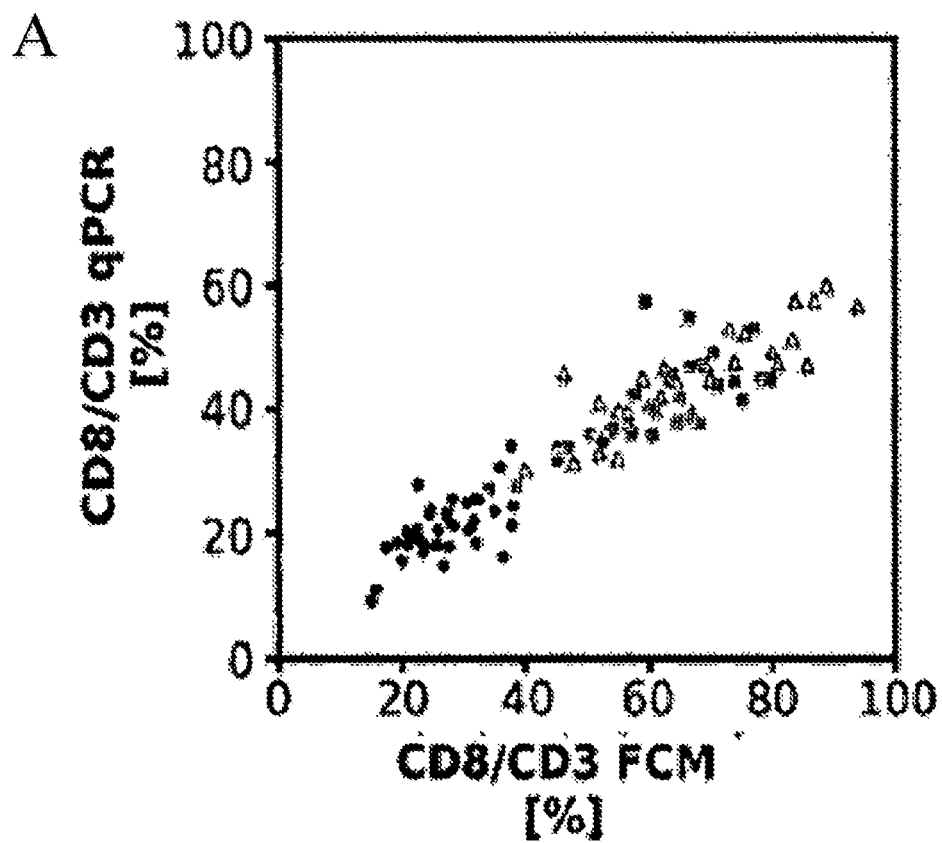
FIG. 5 shows the comparison of qPCR and FCM measurements. (A) Ratio of $CD8^+$ to $CD3^+$ T-cells in (%) as determined by FCM (x-axis) and epigenetic qPCR measurement (y-axis) in peripheral blood of healthy controls (black circles) and $HIV^+$ patients (grey squares; white triangles). (B) Bland-Altman-diagrams for method agreement of $CD8^+$ to $CD3^+$ T-cells. Plotted is the mean of the determined ratios by both methods (x-axis) and the corresponding percentaged differences (FCM-qPCR). The solid line represents the estimated mean difference, dotted lines the estimated upper and lower limits of agreement.
Figure 5:
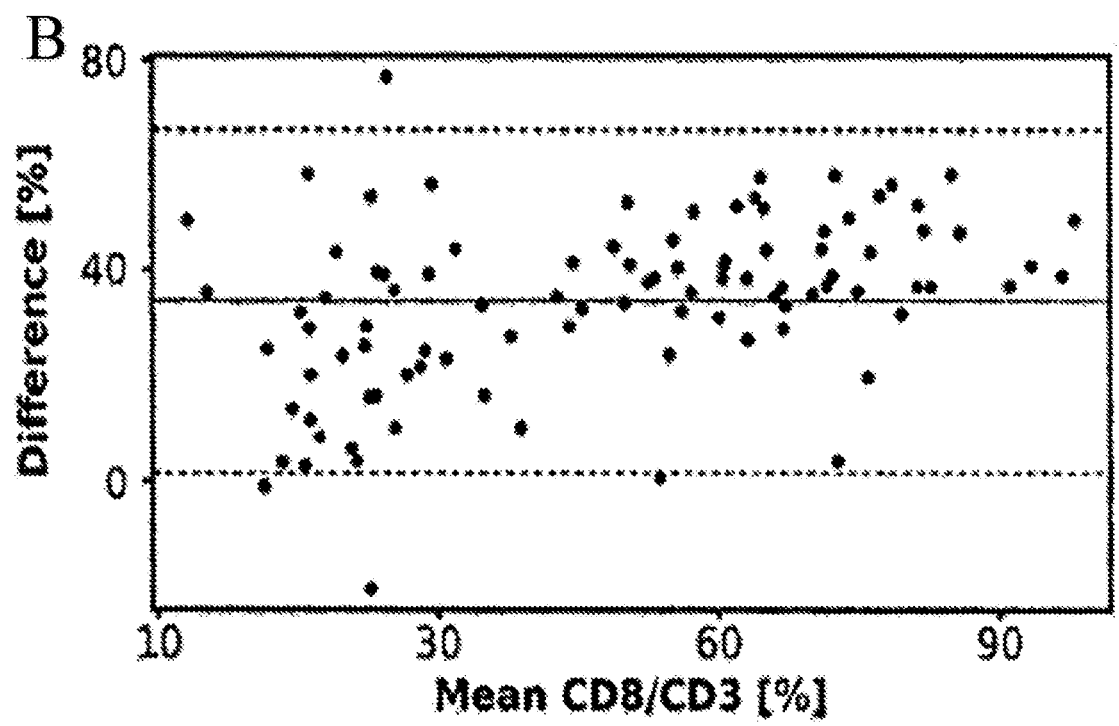

Method agreement for CD8/CD3 ratio. The median CD8/CD3 ratio in healthy subjects was 21.0% in qPCR tests (FCM: 27.6%) ranging from 9.1%-34.7% (FCM: 15.1%-52.6%) while HIV$^+$ patients exhibited a median of 41.5% (FCM: 64.6%) ranging from 25.1%-60.9% (FCM: 34.1%-94.0%, FIG. 5A). Pearson correlation between qPCR and FCM data was at 0.94 (p<0.001). The estimated mean difference in the Bland-Altman percent-difference diagram indicated a 34.1% smaller qPCR measurement compared to FCM (LoA: 66.6% and 1.6% (FIG. 5B)). The inventors also tested agreement of epigenetic qPCRs for CD8/CD3 ratio between venous blood and dried capillary blood from six healthy donors (see Table A).

When employing these assays on whole blood, good method agreement between cell ratios obtained by qPCR and FCM was observed. Also, concordance was observed for clinically used FCM- and experimentally determined qPCR-cutoffs. qPCRs were also performed from dried blood spots and showed data equivalent to those from venous blood.

TABLE A

Evaluation of qPCR performance from dried blood spots compared to fresh blood according to Bland-Altman method.

| | CD8/CD3 [%] | |
|---|---|---|
| | Venous blood | DBS |
| Donor 1 | 15.4 | 13.9 |
| Donor 2 | 25.1 | 23.7 |
| Donor 3 | 28.4 | 28.1 |
| Donor 4 | 22.5 | 20.5 |
| Donor 5 | 19.8 | 24.3 |
| Donor 6 | 21.6 | 22.3 |
| Mean | 22.1 | 22.1 |
| MD | | 0.00 |
| upper LoA | | 4.8 |
| lower LoA | | −4.8 |

MD—mean difference, LoA—limits of agreement.

The invention claimed is:

1. A method for identifying CD3+CD8+ natural killer T cells (NKT cells) in a sample derived from a human, wherein said method comprises:
   i) determining the methylation status of at least one CpG position in a genomic region for CD8 beta from the human sample, said genomic region comprising SEQ ID NO: 5 and/or SEQ ID NO: 6, comprising the steps of:
      a) treating the genomic region comprising SEQ ID NO: 5 and/or SEQ ID NO: 6 with bisulfite,
      b) amplifying the bisulfite treated genomic region comprising SEQ ID NO: 5 with a first primer pair of SEQ ID NOs: 8 and 9 to produce a first amplicon, and/or amplifying the bisulfite treated genomic region comprising SEQ ID NO: 6 with a second primer pair of SEQ ID NOs: 10 and 11 to produce a second amplicon,
      c) determining in the first amplicon the methylation status of the CpG positions 40, 63, 95, 135, 142, 169, 194, 213, 216, 232, 245, 273, 339, 345, and 393, the CpG positions being relative to SEQ ID NO: 5 and/or determining in the second amplicon the methylation status of the CpG positions 165, 196, 219, 267, 277, 307, 314, 341, and 410, the CpG positions being relative to SEQ ID NO: 6; and
   ii) determining the methylation status of at least one CpG position in a genomic region for CD8 alpha from the human sample, said genomic region comprising SEQ ID NO: 7, comprising the steps of:
      a) treating the genomic region comprising SEQ ID NO: 7 with bisulfite,
      b) amplifying the bisulfite treated genomic region comprising SEQ ID NO: 7 with a suitable primer pair to produce a third amplicon,
      c) determining in the third amplicon the methylation status of the CpG positions 67, 92, 116, 123, 133, 161, 199, 231, 255, 267, and 291, the CpG positions being relative to SEQ ID NO: 7; and
   iii) identifying the immune cells as CD3+CD8+ NKT cells when the CpG positions in the first amplicon and/or second amplicon are more than 80% methylated, and the CpG positions in the third amplicon are less than 20% methylated.

2. The method according to claim 1, further comprising quantifying the relative amount of said CD3+CD8+ NKT cells, said quantifying comprising detecting the methylation status of a control gene and comparing said methylation status of the control gene with the methylation status of said CpG positions in the first, second, and/or third amplicons.

3. The method according to claim 1, wherein said nucleic acid based assay is performed on a DNA-chip.

4. The method according to claim 1, wherein said sample is selected from a body fluid, tissue, organ or a blood lymphocyte or a fraction thereof.

5. The method according to claim 1, wherein said method is performed without a step of purifying and/or enriching the immune cells in the sample derived from the human.

6. The method according to claim 1, further comprising formulating said CD3+CD8+ NKT cells as identified for transplantation into a patient.

7. The method according to claim 1, wherein said human suffers from or is likely to suffer from an autoimmune disease, transplant rejection, infectious disease, cancer, and/or allergy.

8. A method for monitoring the level of CD3+CD8+ NKT cells in a human, comprising performing the method according to claim 1, and comparing said relative amount of the CD3+CD8+ NKT cells to a sample taken earlier or in parallel from the same human and/or to a control sample.

9. The method according to claim 8, further comprising treating the human with a chemical and/or biological substance, and measuring and/or monitoring the amount of said CD3+CD8+ NKT cells in response to said chemical and/or biological substance.

* * * * *